US012637657B2

(12) United States Patent
Marmorstein et al.

(10) Patent No.: US 12,637,657 B2
(45) Date of Patent: May 26, 2026

(54) METHODS AND MATERIALS FOR CULTURING, PROLIFERATING, AND DIFFERENTIATING STEM CELLS

(71) Applicant: Mayo Foundation for Medical Education and Research, Rochester, MN (US)

(72) Inventors: Alan D. Marmorstein, Rochester, MN (US); Jarel K. Gandhi, Rochester, MN (US); Travis J. Knudsen, Rochester, MN (US); Matthew S. Hill, Rochester, MN (US); Jose S. Pulido, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 124 days.

(21) Appl. No.: 16/618,579

(22) PCT Filed: Jun. 5, 2018

(86) PCT No.: PCT/US2018/035992
§ 371 (c)(1),
(2) Date: Dec. 2, 2019

(87) PCT Pub. No.: WO2018/226648
PCT Pub. Date: Dec. 13, 2018

(65) Prior Publication Data
US 2020/0157497 A1 May 21, 2020

Related U.S. Application Data

(60) Provisional application No. 62/634,580, filed on Feb. 23, 2018, provisional application No. 62/515,286, filed on Jun. 5, 2017.

(51) Int. Cl.
*C12N 5/079* (2010.01)

(52) U.S. Cl.
CPC ........ *C12N 5/0621* (2013.01); *C12N 2500/98* (2013.01); *C12N 2501/998* (2013.01); *C12N 2506/45* (2013.01); *C12N 2533/30* (2013.01); *C12N 2533/50* (2013.01); *C12N 2533/56* (2013.01)

(58) Field of Classification Search
CPC .............. C12N 5/0621; C12N 2506/45; C12N 2533/56; C12N 2500/98; C12N 2501/998
See application file for complete search history.

(56) References Cited

U.S. PATENT DOCUMENTS

| | | | |
|---|---|---|---|
| 5,284,476 A | 2/1994 | Koch | |
| 5,356,395 A | 10/1994 | Chen | |
| 6,045,791 A | 4/2000 | Liu | |
| 6,179,826 B1 | 1/2001 | Aebischer et al. | |
| 6,413,245 B1 | 7/2002 | Yaacobi et al. | |
| 6,607,522 B1 | 8/2003 | Hamblin et al. | |
| 8,231,908 B2 | 7/2012 | Kinoshita | |
| 8,425,473 B2 | 4/2013 | Ho et al. | |
| 11,679,180 B2 | 6/2023 | Marmorstein et al. | |
| 2004/0115176 A1 | 6/2004 | Swartz et al. | |
| 2004/0236343 A1 | 11/2004 | Taylor et al. | |
| 2006/0047250 A1 | 3/2006 | Hickingbotham et al. | |
| 2007/0060887 A1 | 3/2007 | Marsh et al. | |
| 2007/0225631 A1 | 9/2007 | Bowlin et al. | |
| 2007/0237757 A1 | 10/2007 | Wyatt et al. | |
| 2008/0097335 A1 | 4/2008 | Trogden et al. | |
| 2008/0115796 A1 | 5/2008 | Montanari et al. | |
| 2009/0227934 A1 | 9/2009 | Euteneuer et al. | |
| 2009/0270487 A1 | 10/2009 | Wyatt et al. | |
| 2010/0284998 A1 | 11/2010 | Smith et al. | |
| 2010/0291058 A1 | 11/2010 | Bowlin et al. | |
| 2011/0171185 A1 | 7/2011 | Klimanskaya et al. | |
| 2011/0269173 A1 | 11/2011 | Zhu et al. | |
| 2012/0207723 A1 | 8/2012 | He et al. | |
| 2012/0219737 A1 | 8/2012 | Sugino et al. | |
| 2012/0269776 A1 | 10/2012 | Alaminos Mingorance et al. | |
| 2013/0004469 A1 | 1/2013 | Glazier et al. | |
| 2013/0046382 A1 | 2/2013 | Mazzocchi et al. | |
| 2013/0218167 A1 | 8/2013 | Coffey et al. | |
| 2013/0253405 A1 | 9/2013 | Tu | |
| 2013/0281908 A1 | 10/2013 | Schaller et al. | |
| 2013/0295060 A1 | 11/2013 | Yang et al. | |
| 2013/0345618 A1 | 12/2013 | Auld et al. | |
| 2014/0057281 A1 | 2/2014 | Takahashi et al. | |
| 2014/0234381 A1 | 8/2014 | Tao et al. | |

(Continued)

FOREIGN PATENT DOCUMENTS

| | | |
|---|---|---|
| AU | 4802901 | 8/2001 |
| CN | 103007355 | 4/2013 |

(Continued)

OTHER PUBLICATIONS

Linsley et al. "The effect of fibrinogen, collagen type I, and fibronectin on mesenchymal stem cell growth and differentiation into osteoblasts." Tissue Engineering Part A 19.11-12 (2013): 1416-1423. (Year: 2013).*

ThermoFisher, "Nunc Cell-culture treated Six-well plate description" https://www.thermofisher.com/order/catalog/product/140675, accessed Jan. 27, 2022 (Year: 2022).*

Vaajasaari et al. "Toward the defined and xeno-free differentiation of functional human pluripotent stem cell-derived retinal pigment epithelial cells." Molecular Vision 17 (2011): 558. (Year: 2011).*

Ahmed et al. "Autologous fibrin glue as an encapsulating scaffold for delivery of retinal progenitor cells." Frontiers in Bioengineering and Biotechnology 2 (2015): 85. (Year: 2015).*

Chernousov et al. "αVβ8 integrin is a Schwann cell receptor for fibrin." Experimental cell research 291.2 (2003): 514-524. (Year: 2003).*

(Continued)

*Primary Examiner* — Emily A Cordas
(74) *Attorney, Agent, or Firm* — Fish & Richardson P.C.

(57) ABSTRACT

This document provides RPE cells and RPE monolayers. For example, compositions containing RPE cells or RPE monolayers as well as methods and materials for making RPE cells or RPE monolayers from, for example, stem cells (e.g., iPSCs) are provided.

6 Claims, 44 Drawing Sheets

(56) References Cited

U.S. PATENT DOCUMENTS

| 2015/0032223 A1 | 1/2015 | Miyagawa et al. |
| 2015/0118200 A1 | 4/2015 | Sugino et al. |
| 2015/0132847 A1 | 5/2015 | Lipke et al. |
| 2015/0147768 A1* | 5/2015 | Chan ........................ C12N 1/20 |
| | | 249/141 |
| 2015/0159134 A1 | 6/2015 | Choudhary et al. |
| 2015/0368713 A1 | 12/2015 | Bharti et al. |
| 2016/0058908 A1 | 3/2016 | Oohashi et al. |
| 2016/0168523 A1 | 6/2016 | Glazier et al. |
| 2016/0331867 A1 | 11/2016 | Chiou |
| 2016/0346006 A1 | 12/2016 | Hickengbotham et al. |
| 2017/0067017 A1 | 3/2017 | Meyer et al. |
| 2017/0246350 A1 | 8/2017 | Du et al. |
| 2018/0049918 A1 | 2/2018 | Benner et al. |
| 2019/0000669 A1 | 1/2019 | Hammack et al. |
| 2019/0169569 A1 | 6/2019 | Bharti et al. |
| 2020/0061246 A1 | 2/2020 | Marmorstein |
| 2022/0000664 A1 | 1/2022 | Gandhi et al. |
| 2023/0277728 A1 | 9/2023 | Marmorstein et al. |

FOREIGN PATENT DOCUMENTS

| CN | 103656742 | 3/2014 |
| CN | 110520139 | 11/2019 |
| CN | 114807035 | 7/2022 |
| EP | 0700429 | 10/2000 |
| EP | 2554661 | 4/2008 |
| EP | 3551216 | 10/2019 |
| JP | H09-501303 | 2/1997 |
| JP | 2006501848 | 1/2006 |
| JP | 2007-500070 | 1/2007 |
| JP | 2007524411 | 8/2007 |
| JP | 2013502234 | 1/2013 |
| JP | 2013502915 | 1/2013 |
| JP | 2016052271 | 4/2016 |
| KR | 10-2007-0093991 | 9/2007 |
| KR | 10-2008-0036102 | 4/2008 |
| MX | 2019006576 | 8/2019 |
| WO | WO 94/25569 | 11/1994 |
| WO | WO 2004/112893 | 12/2004 |
| WO | WO 2005/090550 | 9/2005 |
| WO | WO 2007/013331 | 2/2007 |
| WO | WO 2007/119213 | 10/2007 |
| WO | WO 2012/177968 | 12/2012 |
| WO | WO 2013/158919 | 10/2013 |
| WO | WO 2014/106136 | 7/2014 |
| WO | WO 2014/121077 | 8/2014 |
| WO | WO 2015/077498 | 5/2015 |
| WO | WO 2015/087231 | 6/2015 |
| WO | WO 2016/047849 | 3/2016 |
| WO | WO 2016/062862 | 4/2016 |
| WO | WO 2017/044488 | 3/2017 |
| WO | WO 2018/106414 | 6/2018 |

OTHER PUBLICATIONS

Algvere et al., "Transplantation of RPE in age-related macular degeneration: observations in disciform lesions and dry RPE atrophy," Graefes Arch. Clin. Exp. Ophthalmology, Mar. 1997, 235(3):149-158.

Chowdhury et al., "A Novel Rat Model to Study the Role of Intracranial Pressure Modulation on Optic Neuropathies," PLoS One, Dec. 2013, 8(12):e82151, 8 pages.

Da Cruz et al., "Phase I clinical study of an embryonic stem cell-derived retinal pigment epithelium patch in age-related macular degeneration," Nat. Biotechnology, Apr. 2018, 36(4):328-337.

Fernandes et al., "Development of a new tissue injector for subretinal transplantation of human embryonic stem cell derived retinal pigmented epithelium," Int. J. Retin. Vitreous, Oct. 2017, 3:41, 9 pages.

Kamao et al., "Evaluation of the Surgical Device and Procedure for Extracellular Matrix-Scaffold-Supported Human iPSC-Derived Retinal Pigment Epithelium Cell Sheet Transplantation," Invest Ophthalmol. Vis, Science, Jan. 2017, 58(1):211-220.

Kashani et al., "A bioengineered retinal pigment epithelial monolayer for advanced, dry age-related macular degeneration," Sci. Transl. Medicine, Apr. 4, 2018, 10(435):eaao4097, 11 pages.

Sharma et al., "Clinical-grade stem cell-derived retinal pigment epithelium patch rescues retinal degeneration in rodents and pigs," Sci. Transl, Medicine, Jan. 16, 2019, 11(475):eaat5580, 47 pages.

Stanzel et al., "Subretinal Delivery of Ultrathin Rigid-Elastic Cell Carriers Using a Metallic Shooter Instrument and Biodegradable Hydrogel Encapsulation," Invest Ophthalmol. Vis. Science, Jan. 2012, 53(1):490-500.

Ahmed et al., "Autologous fibrin glue as an encapsulating scaffold for delivery of retinal progenitor cells," Front. Bioeng. Biotechnology, Feb. 3, 2015, 2:85, 11 pages.

Mooney et al., "Specific Fibrinogen and Thrombin Concentrations Promote Neuronal Rather Than Glial Growth When Primary Neural Cells Are Seeded Within Plasma-Derived Fibrin Gels," Tissue Eng. Part A, May 1, 2010, 16(5):1607-1619.

Age-Related Macular Degeneration (AMD) | National Eye Institute, (n.d.). https://nei.nih.gov/eyedata/amd#5 (accessed Sep. 14, 2016).

Ausubel et al., "GMP scale-up and banking of pluripotent stem cells for cellular therapy applications," InHuman Pluripotent Stem Cells, Humana Press, 2011:147-59, 2011.

Blombäck, "Fibrinogen structure, activation, polymerization and fibrin gel structure," Thromb Res., 75(3):327-328, 1994.

Brandl et al., "In-Depth Characterisation of Retinal Pigment Epithelium (RPE) Cells Derived from Human Induced Pluripotent Stem Cells (hiPSC)," NeuroMolecular Med., 16(3):551-64, Sep. 2014.

Calejo et al., "Honeycomb porous films as permeable scaffold materials for human embryonic stem cell-derived retinal pigment epithelium," Journal of Biomedical Materials Research Part A 104.7 (2016):1646-1656.

Carr et al., "Molecular characterization and functional analysis of phagocytosis by human embryonic stem cell-derived RPE cells using a novel human retinal assay," Mol. Vis., 15:283-95, Feb. 2009.

Chaurasia et al., "Optimization of Fibrin Glue Spray Systems for Ophthalmic Surgery," Transl. Vis. Sci. Technol., 1(2):2, Jun. 2012.

Chen et al., "Considerations in designing systems for large scale production of human cardiomyocytes from pluripotent stem cells," Stem cell research & therapy, 5(1):12, Mar. 2014.

Dalvin et al., "Vitelliform dystrophies: Prevalence in Olmsted County, Minnesota, United States," Ophthalmic Genet., 38(2):143-7, Mar. 2016.

De Boer et al., "Fibrin and activated platelets cooperatively guide stem cells to a vascular injury and promote differentiation towards an endothelial cell phenotype," Arteriosclerosis, thrombosis, and vascular biology, 26(7):1653-9, Jul. 2006.

Del Priore et al., "Survival of allogeneic porcine retinal pigment epithelial sheets after subretinal transplantation," Invest Ophthalmol. Vis. Sci., 45(3):985-992, 2004.

Diniz et al., "Subretinal Implantation of Retinal Pigment Epithelial Cells Derived From Human Embryonic Stem Cells: Improved Survival When Implanted as a Monolayer," Invest. Ophthalmol. Vis. Sci., 54(7):5087-96, Jul. 2013.

Eaker et al., "Concise review: Guidance in developing commercializable autologous/patient-specific cell therapy manufacturing," Stem cells translational medicine, (11):871-83, Nov. 2013.

Filho et al., "Grid laser photocoagulation in the treatment of serous avascular pigment epithelial detachment in age-related macular degeneration," Arq. Bass. Oitalmol., 77(5):315-20, 2014.

Filová et al., "Vascular endothelial cells on two-and three-dimensional fibrin assemblies for biomaterial coatings," J. Biomed. Mater. Res. A., 90A(1):55-69, Jun. 2009.

Fitzpatrick et al., "PNIPAAm-grafted-collagen as an injectable, in situ gelling, bioactive cell delivery scaffold," Biomacromolecules, 11(9):2261-7, Sep. 2010.

Gandhi et al., "Differential intraocular pressure measurements by tonometry and direct cannulation after treatment with soluble adenylyl cyclase inhibitors," Journal of Ocular Pharmacology and Therapeutics, 33(8):574-81, Oct. 2017.

Gandhi et al., "Fibrin hydrogels as a xenofree and rapidly degradable support for transplantation of retinal pigment epithelium monolayers," Acta. biomaterialia., 67:134-46, Feb. 2018.

(56) References Cited

OTHER PUBLICATIONS

Hou et al., "In vivo and in vitro study of suprachoroidal fibrin glue," Jpn. J. Opththalmol., 53(6):640-7, Nov. 2009.

Hu et al., "A Novel Approach for Subretinal Implantation of Ultrathin Substrates Containing Stem Cell-Derived Retinal Pigment Epithelium Monolayer," Ophthalmic Res., 48(4):186-91, Oct. 2012.

Idelson et al., "Directed Differentiation of Human Embryonic Stem Cells into Functional Retinal Pigment Epithelium Cells," Cell Stem Cell., 5(4):396-408, Oct. 2009.

Inoue et al., "iPS cells: a game changer for future medicine," The EMBO journal, 33(5):409-17, Mar. 2014.

International Preliminary Report on Patentability in International Application No. PCT/US2018/035992 dated Dec. 19, 2019, 9 pages.

International Search Report & Written Opinion in International Application No. PCT/US2018/035992 dated Aug. 8, 2018, 11 pages.

Jayaram et al., "Stem Cell and Encapsulated Drug Delivery to the Inner Retina using a Fibrin Polymer Spray System," 54(15):4686, Jun. 2013, (Abstract).

Johnson et al., "Autosomal Recessive Bestrophinopathy Is Not Associated With the Loss of Bestrophin-1 Anion Channel Function in a Patient With a Novel BEST1 Mutation,"Ophthalmol. Vis. Sci., 56(8):4619-30, Jul. 2015.

Johnson et al., "Disease modeling studies using induced pluripotent stem cells: are we using enough controls?" Regen Med., 899-903, Dec. 2017.

Kamao et al., "Characterization of Human Induced Pluripotent Stem Cell-Derived Retinal Pigment Epithelium Cell Sheets Aiming for Clinical Application," Stem Cell Rep., 2(2):205-18, Feb. 2014.

Koss et al., "Subretinal implantation of a monolayer of human embryonic stem cell-derived retinal pigment epithelium: a feasibility and safety study in Yucatan minipigs," Graefe's Archive for Clinical and Experimental Ophthalmology, 254(8):1553-65, Aug. 2016.

Lai et al., "Characterization of Cross-Linked Porous Gelatin Carriers and Their Interaction with Corneal Endothelium: Biopolymer Concentration Effect," PLoS One, 8(1):e54058, Jan. 2013.

Lam et al., "Improved human pluripotent stem cell attachment and spreading on xeno-free laminin-521-coated microcarriers results in efficient growth in agitated cultures," BioResearch open access, 4(1):242-57, Apr. 2015.

Lu et al., "A defined xeno-free and feeder-free culture system for the derivation, expansion and direct differentiation of transgene-free patient-specific induced pluripotent stem cells," Biomaterials, 35(9):2816-26, Mar. 2014.

Lu et al., "Mesh-supported submicron parylene-C membranes for culturing retinal pigment epithelial cells, " Biomed. Microdevices, 14(4):659-67, Aug. 2012.

Machin and Mackie, "Routine measurement of fibrinogen concentration," BMJ, 307(6909):882-883, Oct. 1993.

Mackie et al., "Haemostasis and Thrombosis Task Force of the British Committee for Standards in Haematology. Guidelines on fibrinogen assays," British journal of haematology, 121(3):396-404, May 2003.

Mandai et al., "Autologous Induced Stem-Cell-Derived Retinal Cells for Macular Degeneration," N. Eng. J. Med., 376(11):1038-46, Mar. 2017.

McHugh et al., "Porous Poly(ε-Caprolactone) Scaffolds for Retinal Pigment Epithelium Transplantation," Invest. Ophthalmol. Vis. Sci., 55(3):1754-62, Mar. 2014.

Medcell.med.yale.edu [online], "Cell Biology," Jan. 11, 2012 Retrieved from URL:<http://medcell.med.yale.edu/lectures/epithelial_structure.php> 5 pages, retrieved on Sep. 4, 2019.

Mishra et al., "Effect of prevascularization on in vivo vascularization of poly(propylene fumarate)/fibrin scaffolds," Biomaterials, 77:255-66, Jan. 2016.

Miyazaki et al., "Recombinant human laminin isoforms can support the undifferentiated growth of human embryonic stem cells," Biochemical and biophysical research communications, 375(1):27-32, Oct. 2008.

Moya et al., "Microfluidic device to culture 3D in vitro human capillary networks," Methods Mol. Biol., 1202:21-7, Jan. 2014.

Najafabadi et al., "Behavior of a spontaneously arising human retinal pigment epithelial cell line cultivated on thin alginate film," Journal of ophthalmic & vision research, 10(3):286-94, Jul. 2015.

Neofytou et al., "Hurdles to clinical translation of human induced pluripotent stem cells," The Journal of clinical investigation, 125(7):2551-7, Jul. 2015.

Oganesian et al., "A new model of retinal pigment epithelium transplantation with microspheres," Archives of Ophthalmology, 117(9):1192-200, Sep. 1999.

Peyman et al., "A Technique for Retinal Pigment Epithelium Transplantation for Age-Related Macular Degeneration Secondary to Extensive Subfoveal Scarring," Ophthalmic Surg., 22(2):102-8, Feb. 1991.

Pinnock et al., "Customizable engineered blood vessels using 3D printed inserts," Methods, 99:20-7, Apr. 2016.

Reyes et al., "Xeno-free and defined human embryonic stem cell-derived retinal pigment epithelial cells functionally integrate in a large-eyed preclinical model," Stem cell reports, 6(1):9-17, Jan. 2016.

Rezai et al., "Biodegradable polymer film as a source for formation of human fetal retinal pigment epithelium spheroids," Investigative ophthalmology & visual science, 40(6):1223-8, May 1999.

Roider et al., "Response of the Retinal Pigment Epithelium to Selective Photocoagulation," Arch Ophthalmol., 110(12):1786-92, 1992.

Roth, "Recombinant tissue plasminogen activator for the treatment of acute ischemic stroke," Bayl. Univ. Med. Cent. Proc., 24(3)257-9, 2011.

Rowe et al., "Influence of thrombin concentration on the mechanical and morphological properties of cell-seeded fibrin hydrogels," Acta Biomater., 3(1):59-67, Jan. 2007.

Rowland et al., "Differentiation of human pluripotent stem cells to retinal pigmented epithelium in defined conditions using purified extracellular matrix proteins," Journal of tissue engineering and regenerative medicine, 7(8):642-53, Aug. 2013.

Schwartz et al., "Embryonic stem cell trials for macular degeneration: a preliminary report," Lancet, 379(9817):713-20, Feb. 2012.

Schwartz et al., "Human embryonic stem cell-derived retinal pigment epithelium in patients with age-related macular degeneration and Stargardt's macular dystrophy: follow-up of two open-label phase 1/2 studies," Lancet., 385(9967):509-16, Feb. 2015.

Schwartz et al., "Subretinal Transplantation of Embryonic Stem Cell-Derived Retinal Pigment Epithelium for the Treatment of Macular Degeneration: An Assessment at 4 Years," Invest. Ophthalmol. Vis. Sci., 57(5):ORSFc1-9, Apr. 2016.

Singh et al., "Functional analysis of serially expanded human iPS cell-derived RPE cultures," Ophthalmol. Vis. Sci., 54(10):6767-78, Oct. 2013.

Sonoda et al., "A protocol for the culture and differentiation of highly polarized human retinal pigment epithelial cells," Nat. Protoc., 4(5):662-673, May 2009.

Stanzel et al., "Human RPE Stem Cells Grown into Polarized RPE Monolayers on a Polyester Matrix Are Maintained after Grafting into Rabbit Subretinal Space," Stem Cell Rep., 2(1):64-77, Jan. 2014.

Sun et al., "Protective Effects of Human iPS-Derived Retinal Pigmented Epithelial Cells in Comparison With Human Mesenchymal Stromal Cells and Human Neural Stem Cells on the Degenerating Retina in rd1 Mice," Stem Cells, 33(5):1543-1553, May 2015.

Tababat-Khani et al., "Photocoagulation of human retinal pigment epithelium in vitro: unravelling the effects on ARPE-19 by transcriptomics and proteomics," Acta Ophthalmol., 93(4):348-54, Jun. 2015.

Takahashi et al., "Induction of pluripotent stem cells from adult human fibroblasts by defined factors," Cell, 131(5):861-72, Nov. 2007.

(56) References Cited

OTHER PUBLICATIONS

Uehara et al., "Effect of Fibrin Formulation on Initial Strength of Tendon Repair and Migration of Bone Marrow Stromal Cells in Vitro," J. Bone Joint Surg. Am., 97(21):1792-8, Nov. 2015.

Undas and Ariens, "Fibrin clot structure and function: a role in the pathophysiology of arterial and venous thromboembolic diseases," Arterioscler. Thromb. Vasc. Biol., 31:e88-e99, Dec. 2011.

Unger et al., "Good manufacturing practice and clinical-grade human embryonic stem cell lines," Human molecular genetics, 17(R1):R48-53, Apr. 2008.

Xiang et al., "A novel Bruch's membrane-mimetic electrospun substrate scaffold for human retinal pigment epithelium cells," Biomaterials, 35(37):9777-88, Dec. 2014.

Yamanaka, "The winding road to pluripotency (Nobel Lecture)," Angewandte Chemie International Edition, 52(52):13900-9, Dec. 2013.

Ye et al., "Primer-BLAST: A tool to design target-specific primers for polymerase chain reaction," BMC Bioinformatics, 13(1):134, Jun. 2012.

Zarbin, "Cell-Based Therapy for Degenerative Retinal Disease," Trends Mol. Med., 22(2):P115-34., Feb. 2016.

U.S. Appl. No. 16/467,681, filed Jun. 7, 2019, Alan D. Marmorstein.

Bhatt et al., "Experimental transplantation of human retinal pigment epithelial cells on collagen substrates," Am. J. Ophthalmology, Feb. 15, 1994, 117(2):214-221.

CA.gov [online], "Stem Cell Experts Discuss the Ethical Implications of Translating iPSCs to the Clinic," Sep. 27, 2016, retrieved on Apr. 22, 2022, retrieved from URL<https://blog.cirm.ca.gov/2016/09/27/stem-cell-experts-discuss-the-ethical-implications-of-translating-ipscs-to-the-clinic/>, 7 pages.

Collet et al., "Influence of fibrin network conformation and fibrin fiber diameter on fibrinolysis speed: dynamic and structural approaches by confocal microscopy," Arterioscler. Thromb. Vasc. Biology, May 2000, 20(5):1354-1361.

Cyranoski, "Japanese woman is first recipient of next-generation stem cells," Nature, Sep. 12, 2014, 2 pages.

Gabrielian et al., "Growth of human fetal retinal pigment epithelium as microspheres," Graefes Arch. Clin. Exp. Ophthalmology, Feb. 1999, 237(3):241-248.

Giordano et al., "Retinal pigment epithelium cells cultured on synthetic biodegradable polymers," J. Biomed. Mater. Research, Jan. 1997, 34(1):87-93.

RegMedNet.com [online], "Cell therapy commercialization: GMP and Scalability," Sep. 26, 2017, retrieved on Apr. 22, 2022, retrieved from URL<https://www.regmednet.com/cell-therapy-commercialization-gmp-and-scalability/>, 7 pages.

Singh. Sukhjit; et al; "Natural and artificial substrates for retinal pigment epithelial monolayer transplantation" Biomaterials, 22, 3337-3343, 2001 (Year: 2001).

Taylor et al., "Controlled release of neurotrophin-3 from fibrin gels for spinal cord injury," J. Control. Release, Aug. 11, 2004, 98(2):281-294.

Undas et al., "A Role in the Pathophysiology of Arterial and Venous Thromboembolic Diseases," Arterioscler. Thromb. Vasc. Biol., 31:e88-99, Aug. 2011.

Warnke et al., "Primordium of an artificial Bruch's membrane made of nanofibers for engineering of retinal pigment epithelium cell monolayers," Acta Biomaterialia, Dec. 2013, 9(12):9414-9422.

U.S. Appl. No. 17/428,703, filed Aug. 5, 2021, Jarel K. Gandhi, Published as U.S. Patent Application Publication No. 2022/0000664.

German et al., "Retinal pigment epithelial cells promote spatial reorganization and differentiation of retinal photoreceptors," J. Neurosci. Research, 86(16):3503-3514, Dec. 2008.

Slaughter et al., "Antifibrinolytic drugs and perioperative hemostasis," Am. J. Hematology, 56(1):32-36, Sep. 1997.

Yaji, Naoko; et al; "Transplantation of tissue-engineered retinal pigment epithelial cell sheets in a rabbit model" Biomaterials, 30, 797-803, 2009 (Year: 2009).

Yunping, "[Comparison of growth of human retinal pigment epithelial cell on two prosthetic replacements of Bruch's membrane]," Dissertation, Central South University, 2010, 112 pages (with English Abstract).

Chen et al., "Approach discussion of the differentiation of stem cells induced to retinal pigment epithelial cells," Int. Eye Science, Oct. 8, 2020, 20(10):1722-1725 (with English abstract).

Gandhi et al., "Human Fibrinogen for Maintenance and Differentiation of Induced Pluripotent Stem Cells in Two Dimensions and Three Dimensions," Stem Cells Transl. Medicine, Feb. 15, 2019, 8(6):512-521.

Ji et al., "[Research progress on the differentiation of human induced pluripotent stem cells into retinal pigment epithelial cells and its application in clinical treatment]," China Med. Biotechnology, Aug. 10, 2017, 12(4):356-359, 368 (with English Abstract).

Yang et al., "Induced Pluripotent Stem Cells and Outer Retinal Disease," Stem Cells International, Jan. 15, 2016, 2016:2850873, 6 pages.

Zeng, "[Comparison of the biological characteristics of 2D and 3D induced human embryonic stem cell-derived retinal pigment epithelium]," Thesis, The Third Military Medical University, May 2016, 65 pages (with English Abstract).

Dietrich et al., "Fibrin-based tissue engineering: comparison of different methods of autologous fibrinogen isolation," Tissue Eng. Part C Methods, Mar. 2013, 19(3):216-226.

Gray et al., "Aα and Bβ chains of fibrinogen stimulate proliferation of human fibroblasts," J. Cell. Sci., Feb. 1993, 104(2):409-413.

Marmorstein et al., "Mutant Best1 Expression and Impaired Phagocytosis in an iPSC Model of Autosomal Recessive Bestrophinopathy," Sci. Rep., Mar. 2018, 8(1):4487.

Orlova et al., "Generation, expansion and functional analysis of endothelial cells and pericytes derived from human pluripotent stem cells," Nat. Protoc., 2014, 9(6):1514-1531.

Sparrow et al., "A protocol for the preparation of cryoprecipitate and cryodepleted plasma," Methods Mol. Biol., 2011, 728:259-265.

Spectre et al., "Platelets selectively enhance lymphocyte adhesion on subendothelial matrix under arterial flow conditions," Thromb. Haemost., Aug. 2012, 108(2):328-337.

Sporn et al., "Cell Proliferation on Fibrin: Modulation by Fibrinopeptide Cleavage," Blood, Sep. 1995, 86(5):1802-1810.

Srikanth et al., "Genomic DISC1 Disruption in hiPSCs Alters Wnt Signaling and Neural Cell Fate," Cell Rep., Sep. 2015, 12(9):1414-1429.

Underwood et al., "Effects of base material, plasma proteins and FGF2 on endothelial cell adhesion and growth," J. Biomater. Sci. Polym. Ed., 2002, 13(8):845-862.

Zeng et al., "Specification of region-specific neurons including forebrain glutamatergic neurons from human induced pluripotent stem cells," PLoS One, Jul. 2010, 5(7):e11853.

* cited by examiner

Pluripotency (Nanog+Tra1-60)     (Oct4+SSea4)

Differentiation

Mesoderm          Endoderm          Ectoderm
(CD31+NCAM)    (FoxA2+Sox17)    (Nestin+Pax6)

2 mg/mL Fibrinogen
9 U/mL Thrombin

FIG. 33A

WiCell Clone 4

Pluripotency Nanog-Tra1-60

Pluripotency Oct4-SSea4

CD31 staining

UEA-Lectin Staining

METHODS AND MATERIALS FOR CULTURING, PROLIFERATING, AND DIFFERENTIATING STEM CELLS

CROSS-REFERENCE TO RELATED APPLICATIONS

This application is a National Stage application under 35 U.S.C. § 371 of International Application No. PCT/US2018/035992, having an International Filing Date of Jun. 5, 2018, which claims priority to U.S. Application Serial Nos. 62/634,580, filed on Feb. 23, 2018 and 62/515,286, filed on Jun. 5, 2017. The disclosures of the prior applications are considered part of the disclosure of this application, and are incorporated in their entirety into this application.

BACKGROUND

1. Technical Field

This document relates to induced pluripotent stem cells (iPSCs) and retinal pigment epithelium. For example, this document relates to methods and materials for culturing, proliferating, and differentiating stem cells (e.g., iPSCs). This document also relates to methods and materials for making retinal pigment epithelium from stem cells (e.g., iPSCs).

2. Background Information

One example disease target of iPSC-based regenerative medicine is Macular Degeneration. Macular degeneration is a disorder of the retinal pigment epithelium (RPE). Genetic macular degenerations, including the bestrophinopathies, occur due to protein mutations involved in RPE function. The bestrophinopathies, most commonly Best's disease, arise from a mutation in the Best1 gene, causing RPE dysfunction in its role to support the photoreceptors, and leads to eventual photoreceptor death. The prevalence has previously been reported as 1 in 16,000-21,500 (Dalvin et al., *Ophthalmic Genet.*, Epub:1-5 (2016)). While the genetically-caused macular degenerations are rare, age-related macular degeneration (AMD) is the leading cause of blindness in the first world. It is estimated to account for 5 million cases in 2050. AMD is a more complex disease of immune and vascular function that directly affects the RPE function.

RPE replacement as a treatment for macular degeneration has been a popular focus in recent history. Modern advances in stem cell technologies have made embryonic stem cells (ESCs) and iPSCs attractive candidates for transplantation. Multiple reports show the ability to differentiate both stem cell sources towards an RPE lineage using various differentiation medias (Sonoda et al., *Nat. Protoc.,* 4:662-673 (2009); Johnson et al., *Opthalmology Vis. Sci.,* 56:4619 (2015); Brandl et al., NeuroMolecular Med., 16:551-564 (2014); Idelson et al., *Cell Stem Cell.,* 5:396-408 (2009); Carr et al., *Mol. Vis.,* 15:283-295 (2009)). Both ESC-RPE and iPSC-RPE have been shown to exhibit normal RPE function, including cell markers, phagocytosis, and pigmentation (Singh et al., *Ophthalmol. Vis. Sci.,* 54:6767-6778 (2013)).

SUMMARY

This document relates to iPSCs and RPE. For example, this document provides compositions containing RPE as well as methods and materials for culturing, proliferating, and differentiating stem cells (e.g., iPSCs). For example, this document provides compositions containing RPE as well as methods and materials for making RPE from, for example, stem cells (e.g., iPSCs). As described herein, human fibrinogen can be used as a xeno-free (non-xenogeneic), cGMP (Current Good Manufacturing Practice) compatible cell attachment substrate for the culturing, differentiation, and manufacturing of iPSC-RPE for use in humans. In some cases, fibrin (e.g., a fibrin hydrogel) can be used in place of fibrinogen to carry out the methods and materials provided herein.

Fibrinogen is the precursor polypeptide to fibrin, a protein responsible for clot formation in blood. Fibrinogen is a soluble, 340 kDa polypeptide found at about 200 to 400 mg/dL in human blood. When the clotting cascade is activated, the active enzyme thrombin, cleaves two fibrinopeptides from fibrinogen to give the fibrin monomer. Fibrin monomers have a very high affinity to each other and polymerize to form an insoluble, 3D mesh hydrogel. While not an extracellular matrix protein, fibrinogen has been shown to promote attachment of primary platelets and endothelial cells for culture as described elsewhere (Spectre et al., *Thromb Haemost.,* 108: 328-37 (2012); Underwood et al., *J Biomater Sci Polym Ed.,* 13: 845-62 (2002)). Similarly, fibrinogen as a 3D mesh hydrogel has been used for tissue engineering applications. Fibrin gels show highly attractive properties, including 3-dimension (3D) mesh formation, non-xenogeneic origin, biocompatibility, and biodegradation. For example, fibrin is used in angiogenesis and vascularization assays, with cells like human umbilical vein endothelial cells (HUVEC) (Mishra et al. *Biomaterials,* 77:255-66 (2016)).

In general, one aspect of this document features a method for making a retinal pigment epithelium monolayer. The method includes, or consists essentially of, culturing stem cells in a container having a surface coated with fibrinogen, where the surface was coated with greater than 3 µg/mL of fibrinogen, where the cells are in contact with the fibrinogen, and where the cells form a retinal pigment epithelium monolayer. The stem cells can be induced pluripotent stem cells (e.g., human induced pluripotent stem cells). The container can be a culture dish (e.g., a culture flask). The surface can include polystyrene, polycarbonate, mixed cellulose, PTFE, PDMS, PET, glass, a poly-L-lysine coating, or a combination thereof. The fibrinogen can be human fibrinogen. The surface can be coated with from about 3 to about 250 µg/mL of fibrinogen. The surface can be coated with from about 15 to about 250 µg/mL of fibrinogen. The surface can be coated with from about 25 to about 250 µg/mL of fibrinogen. The surface can be coated with from about 50 to about 250 µg/mL of fibrinogen. The surface can be coated with from about 75 to about 250 µg/mL of fibrinogen. The surface can be coated with said fibrinogen for about 1 to about 48 hours. The method can include culturing the cells for from about 7 days to about 90 days to form the retinal pigment epithelium monolayer. The method can be xeno-free.

In another aspect, this document features a retinal implant including a retinal pigment epithelium monolayer, where the retinal pigment epithelium monolayer was produced according to the methods described herein.

In another aspect, this document features a method for treating an eye condition. The method includes, or consists essentially of, implanting a retinal implant including a retinal pigment epithelium monolayer into an eye of a mammal, where the retinal pigment epithelium monolayer was produced according to the methods described herein. The eye condition can be macular degeneration. The mammal can be a human.

In another aspect, this document features a method for maintaining stem cells in culture. The method includes, or consists essentially of, culturing the stem cells in a container having a surface coated with fibrinogen, wherein the surface was coated with greater than 250 µg/mL of fibrinogen, wherein the stem cells are in contact with the fibrinogen, and wherein the stem cells maintain the ability to differentiate into cells of ectodermal, endodermal, and mesodermal origin after at least one passage. The stem cells can be induced pluripotent stem cells. The stem cells can be human induced pluripotent stem cells. The container can be a culture dish. The container can be a culture flask. The surface can comprise polystyrene, polycarbonate, mixed cellulose, PTFE, PDMS, PET, glass, a poly-L-lysine coating, or a combination thereof. The fibrinogen can be human fibrinogen. The surface can be a surface that was coated with from about 250 to about 5000 µg/mL of fibrinogen. The surface can be a surface that was coated with from about 300 to about 900 µg/mL of fibrinogen. The surface can be a surface that was coated with from about 350 to about 750 µg/mL of fibrinogen. The surface can be a surface that was coated with from about 400 to about 600 µg/mL of fibrinogen. The surface can be a surface that was coated with from about 450 to about 550 µg/mL of fibrinogen. The surface can be a surface that was coated with the fibrinogen for about 1 to about 48 hours. The method can comprise culturing the cells for from about 2 days to about 90 days. The method can be xeno-free. The stem cells can form endothelial cells. The stem cells can form epithelial cells (e.g., RPE cells). The fibrinogen can be obtained autologously.

In another aspect, this document features a method for maintaining stem cells in culture. The method includes, or consists essentially of, culturing the stem cells in a container having a surface coated with fibrinogen, wherein the surface was coated with greater than 3 µg/mL of fibrinogen, wherein the stem cells are in contact with the fibrinogen, and wherein the stem cells maintain the ability to differentiate into cells of ectodermal, endodermal, and mesodermal origin after at least one passage. The stem cells can be induced pluripotent stem cells. The stem cells can be human induced pluripotent stem cells. The container can be a culture dish. The container can be a culture flask. The surface can comprise polystyrene, polycarbonate, mixed cellulose, PTFE, PDMS, PET, glass, a poly-L-lysine coating, or a combination thereof. The fibrinogen can be human fibrinogen. The surface can be a surface coated with from about 100 to about 5000 µg/mL of fibrinogen. The surface can be a surface coated with from about 300 to about 900 µg/mL of fibrinogen. The surface can be a surface coated with from about 100 to about 250 µg/mL of fibrinogen. The surface can be a surface coated with from about 350 to about 750 µg/mL of fibrinogen. The surface can be a surface coated with from about 400 to about 600 µg/mL of fibrinogen. The surface can be a surface coated with from about 450 to about 550 µg/mL of fibrinogen. The surface can be a surface coated with the fibrinogen for about 1 to about 48 hours. The method can comprise culturing the cells for from about 2 days to about 90 days. The method can be xeno-free. The stem cells can form endothelial cells. The stem cells can form epithelial cells (e.g., RPE cells). The fibrinogen can be obtained autologously.

In another aspect, this document features a method for maintaining stem cells in culture. The method includes, or consists essentially of, culturing the stem cells in a container having a surface coated with fibrin hydrogel, wherein the fibrin hydrogel was formed with greater than 0.5 mg/mL of fibrinogen, wherein the stem cells are in contact with the fibrin hydrogel, and wherein the stem cells maintain the ability to differentiate into cells of ectodermal, endodermal, and mesodermal origin after at least one passage. The stem cells can be induced pluripotent stem cells. The stem cells can be human induced pluripotent stem cells. The container can be a culture dish. The container can be a culture flask. The surface can comprise polystyrene, polycarbonate, mixed cellulose, PTFE, PDMS, PET, glass, poly-L-lysine coating, or a combination thereof. The fibrinogen can be human fibrinogen. The fibrin hydrogel can be a fibrin hydrogel formed with fibrinogen concentration from about 0.5 mg/mL to about 80 mg/mL. The fibrin hydrogel can be a fibrin hydrogel formed with a fibrinogen concentration from about 10 mg/mL to about 50 mg/mL. The fibrin hydrogel can be a fibrin hydrogel formed with a fibrinogen concentration from about 25 mg/mL to about 35 mg/mL. The fibrin hydrogel can be a fibrin hydrogel polymerized using 0.5-500 U/mL of thrombin. The fibrin hydrogel can comprise an anti-fibrinolytic agent. The anti-fibrinolytic agent can be tranexamic acid at a concentration from about 0.5 mg/mL to about 50 mg/mL. The anti-fibrinolytic agent can be aprotinin at a concentration from about 0.1 U/mL to about 40 U/mL.

In another aspect, this document features a method for making endothelial cells. The method includes, or consists essentially of, culturing stem cells in a container having a surface coated with fibrinogen, wherein the surface was coated with greater than 3 µg/mL of fibrinogen, wherein the stem cells are in contact with the fibrinogen, and wherein the stem cells form endothelial cells. The stem cells can be induced pluripotent stem cells. The stem cells can be human induced pluripotent stem cells. The container can be a culture dish. The container can be a culture flask. The surface can comprise polystyrene, polycarbonate, mixed cellulose, PTFE, PDMS, PET, glass, poly-L-lysine coating, or a combination thereof. The fibrinogen can be human fibrinogen. The surface can be a surface coated with from about 3 to about 250 µg/mL of fibrinogen. The surface can be a surface coated with from about 15 to about 250 µg/mL of fibrinogen. The surface can be a surface coated with from about 25 to about 250 µg/mL of fibrinogen. The surface can be a surface coated with from about 50 to about 250 µg/mL of fibrinogen. The surface can be a surface coated with from about 75 to about 250 µg/mL of fibrinogen. The surface can be a surface coated with the fibrinogen for about 1 to about 48 hours. The method can comprise culturing the cells for from about 7 days to about 90 days to form endothelial cells. The method can be xeno-free.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 33A-B contain photographs of pluripotency staining of iPSCs grown on various substrates. A) immunofluorescent staining of pluripotency factors Oct4, Ssea4, Nanog, and Tra1-60 in iPSCs cultured on Evicel® (cryoprecipitated fibrinogen), ethanol precipitated fibrinogen (EPF), and Geltrex™ as a positive control. B) FACS analysis of the pluripotency factors amongst the three groups of culture coating.

DETAILED DESCRIPTION

Figure 1:
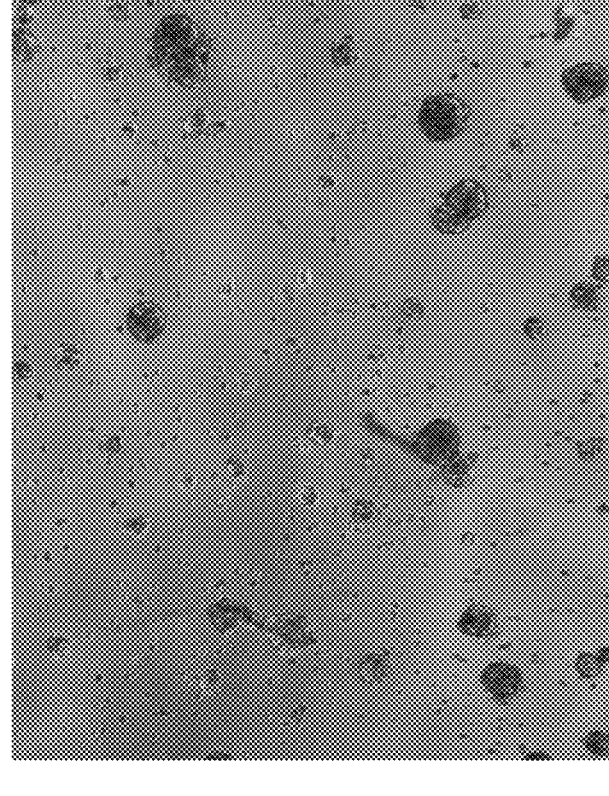
FIG. 1 contains photographs iPSC-RPE cells after being cultured in differentiation medium for seven days. $1\times10^5$ cells were originally plated onto 96-well plates coated with 0.1 µg/mL of fibrinogen. The RPE cells formed organoids and were unattached. No monolayer was observed.
Figure 1:
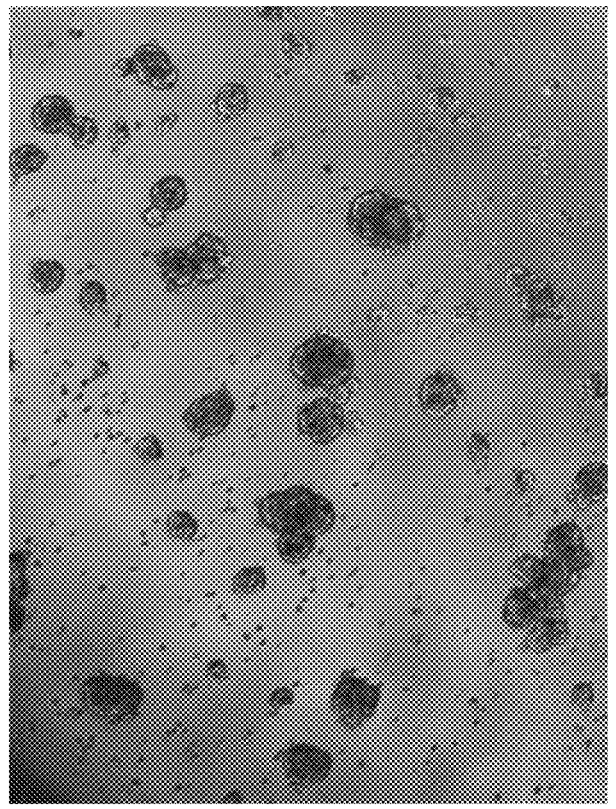

This document relates to iPSCs and RPE. In some cases, this document provides methods and materials for culturing, proliferating, and differentiating stem cells (e.g., iPSCs). For example, this document provides methods and materials for using fibrinogen coatings to create a surface for culturing, proliferating, and differentiating stem cells. In some cases, stem cells can be expanded and differentiated (e.g., into RPE). In some cases, stem cells can be expanded without differentiation. In some cases, this document provides compositions containing RPE as well as methods and materials for culturing, proliferating, and differentiating stem cells (e.g., iPSCs) into RPE cells. For example, this document provides methods and materials for using fibrinogen coatings to create a surface for stem cells to form RPE monolayers. As described herein, fibrinogen can be used as a substrate for RPE monolayer formation in methods that are xeno-free (non-xenogeneic). For example, all the animal derived components used to make a human RPE monolayer can be derived from humans. In addition, an RPE monolayer formed as described herein can be used to make an RPE implant. RPE implants can be used to treat eye conditions such as retinal degeneration or macular degeneration. In some cases, an RPE monolayer or RPE implant provided herein can be designed such that the RPE is a flat, wrinkle-free monolayer.

Any appropriate method can be used to produce fibrinogen for making RPE monolayers. For example, fibrinogen can be isolated from blood products (e.g., isolated from human blood) or can be produced using recombinant technology. In some cases, fibrinogen can be obtained commercially from, for example, Baxter International (Tisseel™), Ethicon Inc (Evicel®), or CSL Behring (RiaSTAP®; a fibrinogen concentrate). For example, fibrinogen can be formed as a hydrogel. In some cases, a fibrinogen hydrogel can be formed by mixing fibrinogen (e.g., a fibrinogen solution) with thrombin (e.g., a thrombin solution). In some cases, a fibrinogen hydrogel also can include an anti-fibrinolytic agent (e.g., aprotinin and tranexamic acid).

Any appropriate method can be used to coat a surface with fibrinogen. For example, a surface of a cell culture container can be coated with fibrinogen by exposing the surface to a solution containing fibrinogen for a period of time. Any appropriate concentration of fibrinogen can be used to coat a surface with fibrinogen. For example, a solution containing from about 3 μg/mL to about 1000 μg/mL (e.g., from about 5 μg/mL to about 500 μg/mL, from about 15 μg/mL to about 500 μg/mL, from about 25 μg/mL to about 500 μg/mL, from about 5 μg/mL to about 250 μg/mL, from about 5 μg/mL to about 150 μg/mL, from about 5 μg/mL to about 100 μg/mL, from about 15 μg/mL to about 100 μg/mL, from about 25 μg/mL to about 100 μg/mL, or from about 50 μg/mL to about 100 μg/mL) of fibrinogen can be used to coat a surface with fibrinogen. In some cases, the solution containing fibrinogen can be exposed to the surface being coated for from about 1 hour to about 72 hours (e.g., 2 hours to about 72 hours, 4 hours to about 72 hours, 6 hours to about 72 hours, 2 hours to about 48 hours, 2 hours to about 24 hours, 6 hours to about 48 hours, or 6 hours to about 24 hours). In some cases, spray-coating, sputter-coating, spin-coating, or dip-coating techniques can be used to coat a surface with fibrinogen.

For example, a surface of a cell culture container can be coated with fibrinogen by forming a fibrin hydrogel on the surface. Any appropriate concentration of fibrinogen hydrogel can be used to coat a surface with fibrinogen. In some cases, a fibrin hydrogel can be formed by mixing a fibrinogen containing solution with a thrombin containing solution. For example, a solution containing from about 1 mg/mL to about 100 mg/mL (e.g., from about 1 mg/mL to about 80 mg/mL, from about 1 mg/mL to about 75 mg/mL, from about 1 mg/mL to about 60 mg/mL, from about 1 mg/mL to about 50 mg/mL, from about 1 mg/mL to about 35 mg/mL, from about 1 mg/mL to about 25 mg/mL, from about 1 mg/mL to about 10 mg/mL, from about 15 mg/mL to about 100 mg/mL, from about 25 mg/mL to about 100 mg/mL, from about 40 mg/mL to about 100 mg/mL, from about 50 mg/mL to about 100 mg/mL, from about 60 mg/mL to about 100 mg/mL, from about 70 mg/mL to about 100 mg/mL, from about 85 mg/mL to about 100 mg/mL, from about 10 mg/mL to about 85 mg/mL, from about 25 mg/mL to about 75 mg/mL, from about 40 mg/mL to about 60 mg/mL, from about 20 mg/mL to about 40 mg/mL, from about 30 mg/mL to about 50 mg/mL or from about 60 mg/mL to about 80 mg/mL) fibrinogen can be mixed with a solution containing from about 1 U/mL to about 1,000 U/mL (e.g., from about 15 U/mL to about 1,000 U/mL, from about 25 U/mL to about 1,000 U/mL, from about 50 U/mL to about 1,000 U/mL, from about 100 U/mL to about 1,000 U/mL, from about 250 U/mL to about 1,000 U/mL, from about 500 U/mL to about 1,000 U/mL, from about 750 U/mL to about 1,000 U/mL, from about 900 U/mL to about 1,000 U/mL, from about 1 U/mL to about 750 U/mL, from about 1 U/mL to about 500 U/mL, from about 1 U/mL to about 250 U/mL, from about 1 U/mL to about 100 U/mL, from about 1 U/mL to about 75 U/mL, from about 1 U/mL to about 50 U/mL, from about 50 U/mL to about 800 U/mL, from about 100 U/mL to about 600 U/mL, from about 200 U/mL to about 500 U/mL, from about 300 U/mL to about 400 U/mL, from about 100 U/mL to about 300 U/mL, or from about 500 U/mL to about 750 U/mL) thrombin. For example, a solution containing fibrinogen can be mixed with a solution containing thrombin at ratio of from about 1:0.25 to about 1:200 (e.g., from about 1:0.25 to about 1:150, from about 1:0.25 to about 1:100, from about 1:0.25 to about 1:75, from about 1:0.25 to about 1:50, from about 1:0.25 to about 1:25, from about 1:0.25 to about 1:10, from about 1:0.25 to about 1:5, from about 1:0.25 to about 1:1, from about 1:0.25 to about 1:0.5, from about 1:0.5 to about 1:200, from about 1:1 to about 1:200, from about 1:10 to about 1:200, from about 1:25 to about 1:200, from about 1:50 to about 1:200, from about 1:75 to about 1:200, from about 1:100 to about 1:200, from about 1:150 to about 1:200, from about 1:175 to about 1:200, from about 1:1 to about 1:150, from about 1:25 to about 1:100, from about 1:50 to about 1:100, from about 1:25 to about 1:75, or from about 1:100 to about 1:150). In some cases, a fibrin hydrogel formed on a surface can be re-hydrated. For example, a fibrin hydrogel can be formed on the surface being coated for from about 10 minutes to about 24 hours (e.g., from about 30 minutes to about 24 hours, from about 1 hour to about 24 hours, from about 2 hours to about 24 hours, from about 6 hours to about 24 hours, from about 12 hours to about 24 hours, or from about 18 hours to about 24 hours) prior to re-hydration. In some cases, a solution containing fibrinogen and/or a solution containing thrombin also can include an anti-fibrinolytic agent (e.g., aprotinin and tranexamic acid). In some cases, spray-coating, sputter-coating, spin-coating, or dip-coating techniques can be used to coat a surface with a solution containing fibrinogen and a solution containing thrombin.

In some cases, a surface of a cell culture container also can be coated with one or more additional molecules such as extracellular matrix proteins. For example, collagen, vitronectin, fibronectin, gelatin, elastin, laminin, or any combinations thereof can be used to coat a surface of a cell culture container.

Once a surface of a cell culture container is coated with fibrinogen as described herein, stem cells can be placed in contact with the fibrinogen and cultured. Any appropriate stem cell can be used. For example, embryonic stem cells (e.g., human embryonic stem cells), induced pluripotent stem cells (e.g., human induced pluripotent stem cells), or adult stem cells (e.g., mesenchymal stem cells and adipose-derived stem cells) can be used. Stem cells can be placed in contact with the fibrinogen as single cells (e.g., a suspension of single cells), as colonies, or as spheroids. In some cases, stem cells can be passaged onto a fresh surface of a cell culture container coated with fibrinogen as described herein. For example, stem cells can be lifted off a surface of a cell culture container and replated onto a fresh cell culture container surface coated with fibrinogen, and optionally one or more additional molecules (e.g., collagen, vitronectin, fibronectin, gelatin, elastin, or a combination thereof), as described herein. Passaging stem cells can be effective to increase the number of stem cells (e.g., iPSCs). For example, passaging stem cells can be effective to increase the number of stem cells that can be differentiated (e.g., into RPE cells capable of forming an RPE monolayer). In some cases, when a stem cell (e.g., an iPSC) is differentiated, the stem cell can be differentiated into any appropriate type of cell. A stem cell can be differentiated into a cell of any germ layer (e.g., an endodermal cell, a mesodermal cell, or an ectodermal cell). A stem cell can be differentiated into any appropriate type of cell. For example, a stem cell can be differentiated into vascular endothelium. For example, a stem cell can be differentiated into epithelial cells (e.g., RPE cells). Any appropriate differentiation protocol can be used to differentiate the stem cells (e.g., into RPE cells capable of forming an RPE monolayer). Examples of differentiation protocols that can be used to differentiate stem cells (e.g., iPSCs) into RPE cells capable of forming an RPE monolayer include, without limitation, those techniques described elsewhere (see, e.g., Sonoda et al., *Nat. Protoc.*, 4:662-673 (2009); Johnson et al., *Opthalmology Vis. Sci.*, 56:4619 (2015); Brandl et al., *NeuroMolecular Med.*, 16:551-564 (2014); Idelson et al., *Cell Stem Cell.*, 5:396-408 (2009); and Carr et al., *Mol. Vis.*, 15:283-295 (2009)). Once an RPE monolayer is formed, it can be used to create a RPE implant for treating an eye condition.

This document also provides methods for using an RPE monolayer or RPE implant provided herein to treat eye conditions such as high myopia, angioid streaks, and macular degeneration. Some of the diseases that classify as macular degeneration and that can be treated as described herein include, without limitation, age-related macular degeneration (AMD), central geographic atrophy, bestrophinopathies, Leber's congenital amaurosis, choroideremia, Gyrate atrophy, Sorsby's macular dystrophy, mitochondrialinherited diabetes and deafness (MIDD), chloroquine-associated retinopathy, malattia leventinese, North Carolina dystrophy, hyperomithinemia, central serous chorioretinopathy, adult-onset foveomacular dystrophy, and Stargardt's disease. For example, a mammal (e.g., a human) can be prepared for eye surgery, and a sub-retinal detachment can be created to expose a damaged RPE region. At this point, an implantation device can be used to deliver an RPE implant provided herein onto the region of interest. In some cases, a cannula can be used to gain access to the eye. In some cases, an air-phase bubble may be used to push the RPE implant into place. A laser tool (e.g., a laser tool used for diabetic retinopathy) can be used to tack the implant down via laser photocoagulation, preventing it from slipping. At this point, an implantation device can be used to deliver a second RPE implant provided herein onto the region of interest within an eye. The second implant can be placed adjacent to the first, preferably through the original incision or cannula. A laser tool can be used to tack the second implant down, preventing it from slipping. An implantation device can be used to deliver a third RPE implant provided herein onto the region of interest within an eye. The third implant can be placed adjacent to the second, preferably through the original incision or cannula. A laser tool can be used to tack the third implant down, preventing it from slipping. While this section describes implanting three RPE implants, any appropriate number can be used to cover the area to be treated. For example, one, two, three, four, five, six, or more RPE monolayer/fibrin implants provided herein can be implanted within a single eye being treated. In general, this modular tiling approach can allow a clinician to personalize the implants to the patient's need, is scalable to large areas, is applicable to any region of the retina, and reduces the number of incisions required.

The invention will be further described in the following examples, which do not limit the scope of the invention described in the claims.

EXAMPLES

Example 1—Using Fibrinogen to Form iPSC-RPE Monolayers

Chemicals

Fibrinogen was obtained from three sources: as Evicel® from Ethicon (60 mg/mL), as Tisseel™ from Baxter (95 mg/mL), and as research grade material from Sigma-Aldrich® (57 mg/mL) and Millipore® (44 mg/mL). Final working concentrations were formed in a range of concentrations, 0-1 mg/mL using PBS.

Coating Protocol

Matrigel® coated plates were utilized as positive controls as described elsewhere (Johnson et al., *Investig. Opthalmology Vis. Sci.*, 56:4619 (2015)). Varying concentrations of fibrinogen were prepared by diluting stock fibrinogen into PBS and plated onto various sized wells for 1 to 24 hours at 4 to 37° C. After subsequent washing with PBS, the cells were plated at various concentrations ($0.1×10^6$ to $1×10^6$ cells/cm$^2$) and incubated at 5% $CO_2$ at 37° C. Cells were observed for attachment and viability over time.

Cells

Partially differentiated iPSC-RPE at passage 1 or 2 were obtained from LAgen Laboratories LLC (Rochester, MN). The initial differentiation process was performed as described elsewhere with modification (Johnson et al., *Investig. Opthalmology Vis. Sci.*, 56:4619 (2015)). Cells were lifted off the plate by initially digesting with collagenase, then creating a cell suspension with accumax, and were replated at various concentrations ($0.1 \times 10^6$ to $1 \times 10^6$ cells/cm$^2$) on fibrinogen or Matrigel® coated tissue culture polystyrene (TCPS) or polycarbonate. Cells were cultured with differentiation media as described elsewhere (Johnson et al., *Investig. Opthalmology Vis. Sci.*, 56:4619 (2015)).

Differentiation

Brightfield images of the plated cells were taken to assess morphology of the cells at different times during the differentiation process. After 2 weeks of culture, complete differentiation of RPE cells was assessed by western blot analysis and growth factor secretion via an ELISA at various time points.

Western blot analysis was accomplished using a Protein-Simple® Wes™ instrument (ProteinSimple®, San Jose, CA) for specific RPE markers, including RPE65, Best1, CRALBP, MERTK, and β-actin. Growth factor secretion was quantified by ELISA. After 6-12 weeks of culture, 24 to 48 hour spent media was collected and frozen at −20° C. prior to testing. ELISA was performed for VEGF and PEDF using commercial kits (DuoLISA, RND Systems) with the collected media.

Results

Figure 2:
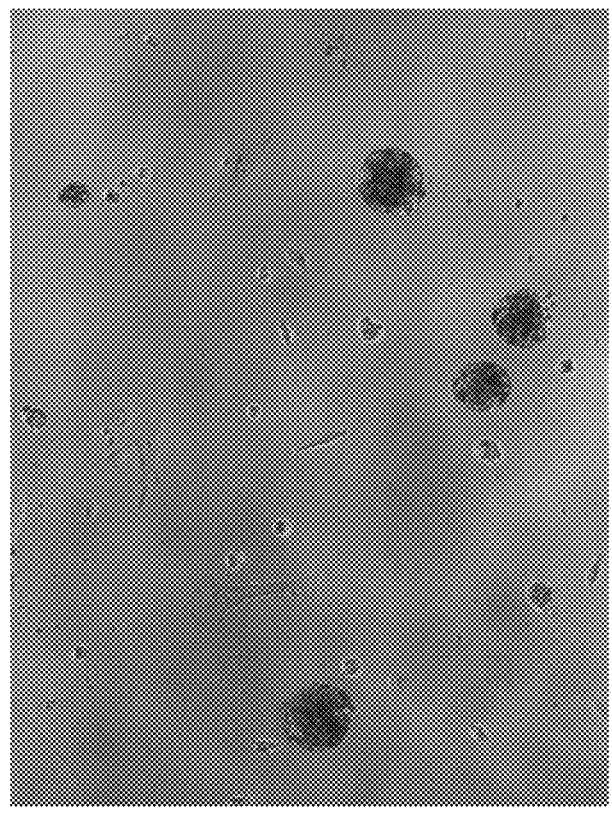
FIG. 2 contains photographs iPSC-RPE cells after being cultured in differentiation medium for seven days. $1 \times 10^5$ cells were originally plated onto 96-well plates coated with 0.5 µg/mL of fibrinogen. The RPE cells formed organoids and were unattached. No monolayer was observed.
Figure 2:
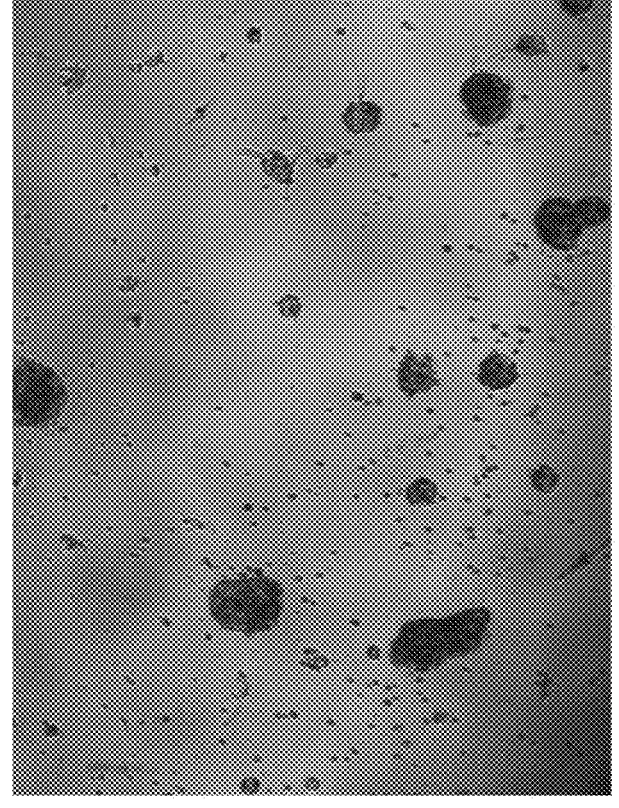
Figure 3:
FIG. 3 contains photographs iPSC-RPE cells after being cultured in differentiation medium for seven days. $1 \times 10^5$ cells were originally plated onto 96-well plates coated with 1 µg/mL of fibrinogen. The RPE cells formed a patchy monolayer that was less than about 70 percent confluent.
Figure 3:
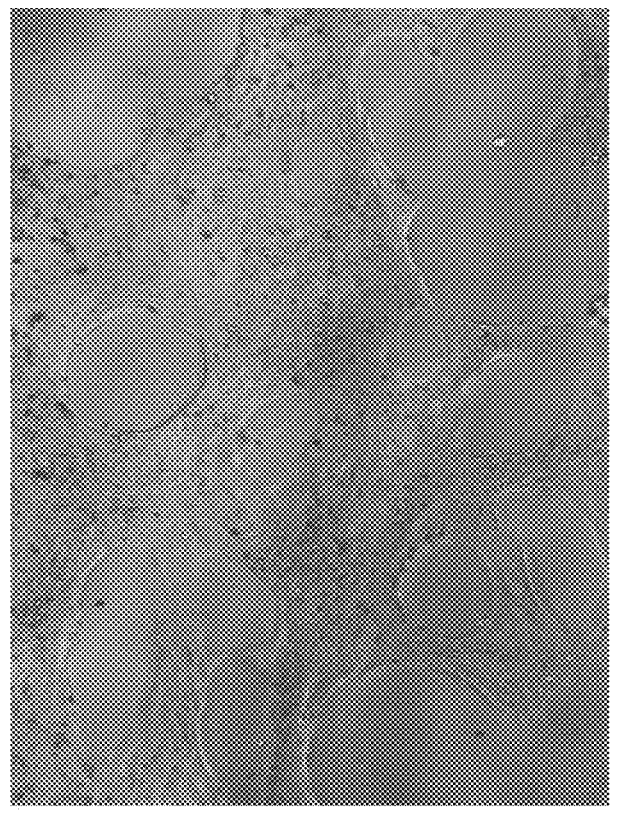
Figure 4:
FIG. 4 contains photographs iPSC-RPE cells after being cultured in differentiation medium for seven days. $1 \times 10^5$ cells were originally plated onto 96-well plates coated with 5 µg/mL of fibrinogen. The RPE cells formed a mostly confluent monolayer with big patches (arrows).
Figure 4:
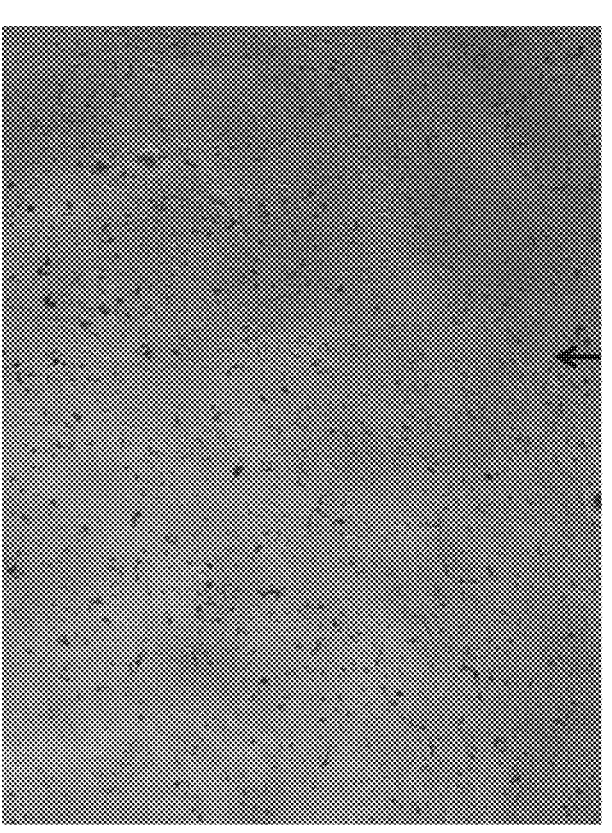
Figure 5:
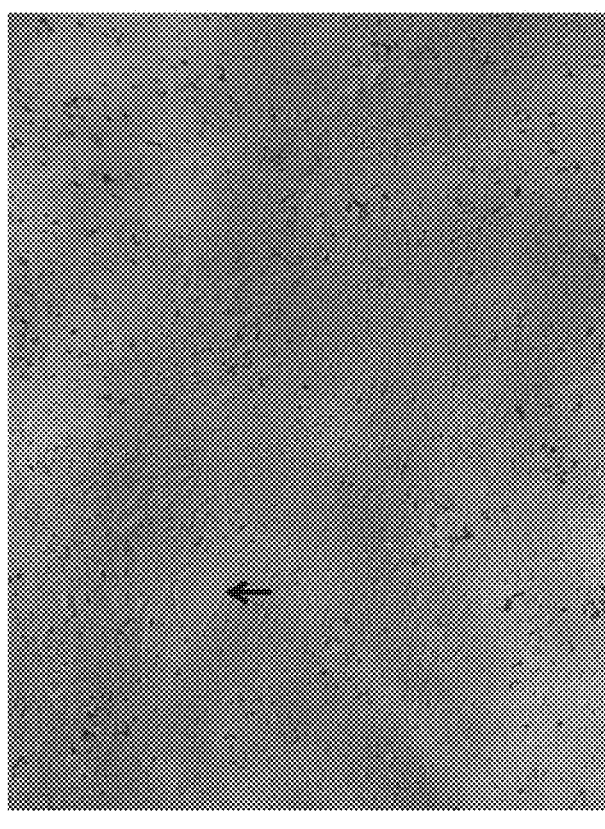
FIG. 5 contains photographs iPSC-RPE cells after being cultured in differentiation medium for seven days. $1 \times 10^5$ cells were originally plated onto 96-well plates coated with 10 µg/mL of fibrinogen. The RPE cells formed a mostly confluent monolayer with big patches (arrows).
Figure 5:
Figure 5:
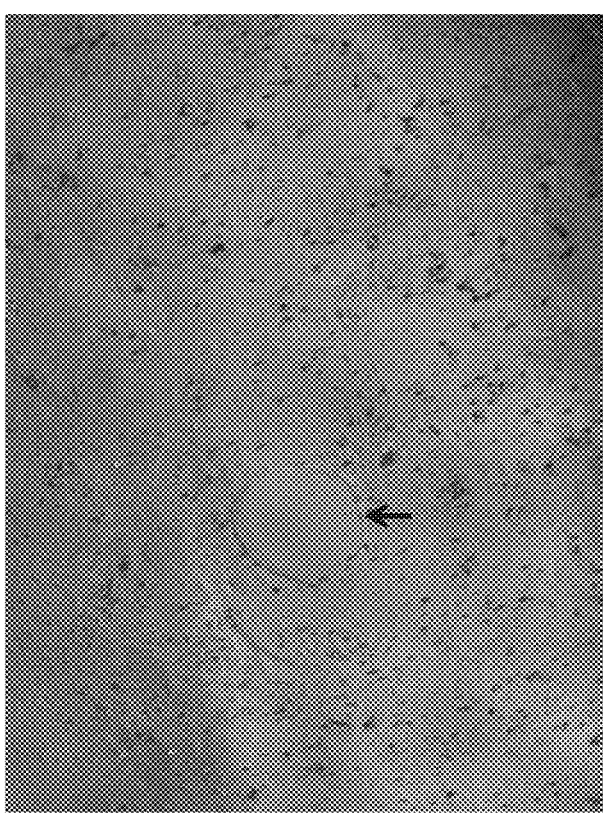
Figure 6:
FIG. 6 contains photographs iPSC-RPE cells after being cultured in differentiation medium for seven days. $1 \times 10^5$ cells were originally plated onto 96-well plates coated with 15 µg/mL of fibrinogen. The RPE cells formed a confluent monolayer with occasional patches (arrows).
Figure 6:
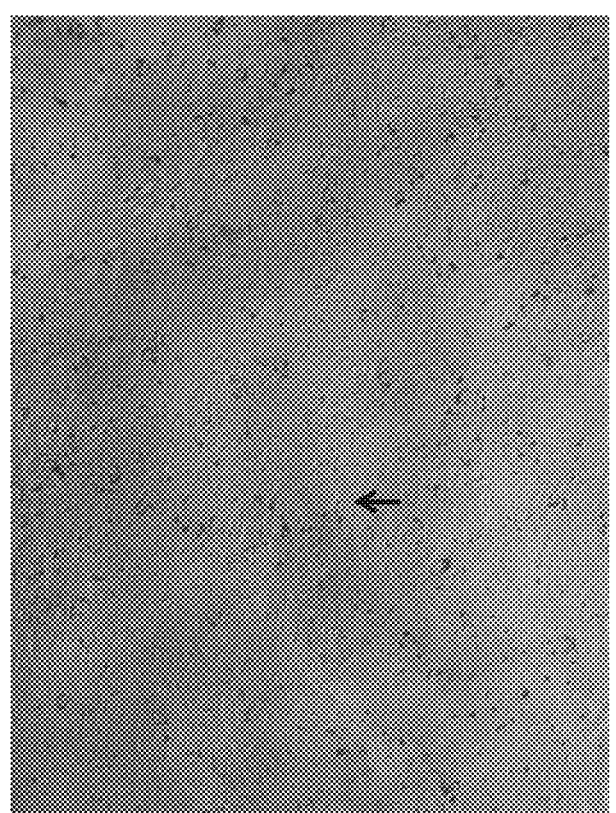
Figure 7:
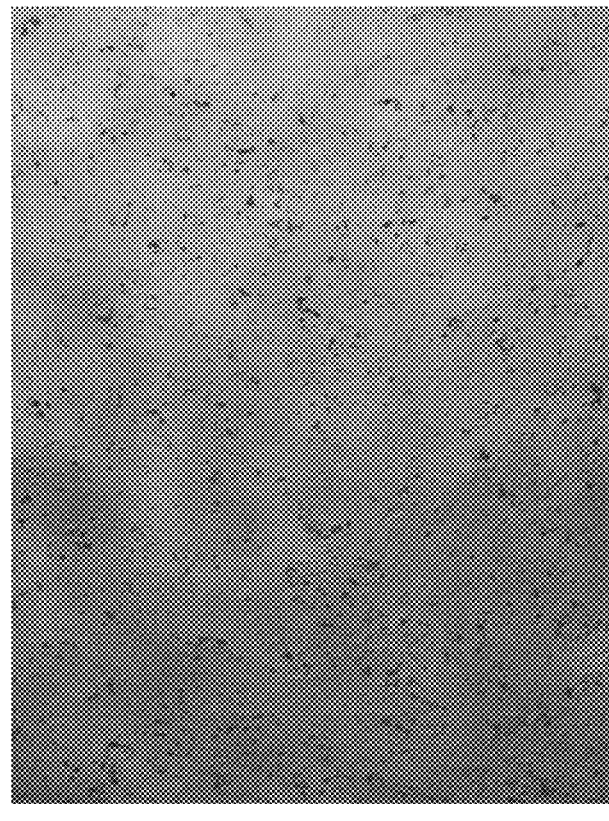
FIG. 7 contains photographs iPSC-RPE cells after being cultured in differentiation medium for seven days. $1 \times 10^5$ cells were originally plated onto 96-well plates coated with 25 µg/mL of fibrinogen. The RPE cells formed a confluent monolayer.
Figure 7:
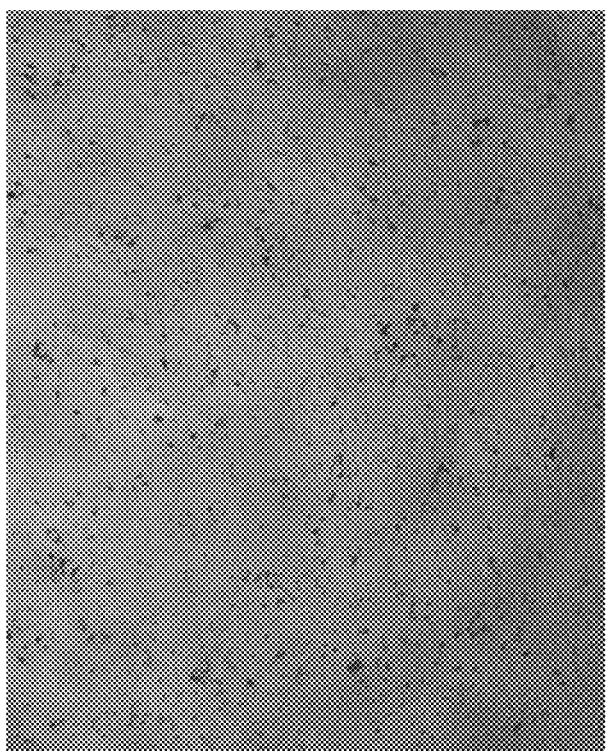
Figure 8:
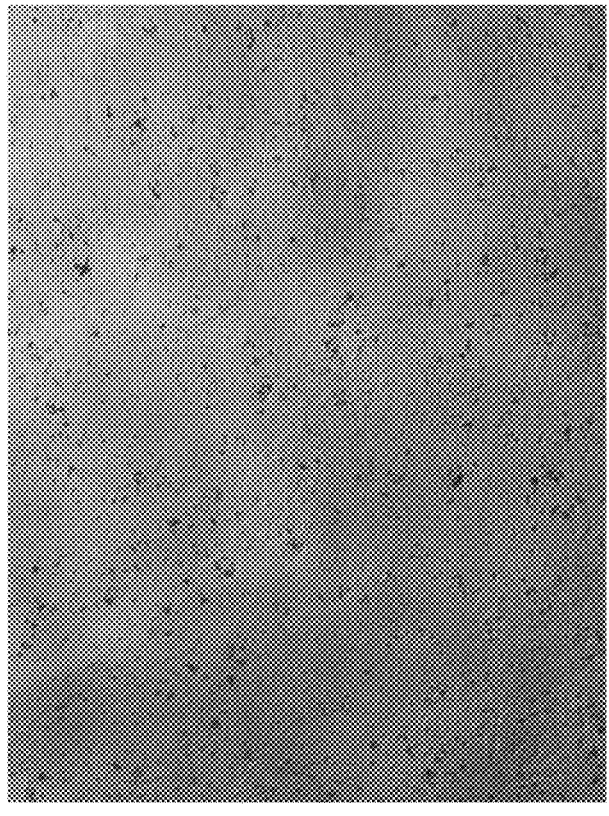
FIG. 8 contains photographs iPSC-RPE cells after being cultured in differentiation medium for seven days. $1 \times 10^5$ cells were originally plated onto 96-well plates coated with 50 µg/mL of fibrinogen. The RPE cells formed a confluent monolayer.
Figure 8:
Figure 9:
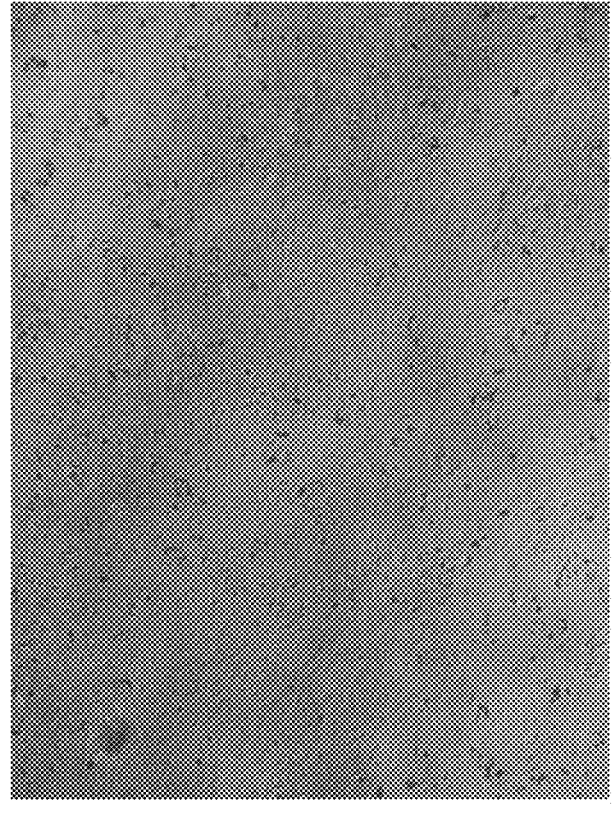
FIG. 9 contains photographs iPSC-RPE cells after being cultured in differentiation medium for seven days. $1 \times 10^5$ cells were originally plated onto 96-well plates coated with 75 µg/mL of fibrinogen. The RPE cells formed a confluent monolayer.
Figure 9:
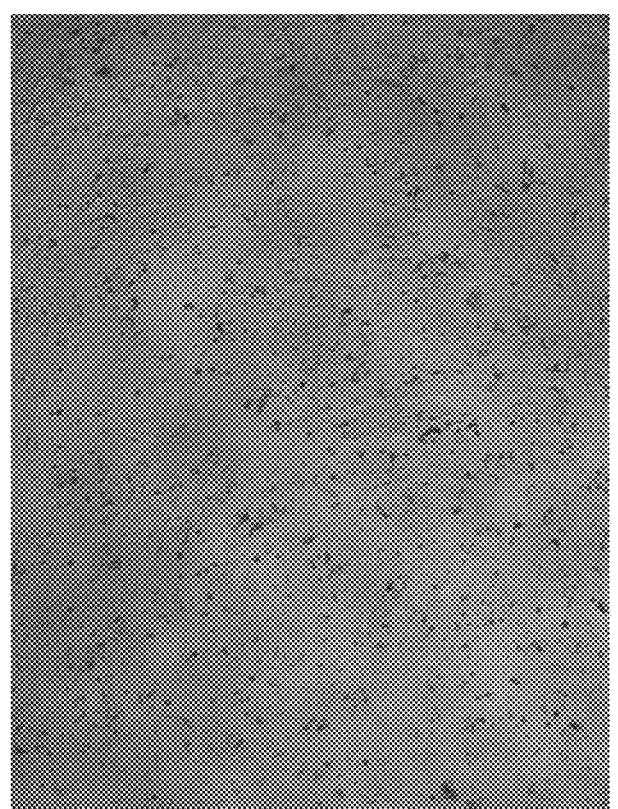
Figure 10:
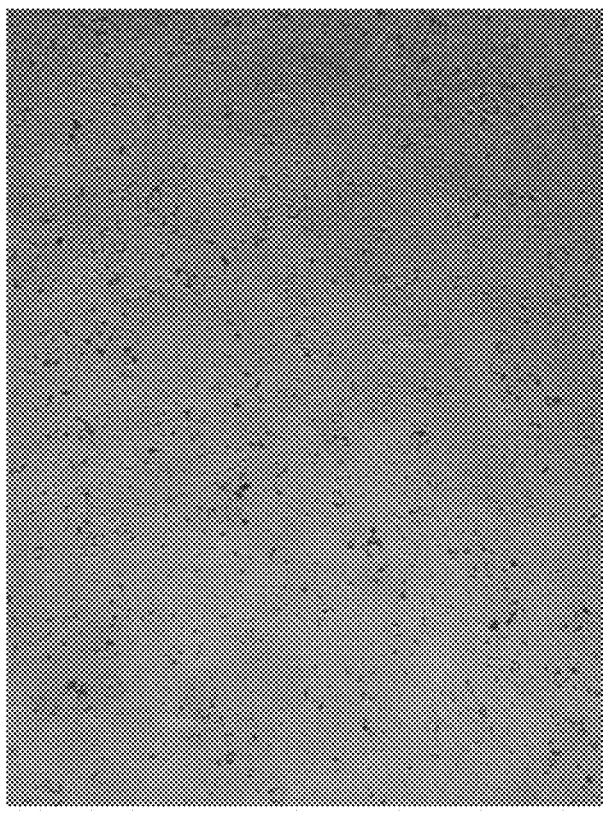
FIG. 10 contains photographs iPSC-RPE cells after being cultured in differentiation medium for seven days. $1 \times 10^5$ cells were originally plated onto 96-well plates coated with 100 µg/mL of fibrinogen. The RPE cells formed a confluent monolayer.
Figure 10:
Figure 10:
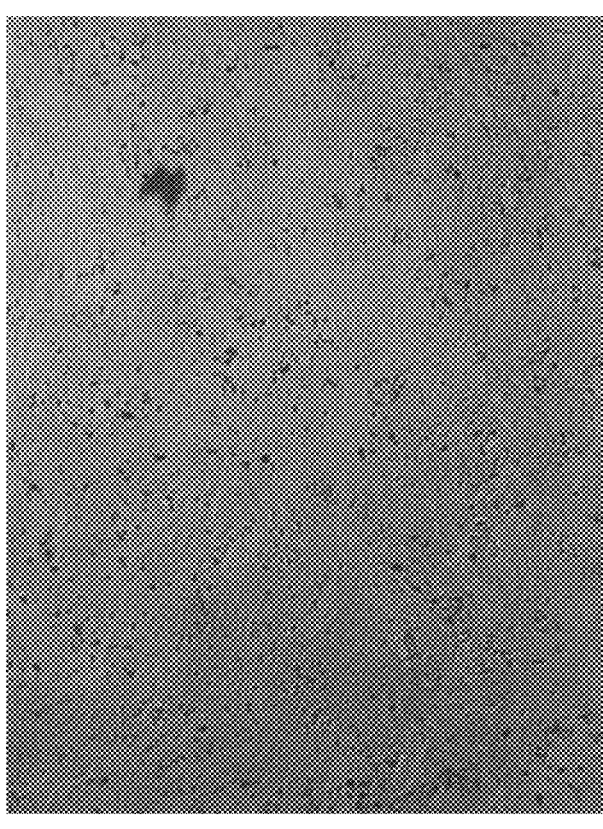
Figure 11:
FIG. 11 contains photographs iPSC-RPE cells after being cultured in differentiation medium for seven days. $1 \times 10^5$ cells were originally plated onto 96-well plates coated with 200 µg/mL of Matrigel® (a reconstituted basement membrane preparation) as a positive control. The RPE cells formed a confluent monolayer.
Figure 11:
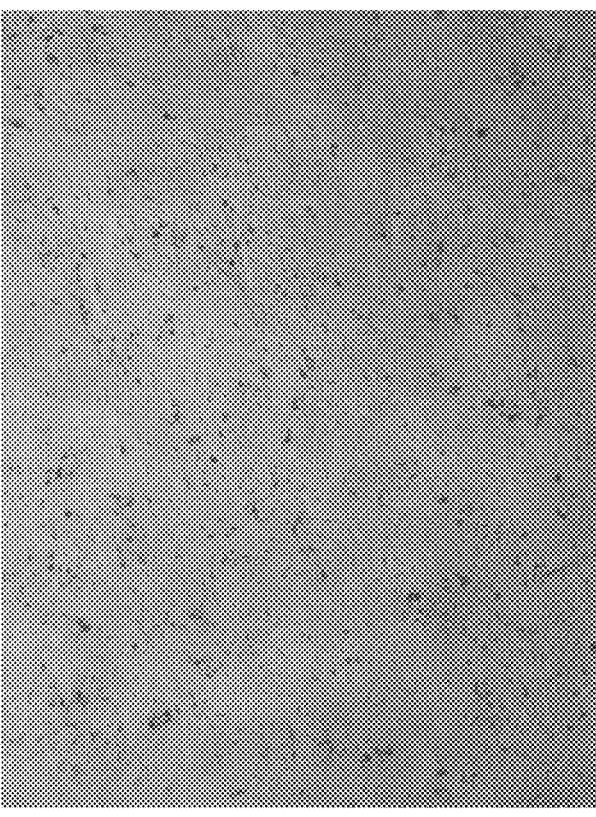
Figure 11:
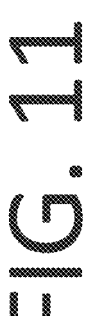
Figure 12:
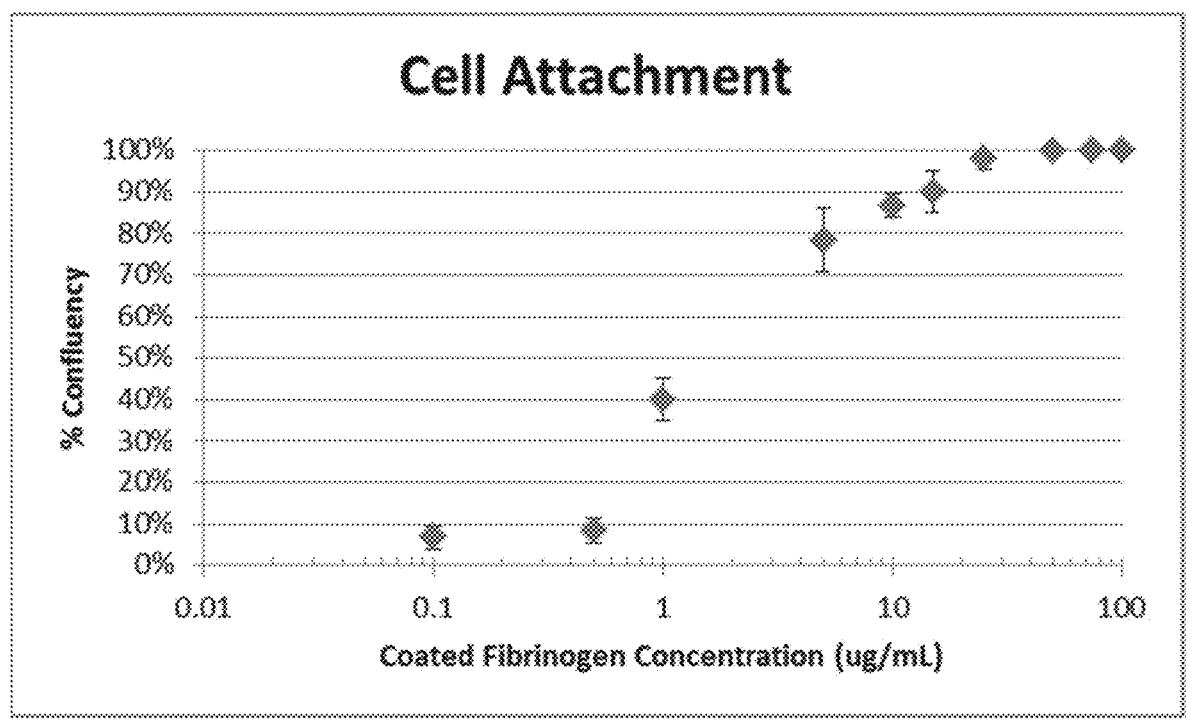
FIG. 12 is a graph plotting percent confluency plated iPSC-RPE cells after seven days of culture vs. the concentration of fibrinogen (µg/mL) used to coat the plates. Confluent monolayers were achieved with 25 to 100 µg/mL of fibrinogen, confluent monolayers with a few patches were achieved with 5 to 15 µg/mL of fibrinogen, poor monolayers were achieved with 1 µg/mL of fibrinogen, and no meaningful attachment was achieved with 0.1 to 0.5 µg/mL of fibrinogen.

Cells cultured on plates coated with 0.1 to 0.5 µg/mL of fibrinogen for one week either did not, or were poorly attached (FIGS. 1 and 2) to the plate. While some cells cultured on plates coated with 1 µg/mL of fibrinogen for one week did attach, monolayer formation was poor (FIG. 3). Cells cultured on plates coated with 5 to 15 µg/mL of fibrinogen for one week resulted in the formation of patchy monolayers (FIGS. 4-6). Cells cultured on plates coated with 25 µg/mL or more of fibrinogen for one week formed confluent monolayers (FIGS. 7-10). The monolayers shown in FIGS. 7-10 were similar to those obtained using the positive control (FIG. 11). See, also, FIG. 12.

Figure 13:
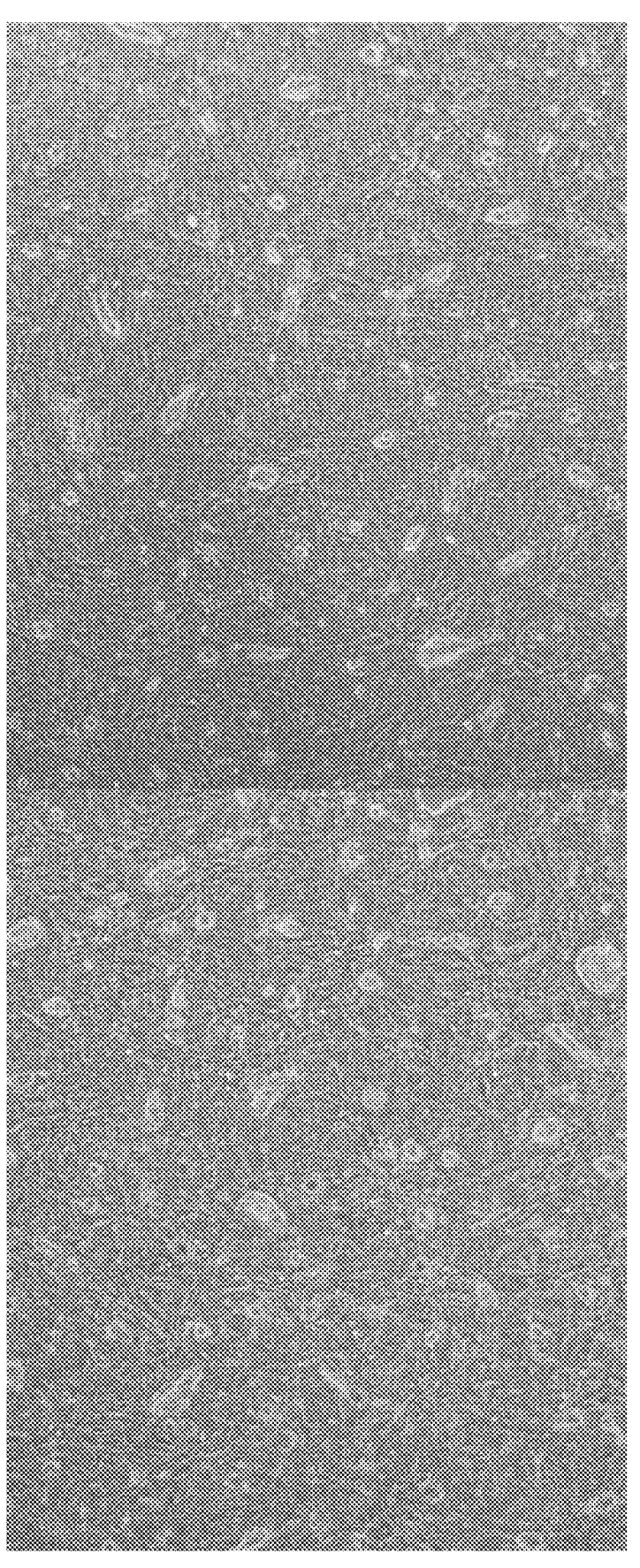
FIG. 13 contains photographs iPSC-RPE cells after being cultured in differentiation medium for one week. $5 \times 10^6$ cells were originally plated onto 6-well plates coated with 100 µg/mL of fibrinogen (right panel) or 200 µg/mL of Matrigel® as a positive control (left panel). The RPE cells formed confluent monolayers. 4× objective.
Figure 14:
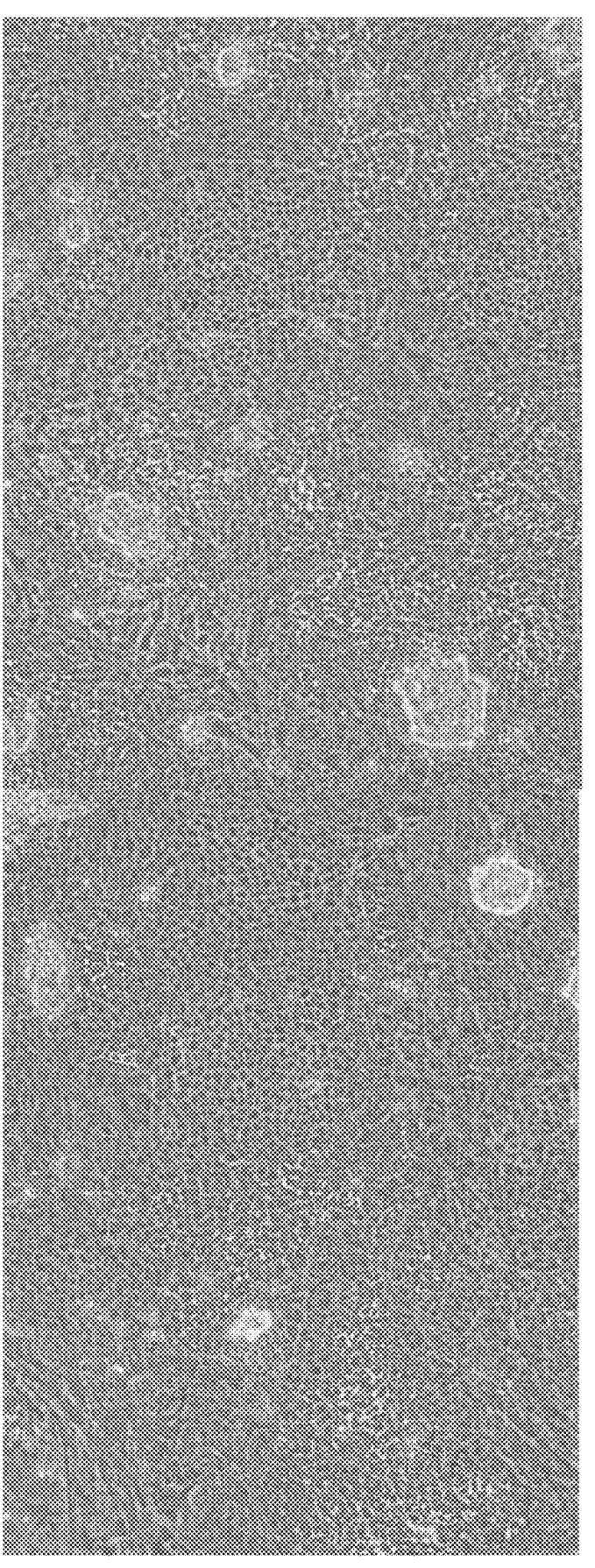
FIG. 14 contains photographs iPSC-RPE cells after being cultured in differentiation medium for one week. $5 \times 10^6$ cells were originally plated onto 6-well plates coated with 100 µg/mL of fibrinogen (right panel) or 200 µg/mL of Matrigel® as a positive control (left panel). The RPE cells formed confluent monolayers. RPE cells form cobblestone appearance with hexagonal patterning. 20× objective.
Figure 15:
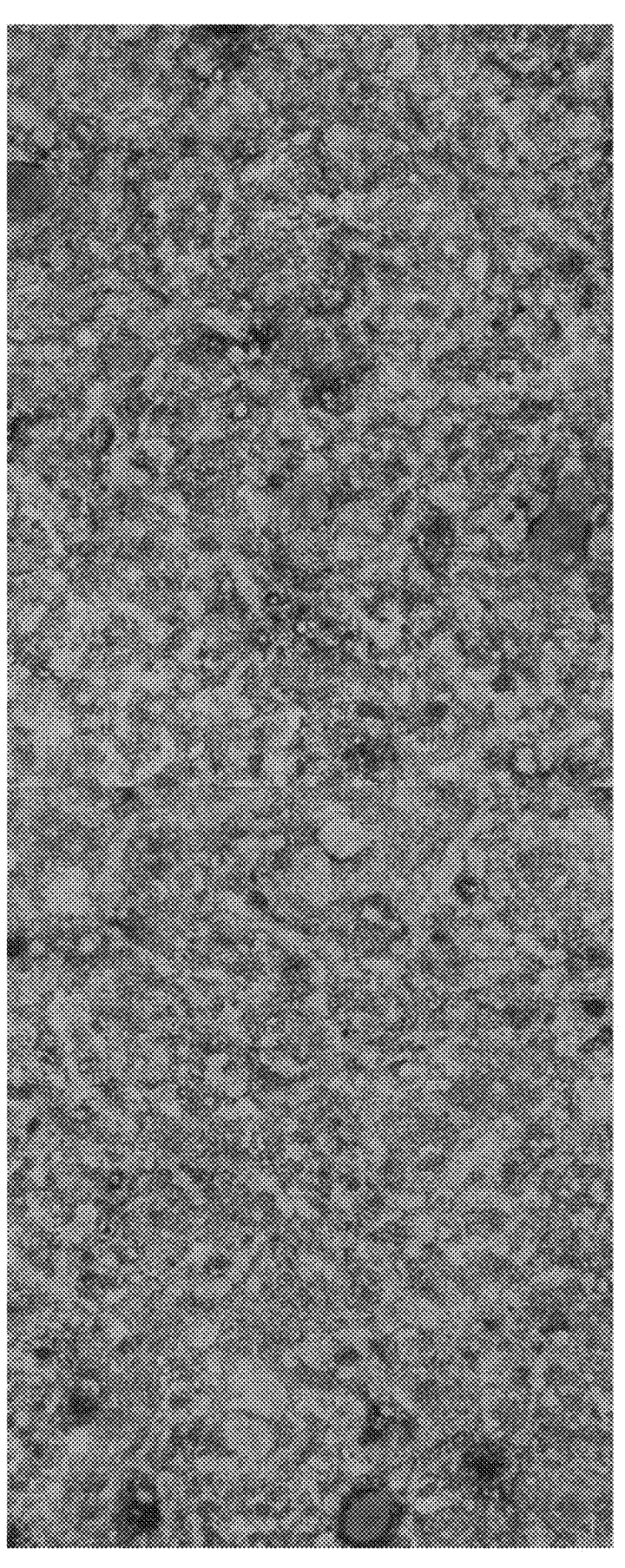
FIG. 15 contains photographs iPSC-RPE cells after being cultured in differentiation medium for six weeks. $5 \times 10^6$ cells were originally plated onto 6-well plates coated with 100 µg/mL of fibrinogen (right panel) or 200 µg/mL of Matrigel® as a positive control (left panel). The RPE cells formed confluent monolayers. Large areas of pigmented cells are visible in both groups. 4× objective.
Figure 16:
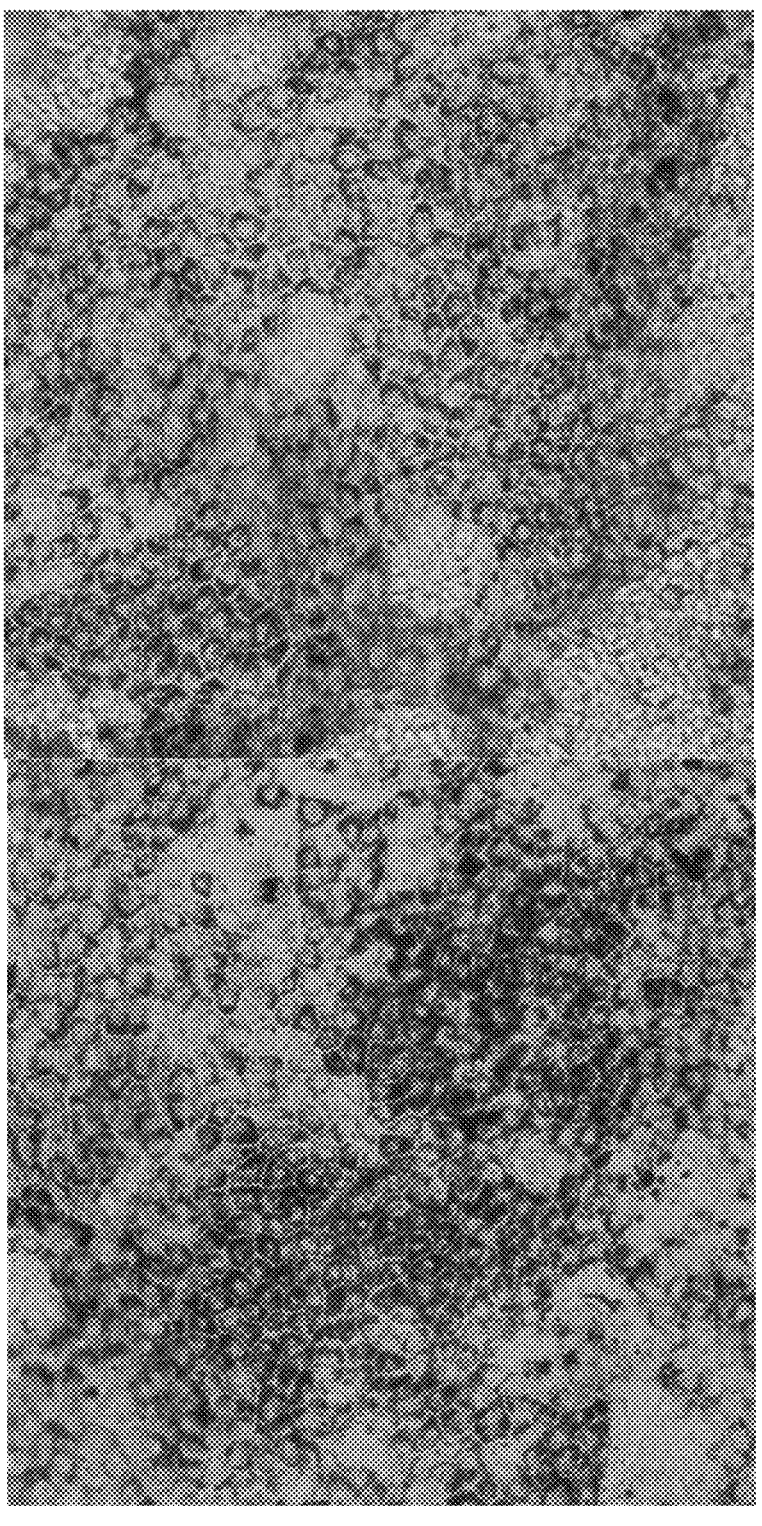
FIG. 16 contains photographs iPSC-RPE cells after being cultured in differentiation medium for six weeks. $5 \times 10^6$ cells were originally plated onto 6-well plates coated with 100 µg/mL of fibrinogen (right panel) or 200 µg/mL of Matrigel® as a positive control (left panel). The RPE cells formed confluent monolayers. Characteristic pigmented, hexagonally patterned RPE cells are visible in both groups. 20× objective.
Figure 17:
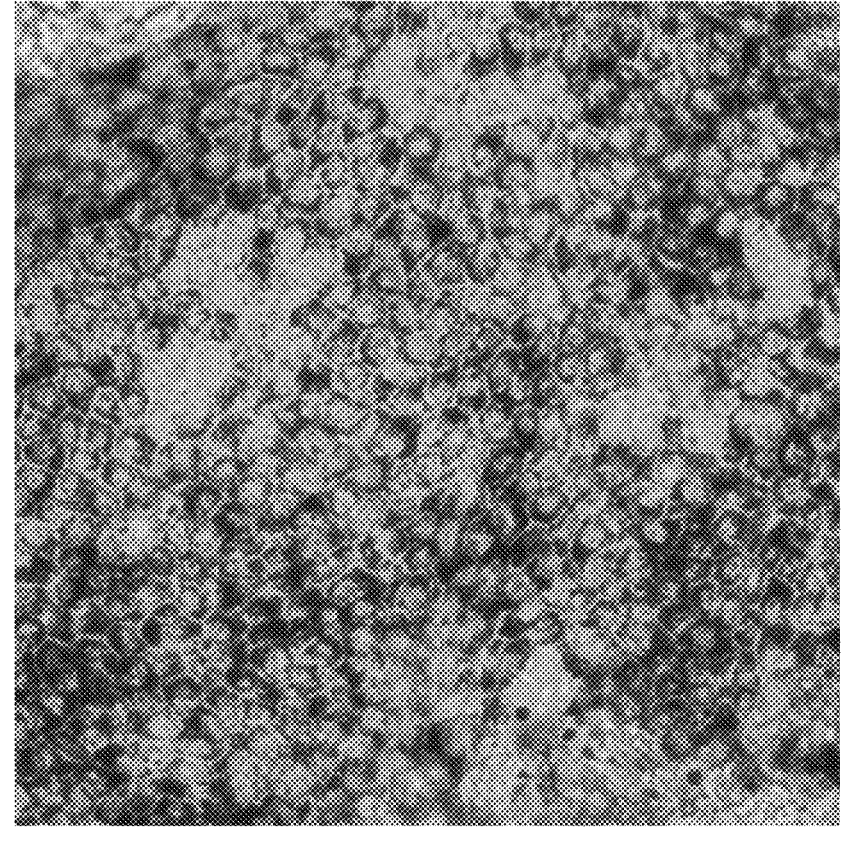
FIG. 17 contains photographs iPSC-RPE cells after being cultured in differentiation medium for twelve weeks. $5 \times 10^6$ cells were originally plated onto 6-well plates coated with 100 µg/mL of fibrinogen (right panel) or 200 µg/mL of Matrigel® as a positive control (left panel). The RPE cells formed confluent monolayers. RPE appear pigmented, and hexagonally shaped in both groups. 20× objective.
Figure 17:
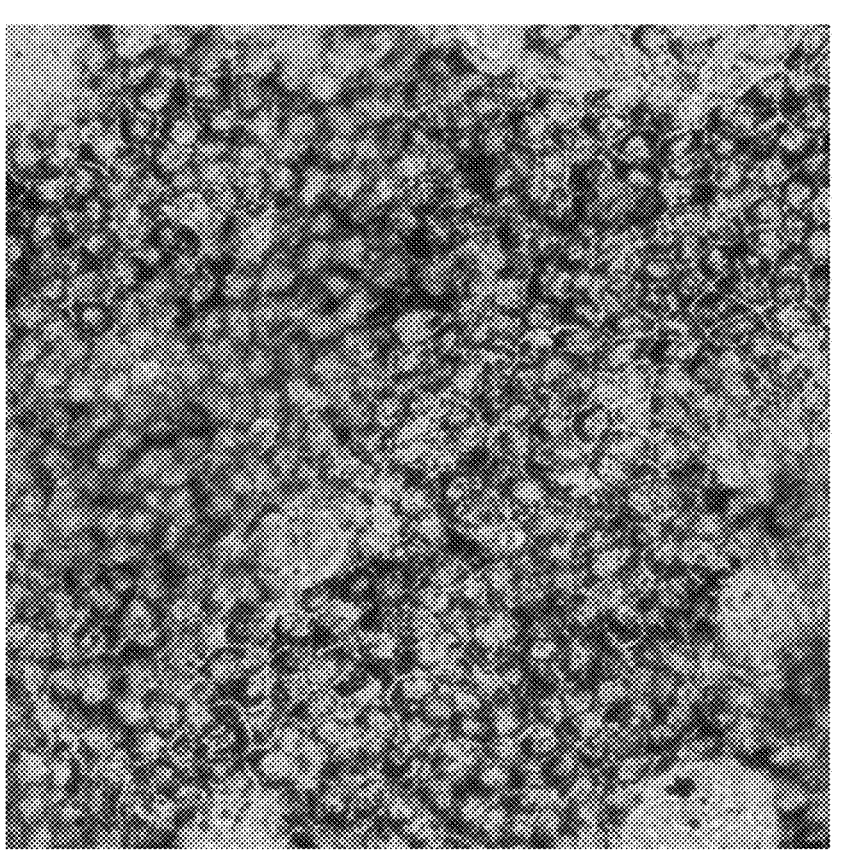
Figure 18:
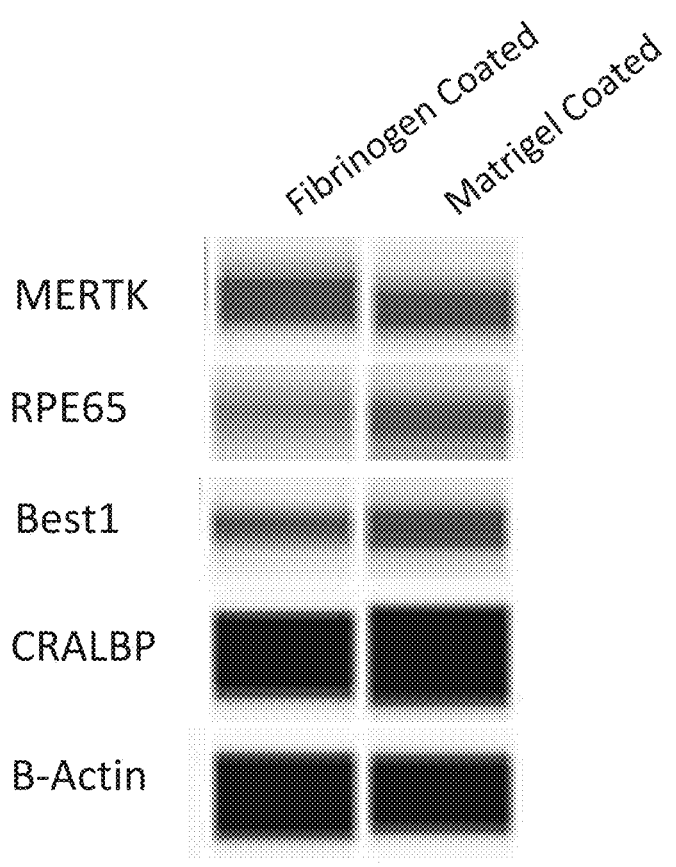
FIG. 18 is a photograph of a Western blot of iPSC-RPE cells after being cultured in differentiation medium for twelve weeks. $5 \times 10^6$ cells were originally plated onto plates coated with 100 µg/mL of fibrinogen (fibrinogen coated) or 200 µg/mL of Matrigel® as a positive control (Matrigel® coated). MERTK indicates proto-oncogene tyrosine-protein kinase MER; RPE65 indicates retinoid isomerohydrolase; Best1 indicates Bestrophin 1; CRALBP indicates retinaldehyde-binding protein 1 and B-Actin indicates R-actin polypeptides.
Figure 19:
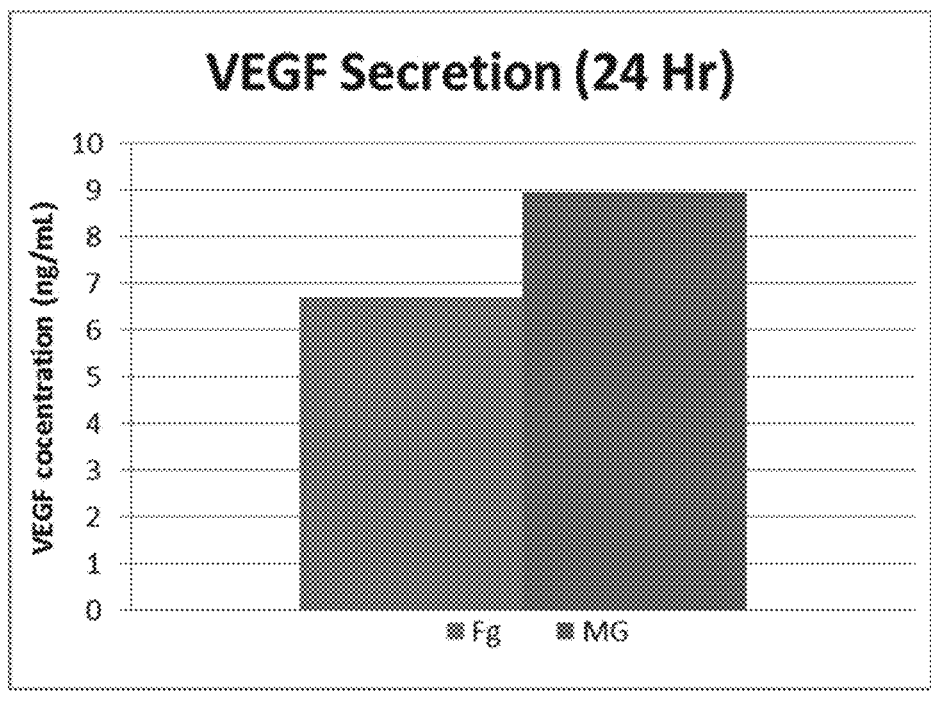
FIG. 19 contains bar graphs plotting the concentration of VEGF and PEDF secretion into culture media over 24 hours. $5 \times 10^6$ cells were originally plated onto plates coated with 100 µg/mL of fibrinogen (Fg) or 200 µg/mL of Matrigel® as a positive control (MG) and cultured for 12 weeks. The concentrations were determined via ELISA. n=1.
Figure 19:
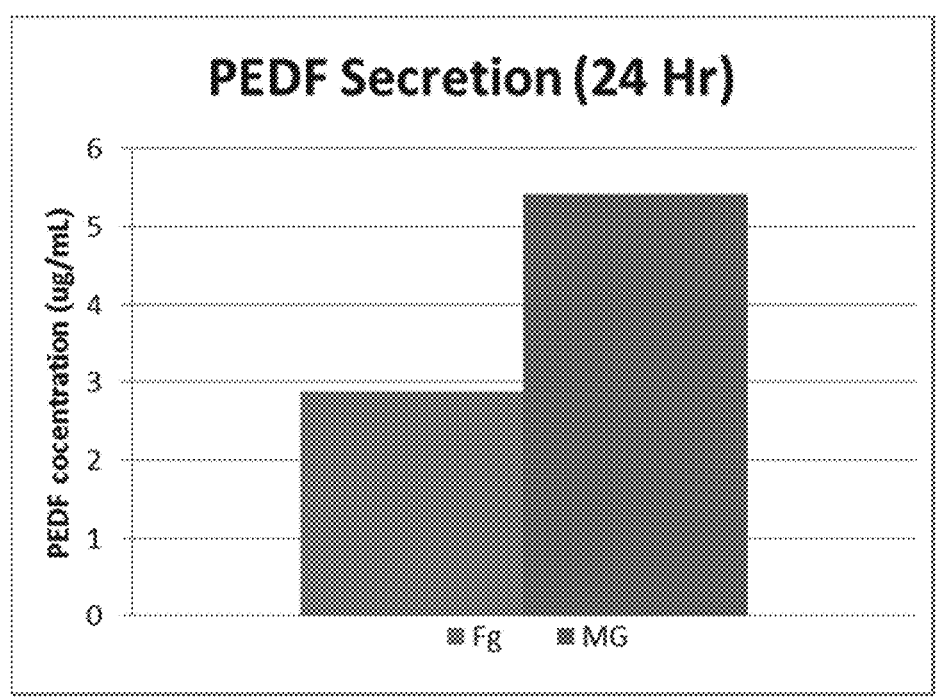

Monolayers formed using partially differentiated iPSC-RPE cells and cultured on plates coated with 100 µg/mL of fibrinogen or 200 µg/mL of Matrigel® (i.e., positive control) for one week (FIGS. 13-14), six weeks (FIG. 15-16), or twelve weeks (FIG. 17) resulted in monolayers that were indistinguishable from each other. These monolayers exhibited characteristic RPE morphology (pigment and a "cobblestone" appearance) within six weeks. In addition, the cells cultured using plates coated with 100 µg/mL of fibrinogen or 200 µg/mL of Matrigel® (i.e., positive control) exhibited comparable protein expression profiles after 12 weeks of culture (FIG. 18). 24- to 48-hour culture supernatants from both cultures also contained high levels of secreted VEGF and pigment epithelium-derived factor (PEDF) characteristic of RPE cells (FIG. 19). These results demonstrate that fibrinogen can be used as a substrate for forming healthy, viable iPSC-RPE monolayers.

Fibrinogen preparations from the following sources were tested: Ethicon (Evicel®), Baxter (Tisseel™), Sigma-Aldrich®, Millipore®, and extractions created from cryoprecipitate and ethanol. Differences were observed in terms of efficiency of plate coating and minimum concentration needed (Table 1). In addition, fibrinogen obtained from Sigma-Aldrich® or Millipore®/EMD did not support proper adhesion of iPSCs. These products were obtained as a lyophilized powder and were reconstituted prior to use. This may suggest that lyophilization may affect the ability to use fibrinogen as a coating material. However, Tisseel™, which also was reconstituted from lyophilization, enabled proper adhesion of iPSC-RPE. No correlation of absolute fibrinogen levels with effectiveness of different commercial preparations was observed. Protein denaturation could occur during a lyophilization process/formulation or after long-term storage, in particular in the absence of proper freeze-drying process and/or cryo-lyoprotectant. Thus, it can be beneficial to optimize human fibrinogen commercial formulations specifically prepared for use as a surface coating for tissue culture as well as for use in the production of hydrogels that may be used for 3D cell culture or to develop scaffolds for cell therapy applications.

TABLE 1

Plate coating efficiency and minimum concentration for iPSC-RPE.

| Preparation | Plate coating efficiency | Minimum concentration for max confluency |
|---|---|---|
| Evicel ® | Confluent | 25 µg/mL |
| Tisseel ™ | Confluent | 20 µg/mL |
| Sigma-Aldrich ® | Best, 80%-90% confluency, with holes | 10 µg/mL |
| Millipore ® | Best, 60%-80% confluency, with holes | 10 µg/mL |
| Cryoprecipitate Extract | confluent | 10 µg/mL |
| Ethanol-precipitate Extract | confluent | 10 µg/mL |

Phagocytosis Results

Figure 23:
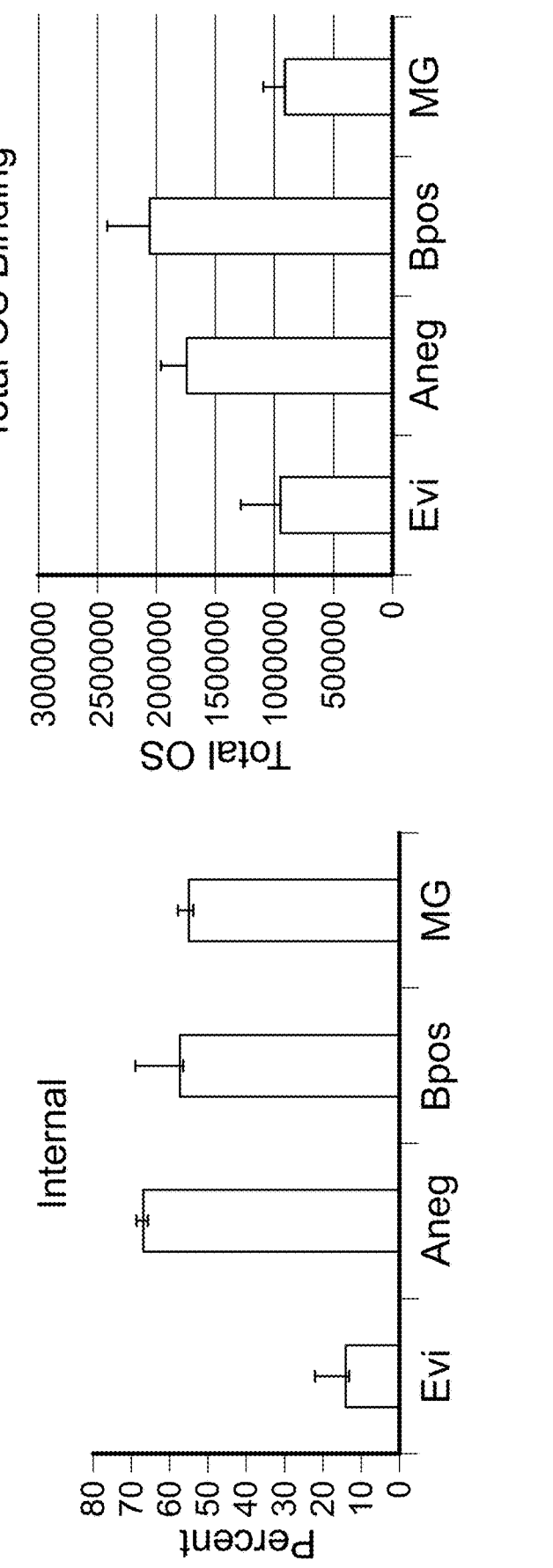
FIG. 23 contains graphs plotting the percent of internalized rod outer segments (ROS) and total binding of ROS using a phagocytosis assay with iPSC-RPE. $1\times10^5$ cells were plated onto each well of 96 well plates coated with 100 µg/mL of fibrinogen (3 different preps: Evicel® (evi; cryoprecipitated fibrinogen), cryo1 (Aneg), and cryo2 (Bpos)) or 200 µg/mL of Matrigel® (MG) as a positive control and cultured for 8 weeks. N=3.

A phagocytosis assay was performed as described elsewhere (Marmorstein et al., *Sci. Rep.*, 8:4487 (2018)). iPSC-RPE were grown on various sources of fibrinogen: Evicel®, and 2 separate cryoprecipiates (Aneg and Bpos). Matrigel® coating was used as a positive control. RPE cultured on Evicel® (Evi) showed similar total OS binding to Matrigel®, while Aneg and Bpos demonstrated an almost two fold increase in total OS binding (FIG. 23). Once bound, Aneg (67%) and Bpos (57%) showed similar rates of internalization as MG (55%), while Evi (14%) was significantly lower than MG (p=0.009).

Western Blot Analysis Results

Figure 24:
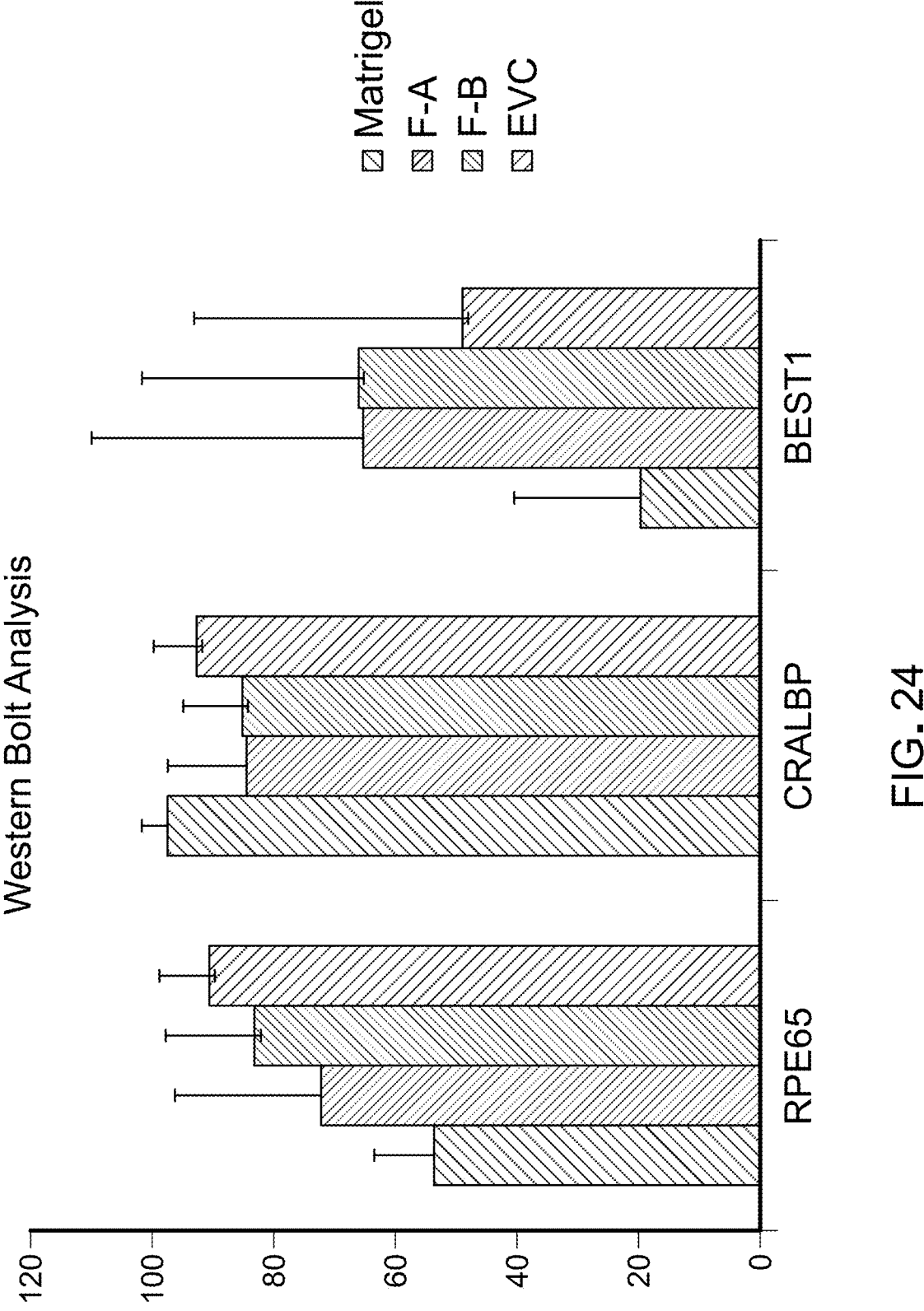
FIG. 24 contains graphs plotting relative RPE marker expression using Western Blot analysis. $1\times10^5$ cells were plated onto each well of 96 well plates coated with 100 µg/mL of fibrinogen (3 different preps: Evicel® (evi), cryo1 (Aneg), and cryo2 (Bpos)) or 200 µg/mL of Matrigel® (MG) as a positive control and cultured for 8 weeks. N=3.
Figure 25:
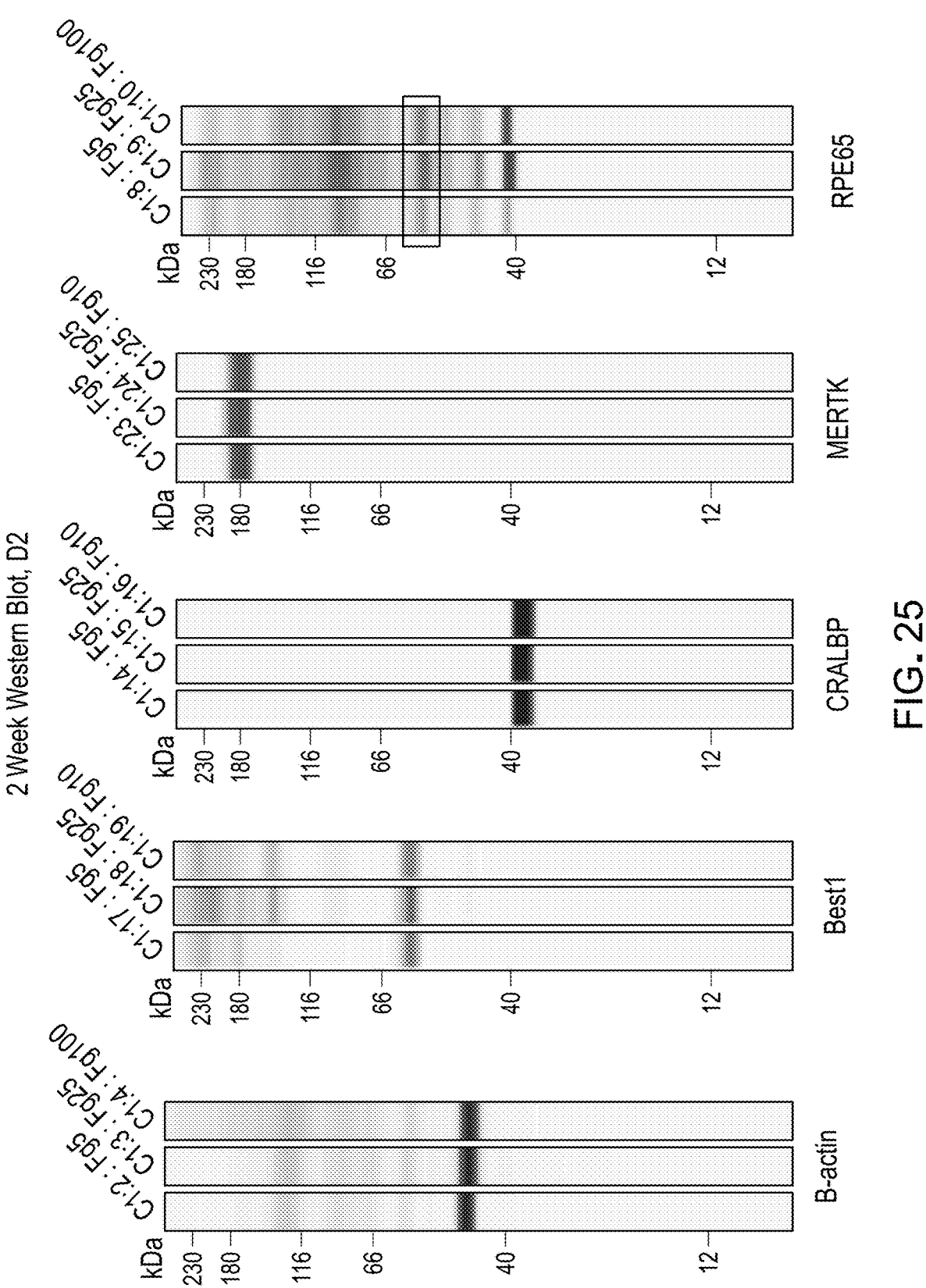
FIG. 25 contains photographs of a Western blot of iPSC-RPE cells after being cultured in differentiation medium for 2 weeks. $1\times10^5$ cells were plated onto each well of 96 well plates coated with 5, 25, or 100 µg/mL of fibrinogen (Fg5, Fg25, and Fg100, respectively).
Figure 26:
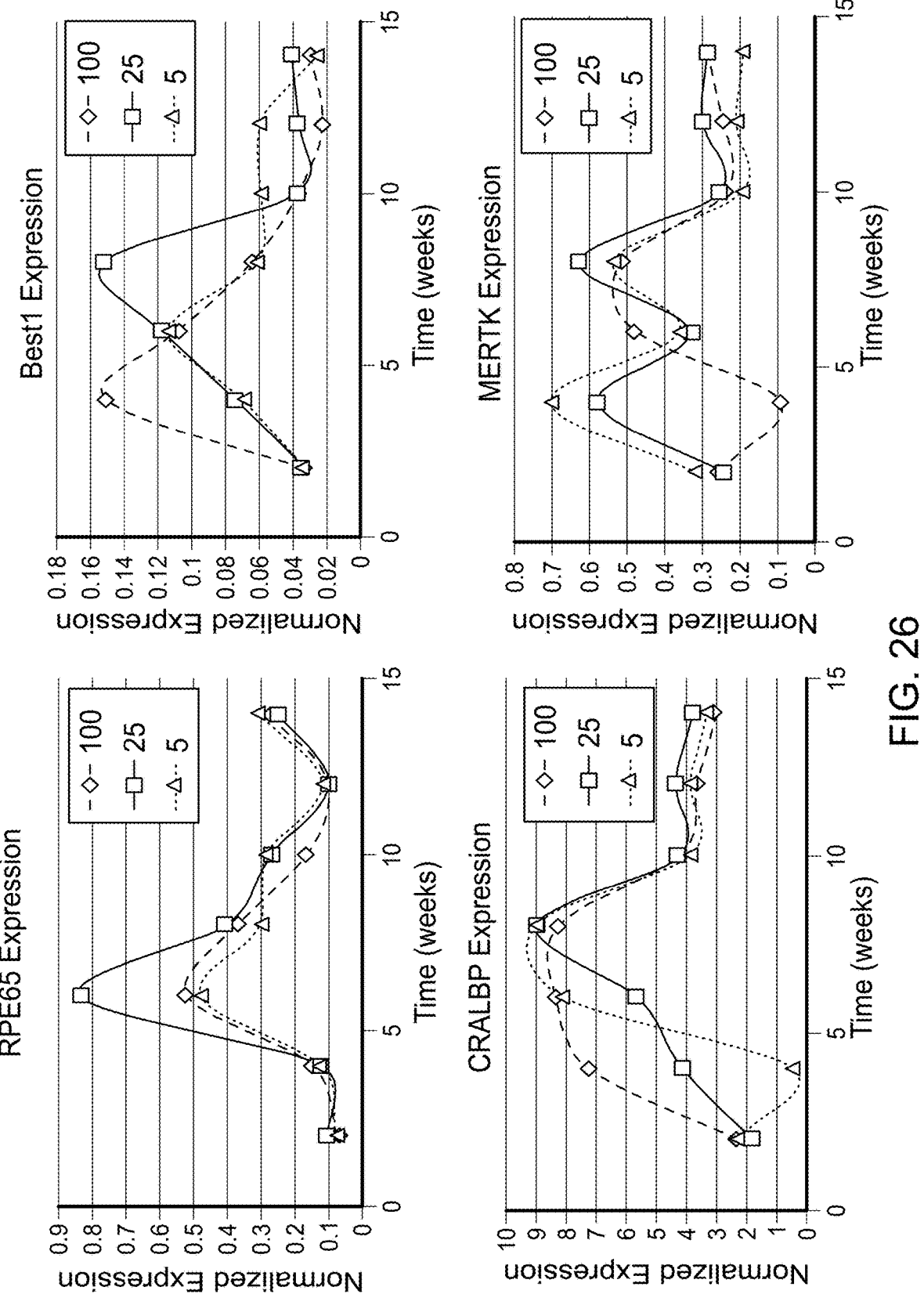
FIG. 26 contains graphs of western blot quantification of RPE markers in iPSC-RPE after being cultured in differentiation medium from week 2 to week 14. $1\times10^5$ cells were plated onto each well of 96 well plates coated with 5, 25, or 100 µg/mL of fibrinogen (Fg5, Fg25, and Fg100, respectively).

A western blot comparison of RPE65, CRALBP, and BEST1 expression was performed for RPE grown on various coating reagents (FIG. 24). Fibrinogen-based substrates showed increased expression of RPE65 and Best1 compared to Matrigel® controls, when normalized to internal β-actin signal. CRALBP showed no difference between all groups.

iPSC-RPE grown on fibrinogen-coated plates expressed the characteristic RPE markers, including RPE65, Best1, CRALBP, and MERTK, as early as 2 weeks post plating (FIG. 25). Matrigel® coated plates typically required 6-8 weeks prior to RPE65 and Best1 expression. Western blots were analyzed for three different fibrinogen coating concentrations (5, 25, and 100 µg/mL) over the course of time (FIG. 26). Each of the four markers appeared to peak around week 8, with a plateau after week 10. While there were no normalized differences between the three coating concentrations, the 5 µg/mL condition did not always lead to a confluent monolayer.

Figure 27:
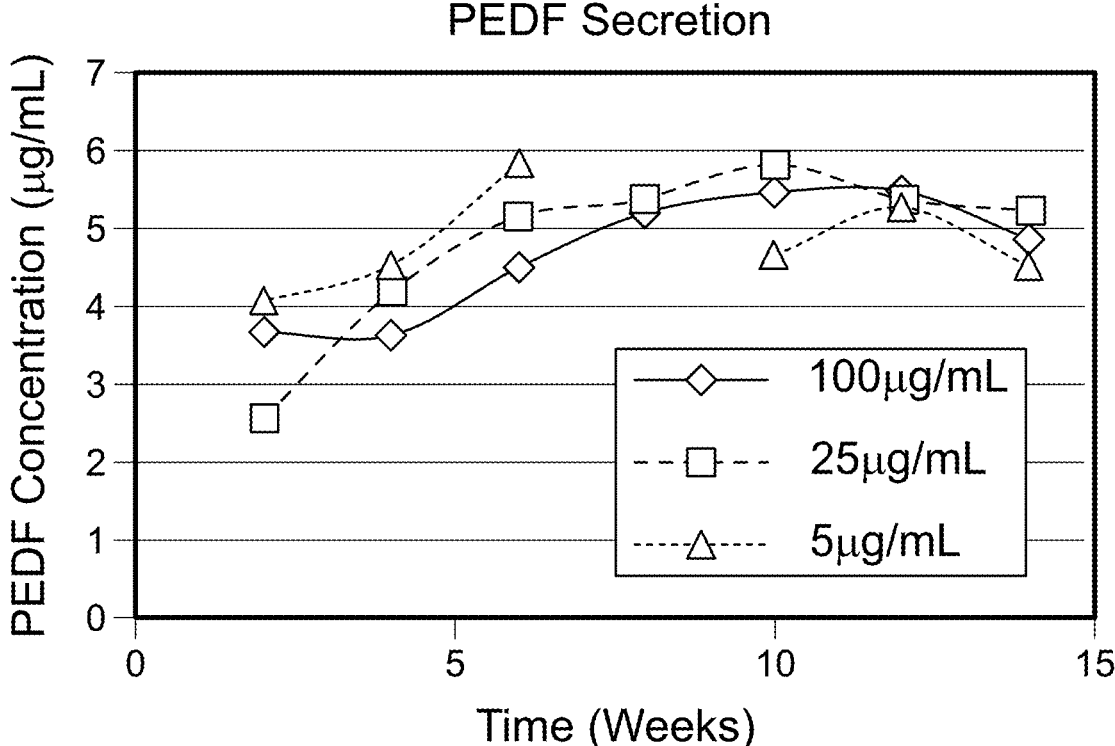
FIG. 27 contains graphs plotting the concentration of PEDF and VEGF secretion into culture media over 48 hours. $1\times10^5$ cells were plated onto each well of 96 well plates coated with 5, 25, or 100 µg/mL of fibrinogen (Fg5, Fg25, and Fg100, respectively) over week 2 to week 14. The concentrations were determined via ELISA. N=1.
Figure 27:
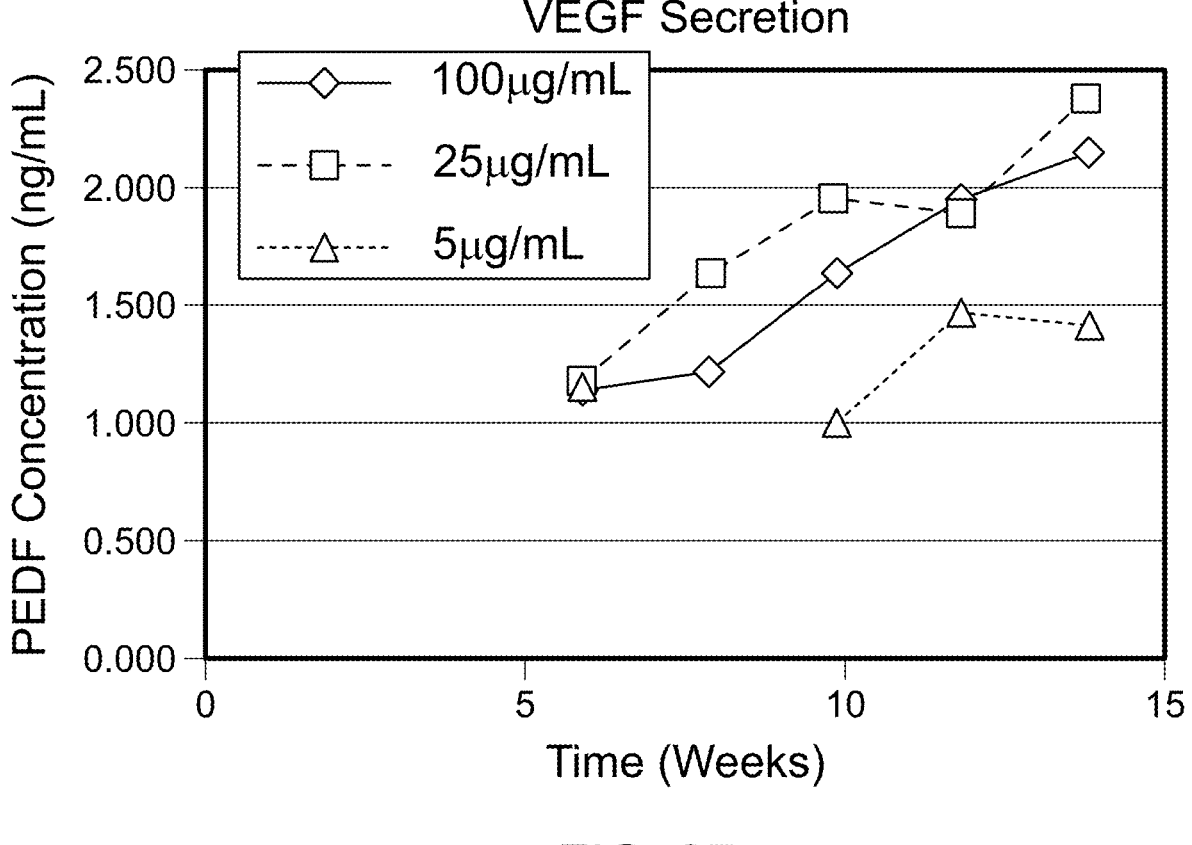

Similarly, a time course of PEDF and VEGF secretion was measured using ELISA (FIG. 27). PEDF, from week 2 to week 14, exhibited a general trend of increasing concentrations, with a maximum at week 10. No difference was noticeable between the coating concentrations. VEGF, from week 6 to week 14, exhibited a general increase in secretion over time. VEGF release in the 5 µg/mL coating concentration appeared reduced compared to the 25 and 100 µg/mL conditions.

Figure 28:
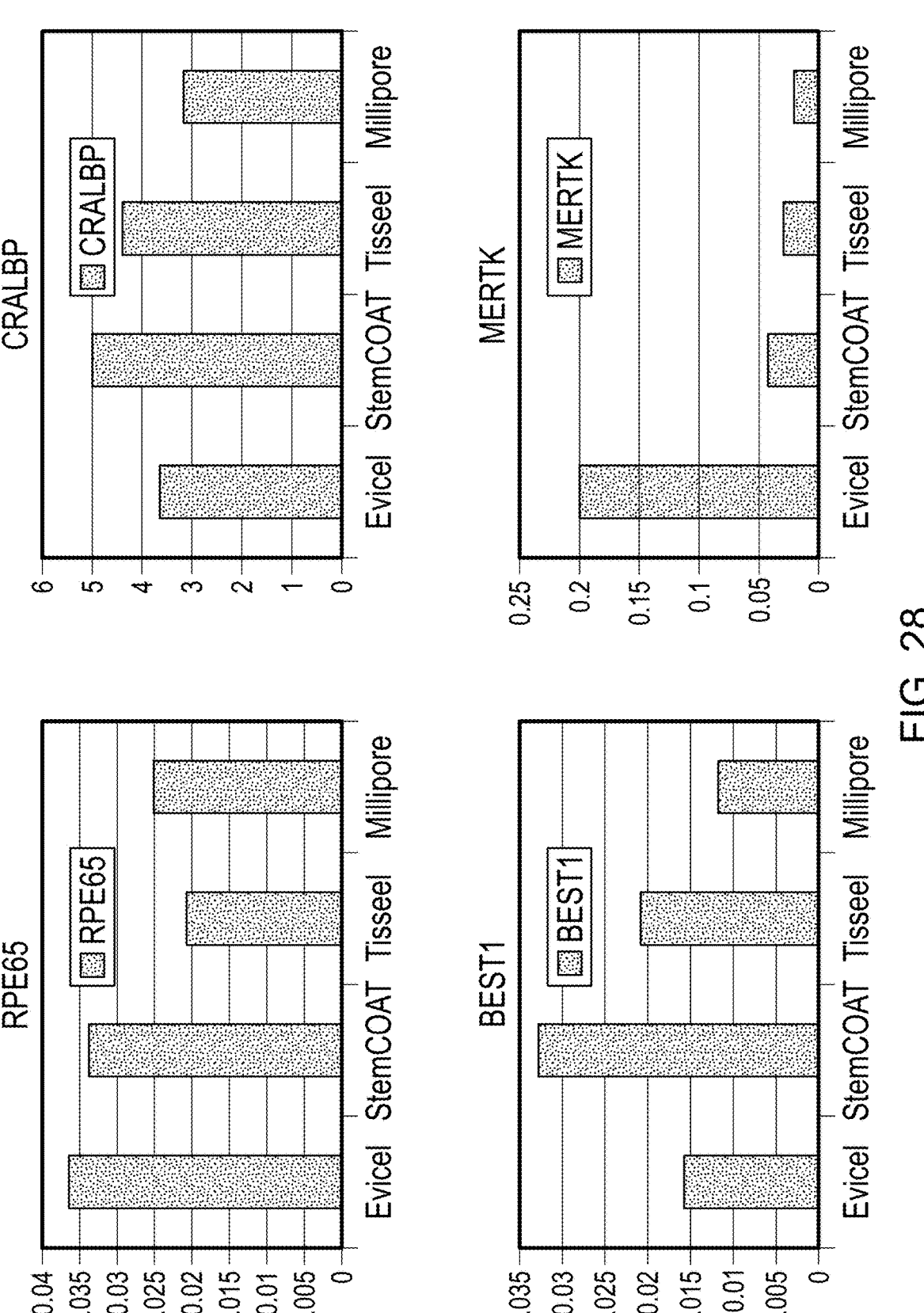
FIG. 28 contains graphs of western blot quantification of RPE markers in iPSC-RPE after being cultured in differentiation medium over 8 weeks. $1\times10^5$ cells were plated onto each well of 96 well plates coated with 100 µg/mL of fibrinogen (4 different fibrinogen sources: Evicel®, stemCOAT® (fibrinogen source), Tisseel™ (a fibrin sealant), and Millipore®). n=1.

RPE marker expression in RPE cultured on various commercial fibrinogen sources at 100 µg/mL concentration were compared (FIG. 28). Evicel® and stemCOAT® outperformed all other sources tested, including Tisseel™ and Millipore® Sigma® did not adhere iPSC-RPE at 100 µg/mL and was not included for the western blot analysis.

Figure 29:
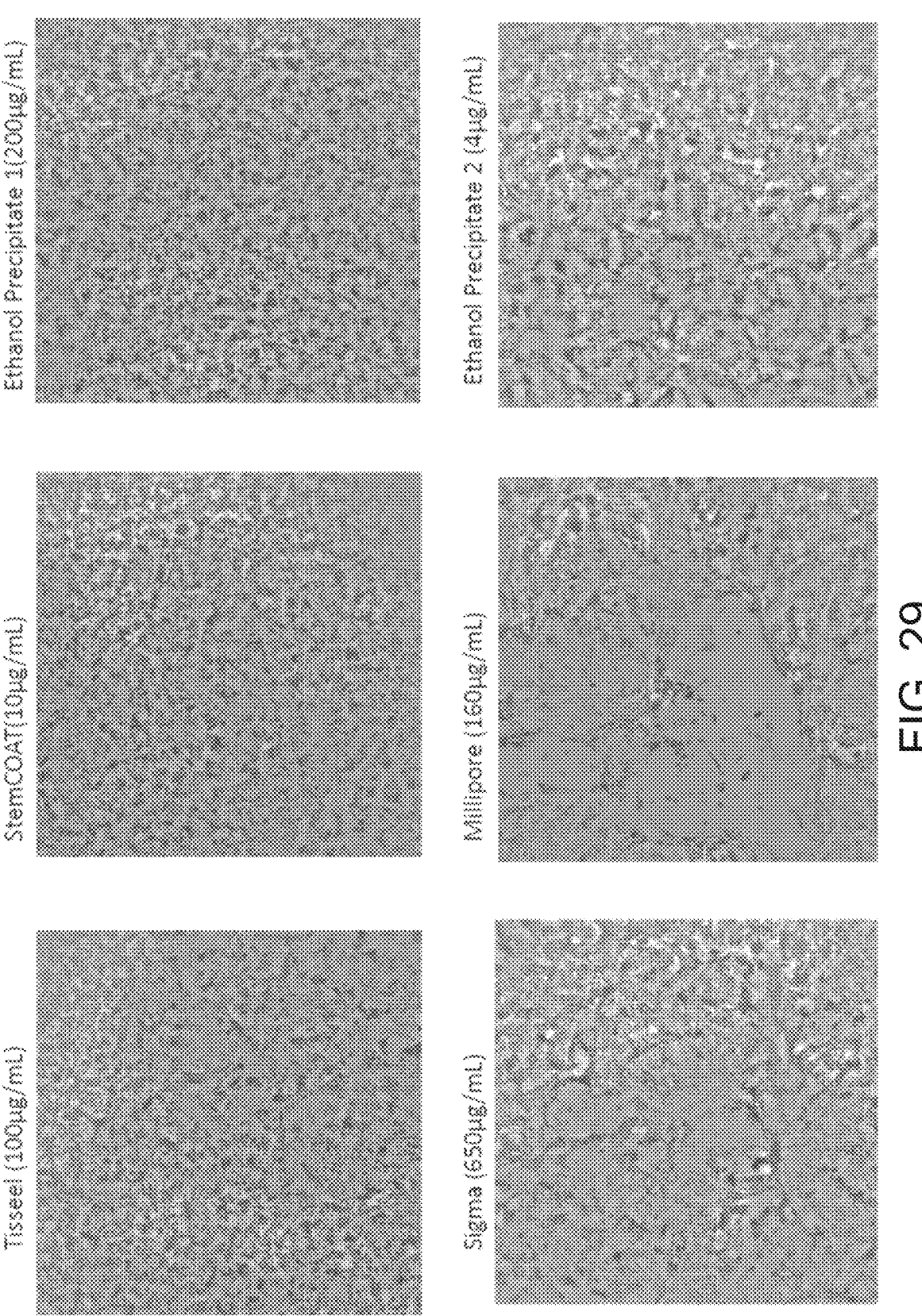
FIG. 29 contains photographs of iPSC-RPE after being cultured in differentiation medium for 12 weeks. $1\times10^5$ cells (WiCell® clone 4) were plated onto each well of 96 well plates coated with various concentrations of fibrinogen (6 fibrinogen sources: Tisseel™, stemCOAT®, Ethanol Precipitate 1, Sigma®, Millipore®, and Ethanol Precipitate 2). Listed concentration represents lowest concentration with best monolayer appearance.

Similarly, transmitted light photographs of WiCell® clone 4-derived iPSC-RPE cultured on the various fibrinogen sources were obtained (FIG. 29). Tisseel™, stemCOAT®, EPF1, and EP2 exhibited confluent formation of a pigmented monolayer. Specifically, EPF2 exhibited fully monolayer attachment as low as 4 µg/mL. Neither Sigma® nor Millipore® fibrinogen resulted in confluent monolayers, as void spaces were detected in all samples, including concentrations as high as 2 mg/mL.

Example 2—Protocol for Retinal Pigment Epithelium Monolayer Formation

Human fibrinogen (e.g., Evicel®, 60 mg/mL) is diluted to 100 µg/mL using DPBS. 2 mL are plated onto a well of 6 well plate. The plate is incubated at 4° C. overnight. The fibrinogen solution is aspirated, and the plate is washed three times with DPBS. Human partially differentiated iPSC-RPE (passage 2) are plated onto the well at a concentration of $1 \times 10^6$ cells/cm². The cells are incubated at 37° C., 5% $CO_2$ overnight for attachment. Cells were plated in differentiation media as described elsewhere ((Johnson et al., Investig. Opthalmology Vis. Sci., 56:4619 (2015)). Media changes are performed on alternating days for up to about eight weeks. The cells are harvested and are prepared for analysis or use.

This protocol can produce RPE cells and RPE monolayers suitable for transplantation into a human eye using a xeno-free coating material. For example, an RPE monolayer is loaded into a surgical delivery device, and the human eye is prepared for surgery. Once prepared, the RPE monolayer is implanted into the subretinal space of the eye.

Example 3—Using Fibrinogen Coatings for Culturing and Differentiating iPSCs

The following was performed to develop a reproducible, quality-controlled product for coating of tissue culture plastic ware with human fibrinogen and for production of 3D human fibrin hydrogels. The product was assessed for having the ability to maintain iPSC cultures and for the ability to be used to differentiate iPSCs into different cell types such as RPE, endothelia, and cardiomyocytes.

Figures 20A, 20B, 20C:
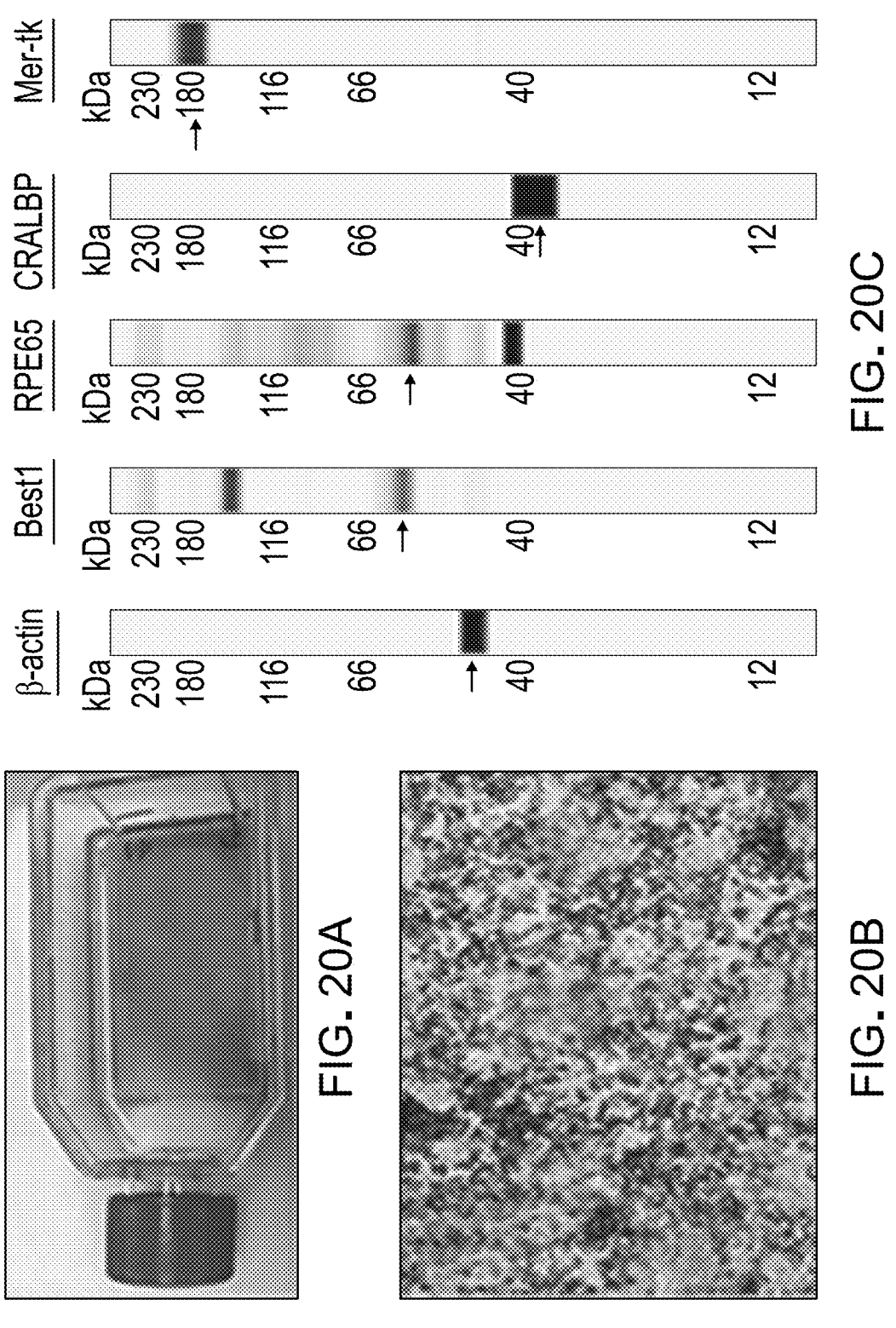
FIGS. 20A-C. 60-day old culture of iPSC-RPE grown on human fibrinogen. A) T25 flask of hiPSC-RPE cells grown on a human fibrinogen coated plate. B) Photomicrograph of hiPSC-RPE in the flask shown in A. Cobblestone appearance and pigmentation of cells were observed. Regions out of focus are domes resulting from fluid transport by the monolayer. C) Western blot using Proteinsimple® WES™ (a western blot assay for separating and analyzing proteins by size) for RPE markers. Arrows indicate location of bands for the marker indicated.
Figure 21A:
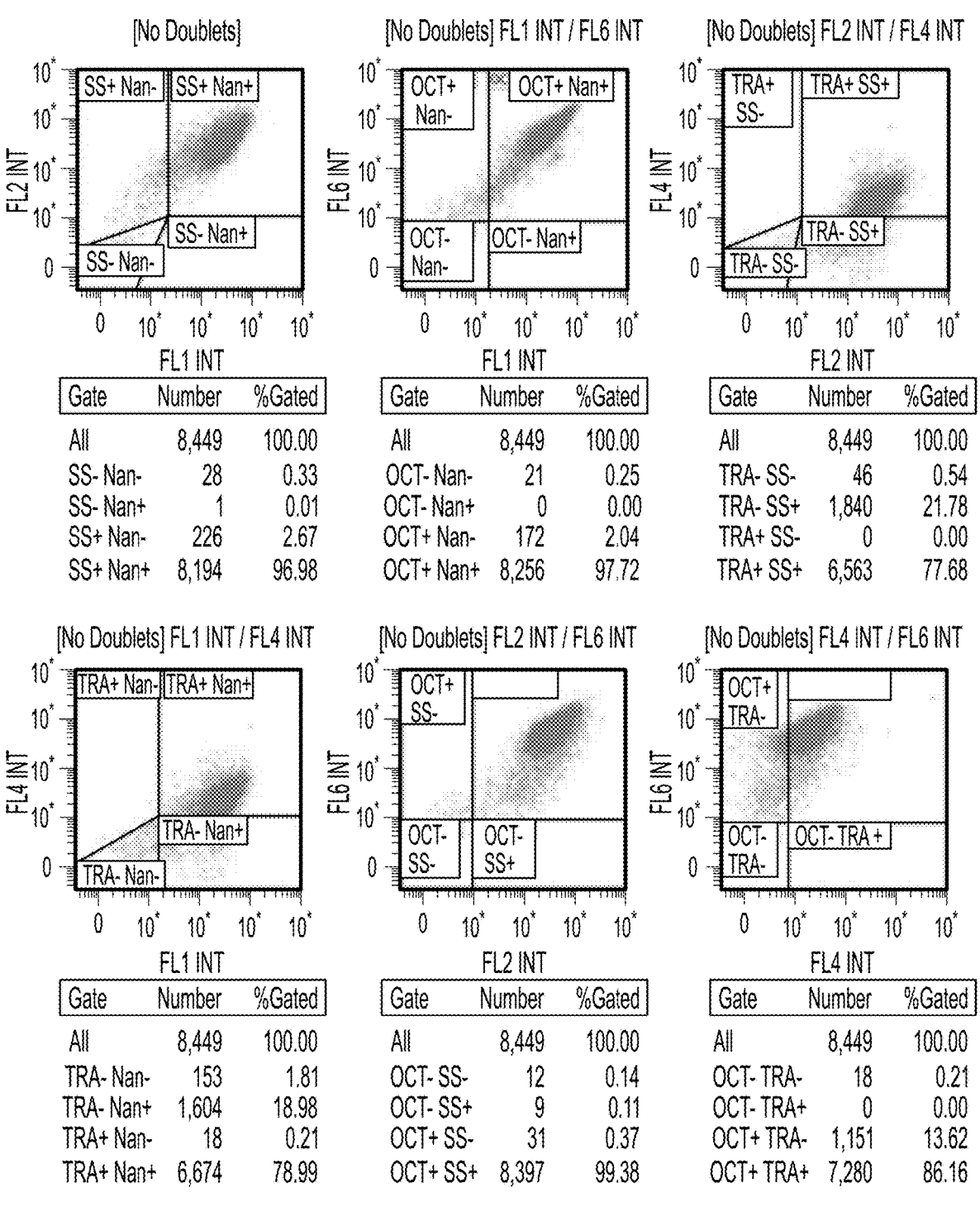
FIGS. 21A-D. Retention of pluripotency in an iPSC-line grown on plates coated with human fibrinogen. A) An example of pluripotency marker expression assessed using flow cytometry on cells grown on human fibrinogen. Each panel shows staining with two markers. B) Comparative % gating of iPSCs assessed using flow cytometry (Geltrex™ (a soluble form of basement membrane) vs. three human fibrinogen replicates). C) Expression of pluripotency markers by immunofluorescence. D) Demonstration that iPSCs grown on human fibrinogen retain the ability to differentiate down all three lineages using the STEMDIFF™ Trilineage differentiation kit (Stemcell Technologies).
Figure 21B:
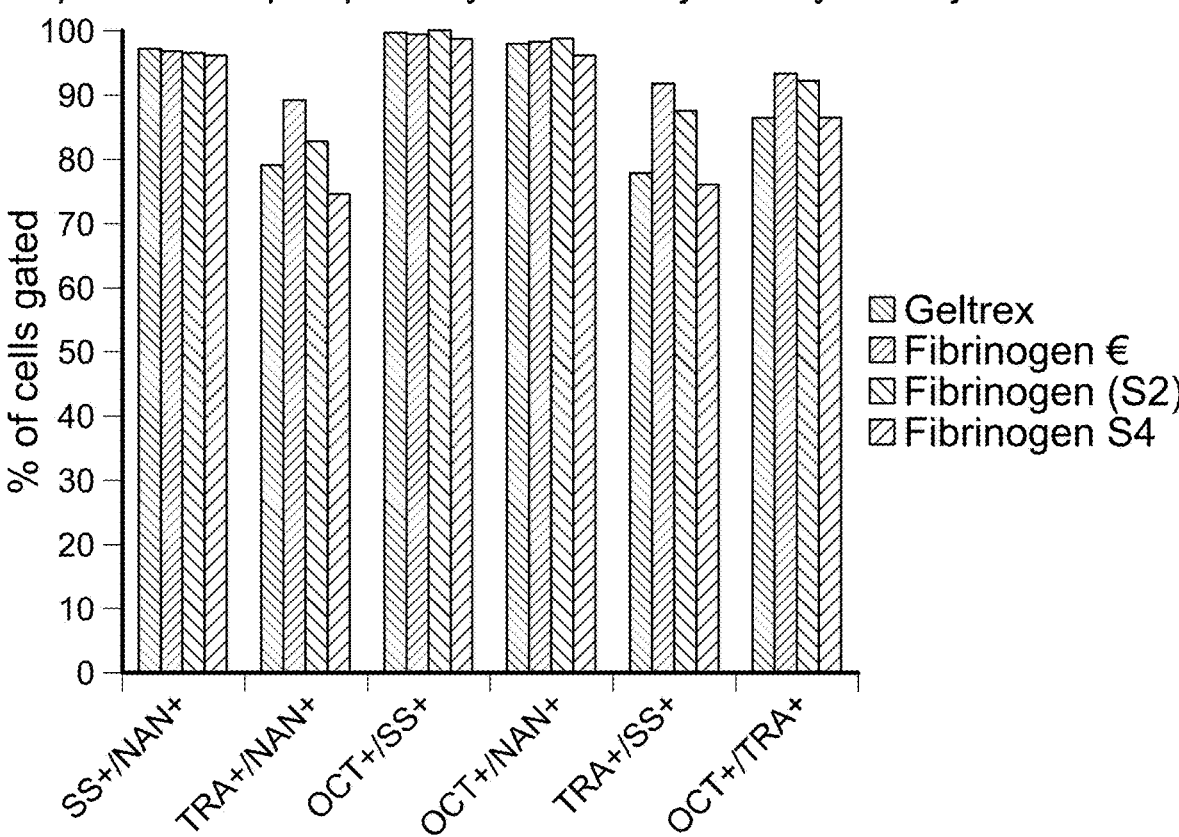
Figure 21C:
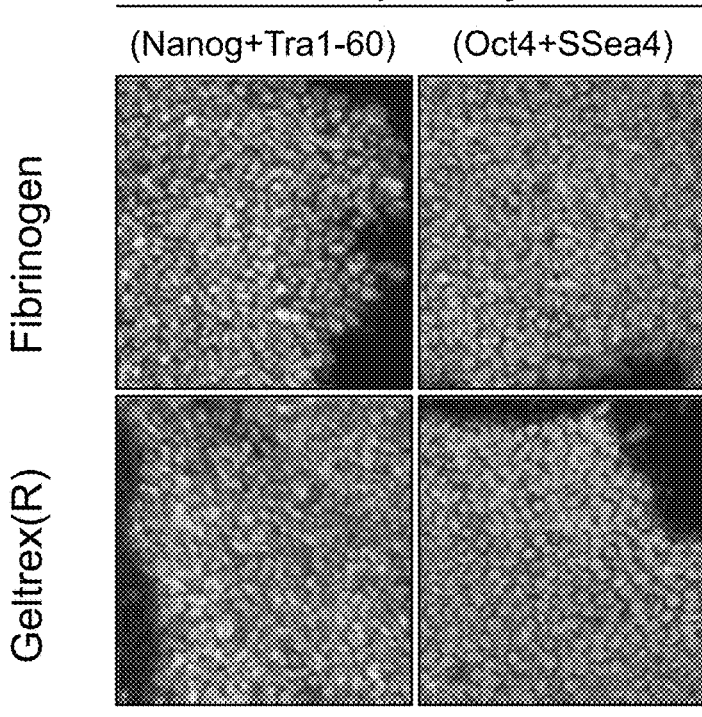
Figure 21D:
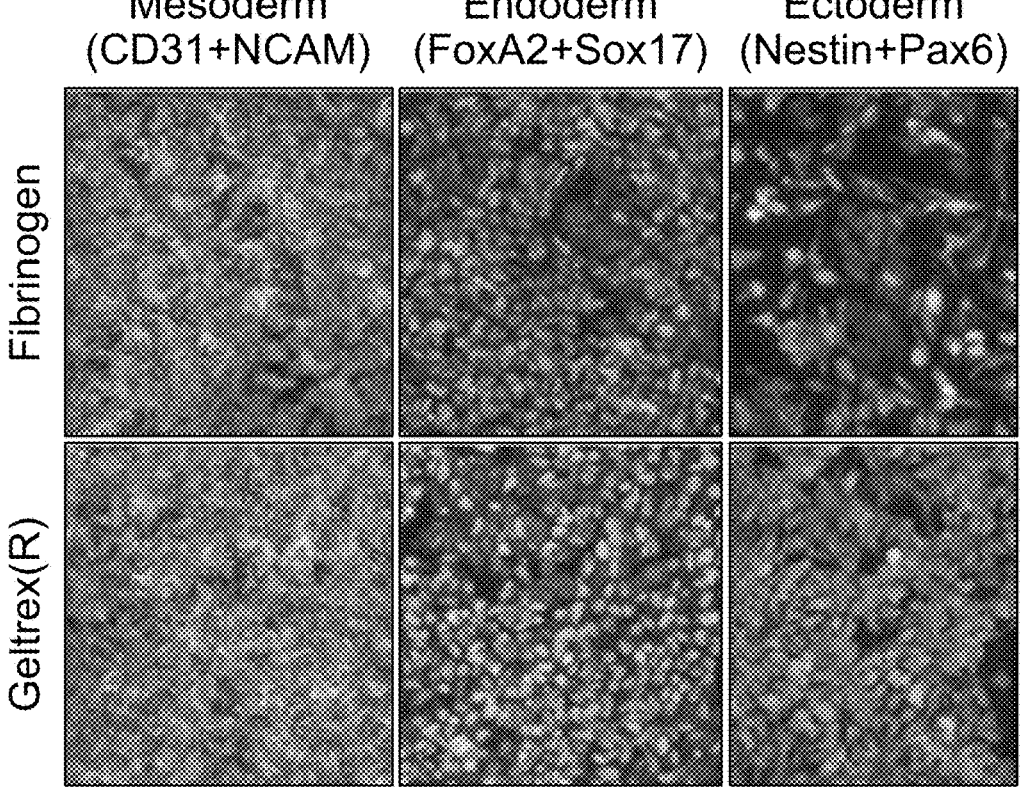

As described herein, human fibrinogen functioned as an effective coating for differentiation of iPSCs to RPE cells. See, also, FIGS. 20A-C. The following was performed to test how far back in the process of iPSC to RPE differentiation human fibrinogen can be used as a coating for tissue culture plastic ware. The human iPSC line 006-BIOTR-0001, clone 1 (cl1) grown on plates coated with human fibrinogen obtained from both ethanol precipitation and cryo precipitation maintained their pluripotency as determined by the continued expression of pluripotency markers at levels comparable to cl1 cells grown on Geltrex® (FIG. 21A-C). Furthermore, the cells retained the ability to undergo directed differentiation to endoderm, mesoderm, and ectoderm (FIG. 21D) using a trilineage differentiation endpoint assay. These results demonstrate that human fibrinogen can be used as a broadly applicable non-xenogeneic coating for tissue culture plastic ware used in the growth, expansion, and differentiation of human iPSCs.

Research grade human fibrinogen is typically sold as a lyophilized product. Denaturation of the material resulting from differences in production between manufacturers affects the ratio of clottable to total fibrinogen. There are also differences in residual buffer and salt concentrations as well as absolute purity between manufacturers. Finally, there is no guarantee of sterility or that the product is free of mycoplasma or other pathogens. These variables affect the properties of a fibrin hydrogel formed from these materials, causing difficulty in obtaining consistent results, and causing significant differences in concentration and efficiency when used to coat surfaces for tissue culture. The following is performed to develop a reproducible, quality controlled, human fibrinogen product for generating reproducible human fibrin hydrogels and for reproducibly coating tissue culture plastic ware.

Human plasma cryoprecipitate is used as a starting material to produce a highly enriched fibrinogen concentrate. The fibrinogen concentrate is assessed for purity, clottability, sterility, and other criteria. Following lot testing, the fibrinogen is used to generate fibrin gels and is expected to support iPSC-RPE growth as described herein. When successful, the material is titrated for use in coating plates.

Figure 22A:
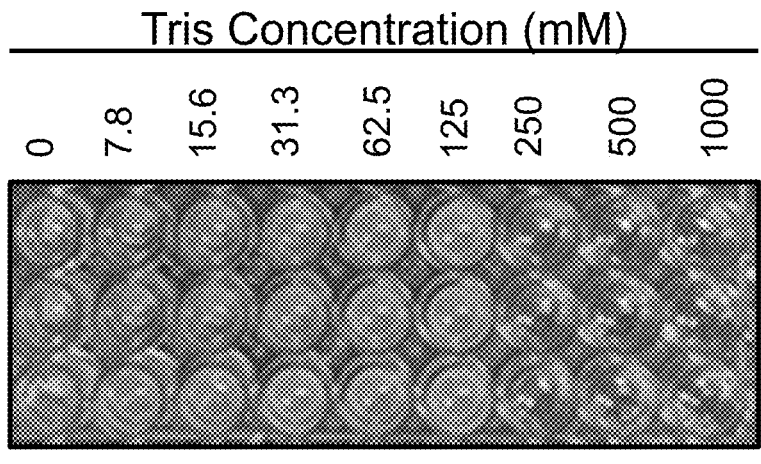
FIGS. 22A-B. Effect of Tris-HCl concentration on clottability of human fibrinogen. A) 2 mg/mL fibrinogen was diluted in Tris-HCl, pH 8.0 at the indicated concentrations, and clotting was stimulated by addition of thrombin. Transmitance was determined using a plate reader. B) Clotted fibrin has a lower transmittance than a fibrinogen solution. Clotting did not occur at Tris-HCl concentration ≥250 mM.
Figure 22B:
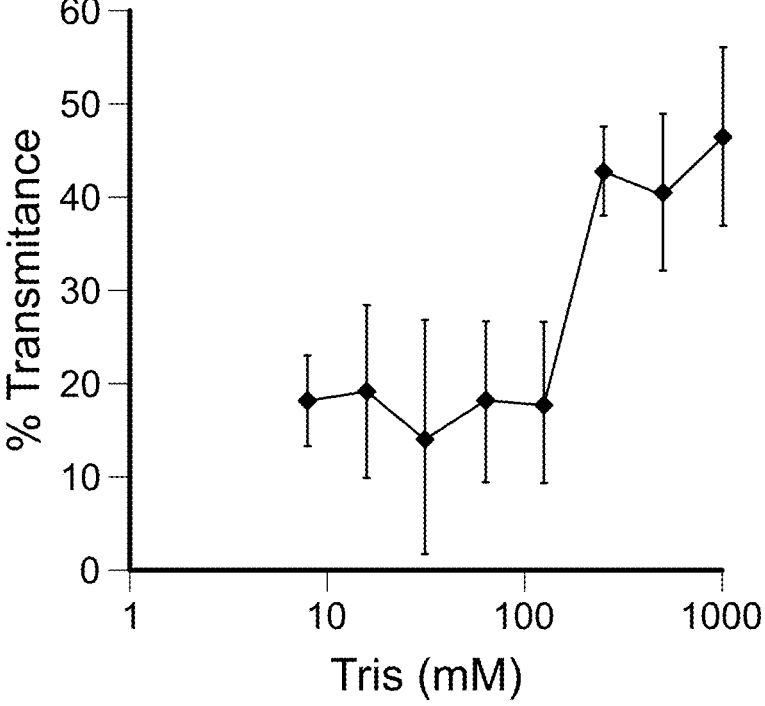

Human plasma cryoprecipitate is prepared by allowing frozen plasma to slowly defrost at 4° C. Fibrinogen, clotting factors, and fibronectin are precipitated in the blood bag forming a white "pellet" which is sedimented in a centrifuge. The material is directly obtained from Blood Banks and is usually supplied frozen with about 10-20 mL of plasma remaining with the pellet. Clinically, the plasma is used to reconstitute the pellet for therapeutic administration (e.g., to hemophiliacs). This procedure is as follows: Cryoprecipitate is defrosted overnight at 4° C., and the excess plasma is removed. The pellet is washed two times in ice-cold sterile saline to remove excess plasma proteins. The pellet is then solubilized in 5 mL of 250 mM Tris-HCl, pH 8.0. One Unit of cryoprecipitate pellet with a volume of about 5 mL is designed to contain about 500 to about 1500 mg of fibrinogen that is dissolved in a 10 mL volume after solubilization with a final concentration of 50-150 mg/mL fibrinogen in 125 mM Tris-HCl, pH 8.0. This concentration of Tris-HCl at pH 8.0 was confirmed to dissolve fibrinogen to a very high concentration without interfering with clottability (FIGS. 22A-B). For production of fibrin hydrogels, this concentration is desirable. For coating of surfaces for cell culture, a more dilute concentration is desirable and is determined. Following determination of clottable fibrinogen using the von Clauss method (Mackie et al., *Br. J Haematol.*, 121(3): 396-404 (2003); and Machin et al., *BMJ*, 307(6909):882-3 (1993)) on a Stago STart® coagulation analyzer (Stago, France), the fibrinogen is diluted to the appropriate concentration, is filtered through a 0.22 µm filter, and is dispensed aseptically into 10 and 50 mL bottles. The production process is scaled up as needed.

Additional lot testing is performed. Blood banks screen donors according to FDA CFR 21-1271 and directly test donated blood for HIV, HTLV, Zika, West Nile virus, Hepatitis B, and Hepatitis C. In addition to these tests for human pathogens, lots of fibrinogen produced are assayed in-house for pH, total protein concentration using a Biuret assay, albumin concentration using bromcresol purple, and mycoplasma using the AMP® Mycoplasma detection kit (Sartorius, Gottingen, Germany). Sterility is assayed for each lot to USP <71> standards by Steris (Mentor, OH). Endotoxin testing is performed.

Geltrex® and Matrigel® contain primarily mouse laminin enriched to about 80% purity. The fibrinogen preparations to be produced as described herein are designed to achieve a similar fibrinogen purity. Raw cryoprecipitate is typically composed of about 65% fibrinogen. For further enrichment, precipitation steps with protamine, glycine, and/or cold ethanol is incorporated into the production methods.

The starting material is clinical grade cryoprecipitate. It is delivered sterile and is presumably mycoplasma free. The preparation steps are performed in a cleanroom. Finally, the diluted fibrinogen preparation to be used for plate coating is sterile filtered through a 0.22 μm filter prior to bottling.

A successful fibrinogen preparation is determined to produce a lot of human fibrinogen that has an initial clottable fibrinogen concentration of >5 mg/mL, with purity in excess of 70%. The material is designed to pass sterility testing, is designed to be mycoplasma free, is designed to have a pH of 7.9-8.1, and is designed to form gels that support the growth and differentiation of iPSCs including iPSC-RPE cells.

The produced fibrinogen is tested for its ability to form gels as described elsewhere (Gandhi et al., *Acta Biomater.*, 67:134-146 (2018)), and the ability of iPSC-RPE to adhere to the gel produced is determined. In particular, the produced fibrinogen is compared side-by-side to Geltrex®, Matrigel®, and recombinant human laminin 521 as a coating for the passage of iPSCs and for the differentiation of iPSCs into RPE, endothelia, and cardiomyocytes. The experiments are used to validate that the produced fibrinogen product can serve to replace laminin in the culture of iPSCs and iPSC derived cell types.

The following is performed as a titration for plate coating for adhesion and growth of iPSCs. As described herein, obtained data demonstrated that plate coating was accomplished by simply adding a fibrinogen solution to the plate and incubating for 1 hour at 37° C. In those completed studies, 100 μg/mL of fibrinogen was used for culture of iPSC-RPE, but this was not sufficient for iPSC attachment. As shown in FIGS. 21A-D, plates were coated with a solution containing 500 μg fibrinogen/mL using a volume of 250 μL/cm². This worked for the first preparation of fibrinogen prepared from human plasma as indicated herein, and for fibrinogen obtained from a clinical fibrin tissue "glue". It did not work for research grade fibrinogen obtained from Sigma-Aldrich® or Millipore®/EMD, which were supplied as a lyophilized powder.

To determine the minimum concentration of clottable fibrinogen necessary for culture of iPSCs and cell differentiated from iPSCs, the following is performed. Fibrinogen is prepared as indicated herein and is diluted to a concentration of 2 mg/mL. A set of 2-fold serial dilutions is prepared to as low as 0.03125 mg/mL, and 9 wells of each of 3×12-well multiwell plates are coated with these solutions. The remaining 3 wells in each plate are coated with either Geltrex® (42 μg/mL)), Matrigel® (2 mg/mL), or Human laminin 521 (30 μg/mL) using dilutions/concentrations that were shown previously to work. Following coating, iPSCs are plated in each well of each plate. Entire wells are photographed daily, and colonies are counted using a Molecular Devices Spectramax® 3 with Minimax® 300 cytometer attachment. It is possible to manually clean or remove iPSC colonies that appear to be undergoing spontaneous differentiation on a daily basis. For this experiment, however, the wells are not cleaned. Instead, a blinded observer is instructed to count the number of colonies that appear to be undergoing spontaneous differentiation from the photographs according to a uniform set of criteria. At the end of 7 days, number of colonies is graphed as compared to the number of colonies undergoing spontaneous differentiation for each well of each plate. The results are used to determine a fibrinogen concentration that is minimally necessary to support adhesion and proliferation of iPSCs without a rate of spontaneous differentiation exceeding that observed when laminin is used to coat plates. To control for lot-to-lot variability, three independently produced lots of human fibrinogen are tested and used to define a threshold as the minimum concentration effective for all three lots tested.

Figure 41:
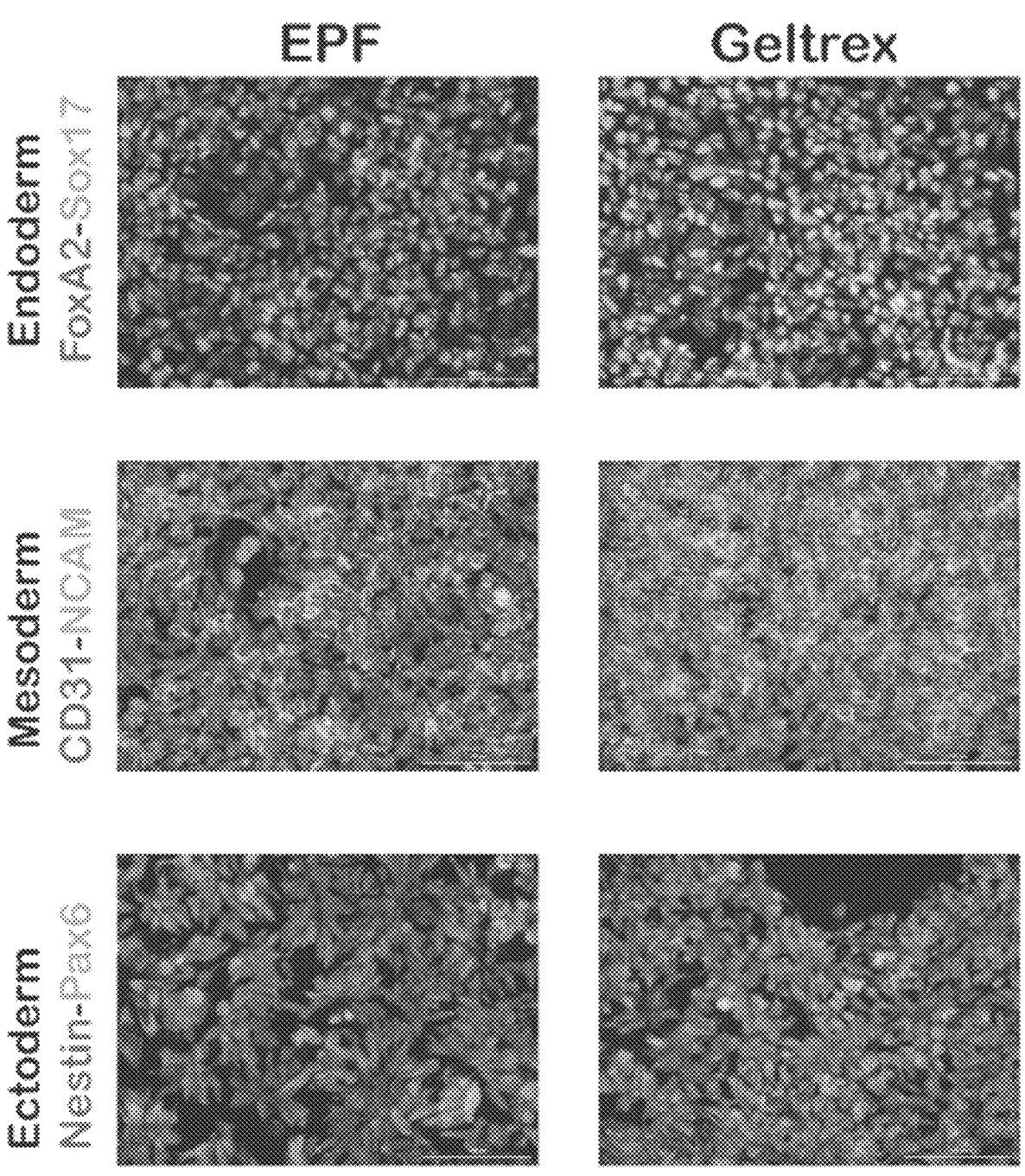
FIG. 41 contains photographs of immunofluorescent staining of iPSCs after undergoing tri-lineage differentiation. Endoderm differentiation was confirmed using FoxA2 and Sox17 staining on both EPF and Geltrex™ cultured cells. Mesoderm differentiation was confirmed using CD31 and NCAM staining on both EPF and Geltrex™ cultured cells. Ectoderm differentiation was confirmed using Nestin and Pax6 staining on both EPF and Geltrex™ cultured cells.

To determine if fibrinogen preserves the pluripotency of iPSCs, pluripotency is tested using iPSCs after multiple passages on fibrinogen. 60 mm dishes are coated with an optimal concentration of fibrinogen determined as described herein, and iPSCs are plated on them from 5 iPSC lines derived from different donors. Cells are serially passaged 5 times with cells from each passage undergoing testing to determine if they retain expression of pluripotency markers using flow cytometry as described for FIGS. 21A-D. Similarly, FIG. 41 shows qualitative staining for pluripotency markers on iPSC cultured on EPF and Geltrex™. Following the 5th passage, the cells are also immunofluorescently stained for pluripotency markers, are karyotyped, and are assayed for the capacity to undergo directed differentiation to ectoderm, mesoderm, and ectoderm using the STEMDIFF™ Trilineage differentiation kit (Stemcell Technologies).

To titrate plate coating for adhesion and growth of cells differentiated from iPSCs, the experiment described above is performed replacing iPSCs with iPSC-derived RPE, endothelial cells, or cardiomyocytes. These cells are used to represent cells differentiated from three lineages: ectoderm (RPE), endoderm (endothelia), and mesoderm (cardiomyocytes). The results are used to identify the minimal concentration of fibrinogen for adhering and supporting each cell type. RPE, endothelial cells, and cardiomyocytes are obtained from 2 iPSC lines (cl1 and IMR90 clone 4) using established differentiation protocols but substituting fibrinogen as the plate coating in each step. The two cell lines are chosen because they generate all three cell types on laminin, the lines originate from different sources, and they are produced using different reprogramming systems (Sendai virus and retrovirus, respectively).

A successful result is achieved when human fibrinogen is demonstrated to be equal to or superior to laminin in the adhesion and growth of iPSCs and is demonstrated to be equivalent or superior for differentiation of iPSCs to cells of ectodermal, endodermal, and mesodermal origin.

Example 4—Fibrinogen Coatings for Culture and Differentiation of iPSCs

Cells

The CLR-0001-BIOTR iPSC line was used between passages 10 and 20 (Johnson et al., *Investig. Opthalmology Vis. Sci.*, 56:4619 (2015); and Marmorstein et al. *Sci. Rep.*, 8:4487 (2018)). An additional line, CLR-0004 from WiCell®, was also used (Johnson et al., *Investig. Opthalmology Vis. Sci.*, 56:4619 (2015)). mTESR™ (Stem Cell Technologies) was used for iPSC growth, and mRESLR (Stem Cell Technologies) was used to dissociate cells for passage. Passage was performed on iPSC clusters, and replated at an approximate density of 20-40% confluency to maintain pluripotency and amplification.

Fibrinogen Extraction

Fibrinogen was extracted using standard methods, including ethanol precipitation (Dietrich et al., *Tissue Eng. Part C Methods.*, 19:216-226 (2013)) and cryoprecipitation (Sparrow et al., *Methods Mol. Biol. Clifton NJ.*, 728:259-265

(2011)). Once precipitated, fibrinogen was reconstituted in various molarities of Tris-HCL, TBS, PBS, and citrate buffered saline. Samples were sterile filtered and aliquoted as a stock solution to prevent multiple freeze-thaws. Commercially available fibrinogen (Evicel®; Ethicon) also was used for comparison.

Clottable fibrinogen concentrations were confirmed using the Clauss method. Total protein concentration was determined using a commercial BCA assay (Pierce Technologies), using Evicel® known total protein concentration value as a standard. For purity, an SDS-PAGE gel was run using a 10% mini protean gel (Bio-Rad) at 120V, 0.1 A for 1.5 hours. The gel was removed from the cartridge, stained with a coomassie blue solution overnight (Bio-Rad), and washed multiple times in destaining solution (Bio-Rad). The gel was then imaged using a GelDOC® (Bio-Rad; a gel documentation system).

Plate Coating

Fibrinogen stock solutions from various sources were thawed at 37° C. and diluted to working concentrations in respective buffers. Evicel® was diluted in PBS. A plating density of 0.3125 mL/cm² of surface area was used. Plates were incubated at 37° C. for a minimum of 2 hours prior to use. After incubation, plates were washed 3× with PBS prior to plating iPSCs.

Geltrex™ (Thermo Fisher) was used as a positive control. Frozen aliquots of Geltrex™ were thawed on ice, diluted 1:240 in DMEM/F12 media, and plated at a density of 0.3125 mL/cm² of surface area. Plates were incubated for at least 2 hours at 37° C. After incubation, the plates were aspirated and cells were plated immediately.

FACS

Cells cultured on various coated surfaces were cultured for at least 48 hours prior to performing flow cytometry. Cells were lifted off using TrypLE™ (Life Technologies; a recombinant enzyme), up to 5 minutes at 37° C., centrifuged at 800 g for 4 minutes, resuspended in PBS to split into 2 tubes for unstained control, and re-centrifuged. Cells were fixed in PerFix-nc™ (Beckman Coulter; a no centrifuge assay kit) per manufacturers protocol. Cells to be stained were mixed with staining solution consisting of permeabilizing reagent, 1:10 Alexa 488 (Alexa Fluor® 488 dye) anti-human Nanog (BD), 1:10 Alex 647 anti-OCT 3/4 (BD), 1:10 PE anti-SSEA4 (BD), and 1:10 PerCP-Cy5.5 anti-human TRA1-60 (BD). Cell clumps were removed by allowing the cell slurry to settle prior to running. Samples were run on Gallios® (Beckman Coulter; a flow cytometer), using 4 channels. A total of 1,000 cells were counted, with double positive cells required for confirmed expression.

Differentiation iPSCs were passaged from 60 mm plates using Accutase™ (Innovative Cell Tech; San Diego, CA; a cell detachment solution) with the respective coating material onto 6 well plates (Ecto) or 24 well plates (Endo, Meso) with respective coating material. Ectoderm differentiation was performed using the STEMdiff™ Neural Induction Medium (Stem Cell Tech) per manufacturer's protocol. Y-27632 (RND Systems) was added to the day 0 media only. After 9 days of culture, the cells were passaged from the 6 well plate using Accutase™ and replated onto a 24 well plate. Differentiation was completed using the Neural induction Medium until roughly 70% confluent. Endoderm differentiation was performed using the STEMdiff™ Definitive Endoderm Kit (Stem Cell Tech) per manufacturer's protocol. After day 5, cells were fixed in 4% PFA. Mesoderm differentiation was performed using the StemDiff™ Mesoderm Induction Medium per manufacturer's protocol. After day 5, cells were fixed in 4% PFA.

Immunofluorescent Staining

Fixed iPSCs were stained for pluripotency markers to assess clonal variation between culture substrates. Fixed cells were permeabilized in 0.2% Triton™-X 100 (Sigma-Aldrich®; a non-ionic surfactant) for 30 minutes at room temperature prior to incubation in blocking solution (DAKO). Respective wells were incubated with one of the following primary antibody combinations for 1 hour at room temperature: (A) 1:200 Rabbit anti-Oct 3/4 (Abcam) and 1:100 Mouse anti-SSea4 (Abcam), or (B) 1:100 Rabbit anti-Nanog (Cell Signaling) and 1:100 mouse anti-Tra1-60 (Abcam). Wells were washed with washing solution (DAKO) thrice. Then, the secondary antibody cocktail was incubated for 30 minutes at room temperature: 1:200 Anti-rabbit Alexa 594 (Alexa Fluor® 594 dye) and 1:300 anti-mouse Alexa488 (Alexa Fluor® 488 dye). Wells were again washed, stained with DAPI for 5 minutes and imaged using a Cytation™ 5 Imager (BioTek).

Differentiated cells were stained using a similar protocol, but modified to include the following primary antibodies: (Ecto) 1:20 Sheep anti-Pax6 (RND Systems), (Endo) 1:200 Rabbit anti-FoxA2 (Cell Signaling), or (Meso) 1:200 Rabbit anti-MixL1 (Millipore®). Images were analyzed using Gen5 Imaging Prism (BioTek; Winooski, VT) software, and differentiation efficiency was calculated as the total dual-stain positive cells divided by total DAPI positive cells.

Gel Culture

Fibrin gels were made as described elsewhere (Gandhi et al., *Acta Biomater.*, 67:134-146 (2018)). Briefly, a mixture of 30 mg/mL fibrinogen and 100 U/mL thrombin (final concentration) was mixed in a well of a 12 well plate, and a custom polycarbonate mold with parafilm was used to flatten the gel within the well. The gel was allowed to fully polymerize for 2 hours at 37° C. prior to washing with PBS and seeding the iPSCs onto the gel.

Figure 30:
FIG. 30 contains photographs of iPSC cells being cultured on fibrin in mTESR™ (a cGMP, stabilized feeder-free maintenance medium) media without aprotinin supplement after being cultured for 2 days. iPSC colonies were plated at medium density (1:10 dilution from a confluent plate) onto a 12 well plate with a fibrin hydrogel formed with 30 mg/mL fibrinogen and 100 U/mL thrombin. The iPSC appear as colonies.
Figure 30:

Results iPSCs on Fibrin iPSCs were successfully cultured on top of fibrin hydrogels. FIG. 30 shows iPSC colonies cultured on a fibrin hydrogel made with 30 mg/mL fibrinogen and 100 U/mL thrombin, without supplemented aprotinin. iPSC colonies expanded over time. With heavier plating, iPSCs formed a confluent monolayer. Without aprotinin, there were many strain lines within the gel, suggesting a mechanical force exerted by the iPSCs. Without aprotinin, the gel did not appear to be significantly degraded when reaching confluency.

Figure 31:
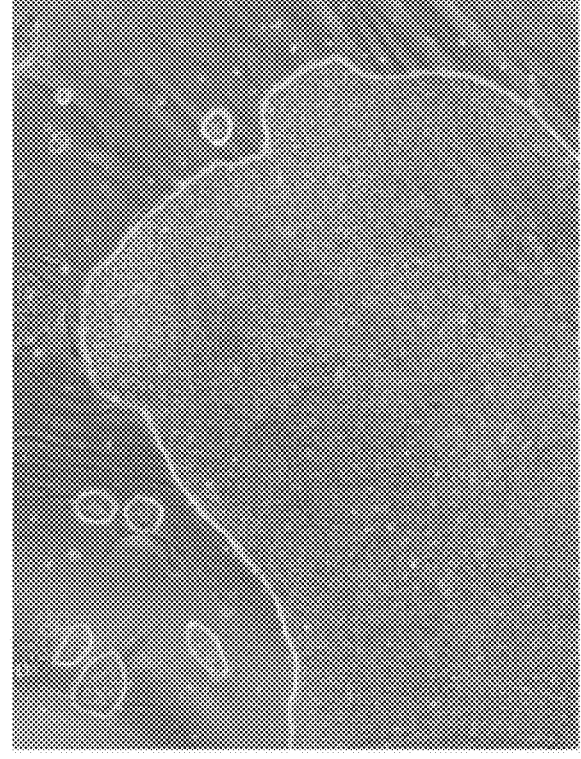
FIG. 31 contains photographs of iPSC cells being cultured on fibrin in mTESR™ media with supplemented 50 U/mL aprotinin after being cultured for 2 days. iPSC colonies were plated at medium density (1:10 dilution from a confluent plate) onto a 12 well plate with a fibrin hydrogel formed with 30 mg/mL fibrinogen and 100 U/mL thrombin. The iPSC appear as colonies.
Figure 31:

FIG. 31 shows iPSC colonies cultured on a similar fibrin hydrogel, with supplemented 50 U/mL aprotinin. Similarly, iPSC colonies expanded over time, forming monolayers in samples with heavier plating. The addition of aprotinin did not appear to prevent strain lines within the gel. With aprotinin, the gel does not degrade up to at least 1 month.

SDS-PAGE Gel of Various Fibrinogen

Figure 32:
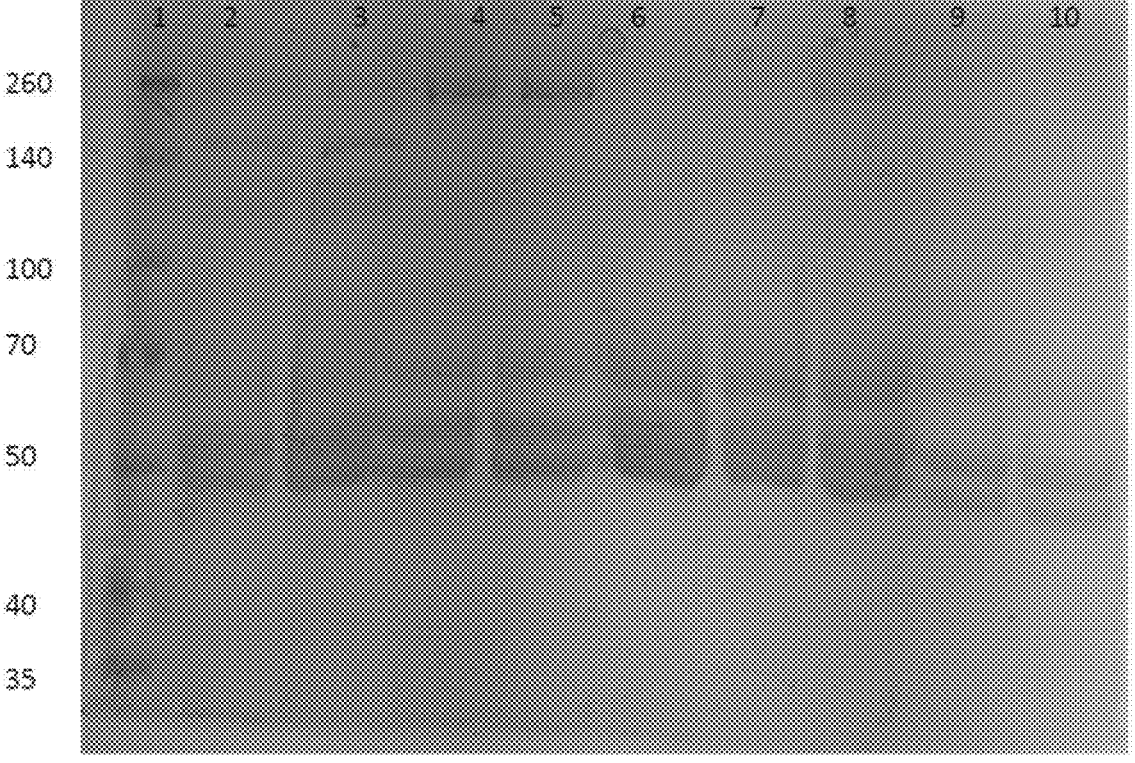
FIG. 32 contains a photograph of an SDS-PAGE gel of various preparations of fibrinogen. Lane 1 is a molecular weight ladder; lane 2 is ethanol precipitated fibrinogen at 1:40 dilution; lane 3 is ethanol precipitated fibrinogen at 1:30 dilution; lane 4 is Evicel® (cryoprecipitated fibrinogen) at 1:110 dilution; lane 5 is Evicel® at 1:100 dilution; lane 6 is a second batch of ethanol precipitated fibrinogen at 1:6 dilution; lane 7 is second batch of ethanol precipitated fibrinogen at 1:8 dilution; lane 8 is cryoprecipitated fibrinogen at 1:20 dilution; lane 9 is cryoprecipitated fibrinogen depleted of plasminogen, von willebrand factor, and fibronectin at 1:25 dilution; lane 10 is the depleted, cryoprecipitated fibrinogen at 1:22 dilution.

To determine the qualitative purity of the various fibrinogen preps, an SDS-PAGE gel was run and stained with coomassie blue. Each of the fibrinogen preps was successful to culture iPSCs. Lanes 9 and 10 represent the positive control, a cryo-precipitated fibrinogen depleted of plasminogen, von willebrand factor and fibronectin (FIG. 32). Fibrinogen appears characteristically as 3 bands, alpha (67 kDa), beta (54 kDa), and gamma (47 kDa) (FIG. 32). All experimental samples exhibited a similar characteristic profile of fibrinogen. Lanes 2 and 3 represented an ethanol precipitated fibrinogen prep (EPF1) (FIG. 32). This includes multiple bands around 260 kDa, 150 kDa, and 120 kDa. Fibronectin is a common component of plasma precipitates and is found as a band near 260 kDa. Lanes 4 and 5 represent a commercially available cryo-precipitated fibrinogen (Evicel®, EVI) (FIG. 32). Lanes 6 and 7 were for a second, distinct prep of ethanol precipitated fibrinogen (EPF2) (FIG. 32). This sample appeared to have a much lower fibronectin concentration. This also was the sample that was able to successfully plate iPSCs at 100 μg/mL. Finally, lane 9 represents a cryo-precipitated fibrinogen (CPF1) (FIG. 32).

Figure 39:
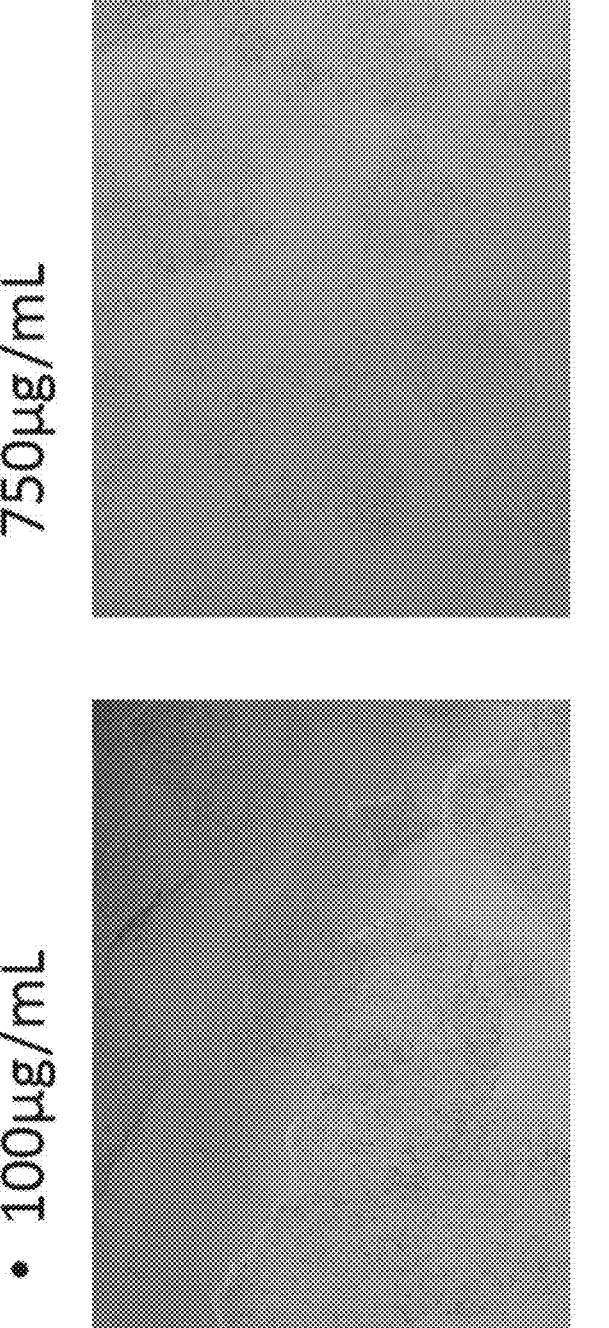
FIG. 39 contains photographs of iPSC cells being cultured on fibrinogen coated plate in mTESR™ media without supplement after being cultured for 2 days. iPSC colonies were plated at medium density (1:10 dilution from a confluent plate) onto a 12 well plate coated with 100 µg/mL or 750 µg/mL fibrinogen. The fibrinogen used here was obtained by ethanol precipitation of frozen human plasma. The iPSC appear as colonies.

Plurpotency Maintenance of iPSCs on Fibrinogen iPSCs were cultured on the various preparations of fibrinogen. Using EPF2 resulted in the lowest concentration with successful iPSC attachment. For example, FIG. 39 shows iPSCs attached to a plate coated with 100 ug/mL of fibrinogen using the EPF2 condition. A 700 ug/mL fibrinogen concentration showed similar attachment.

Figure 33A:
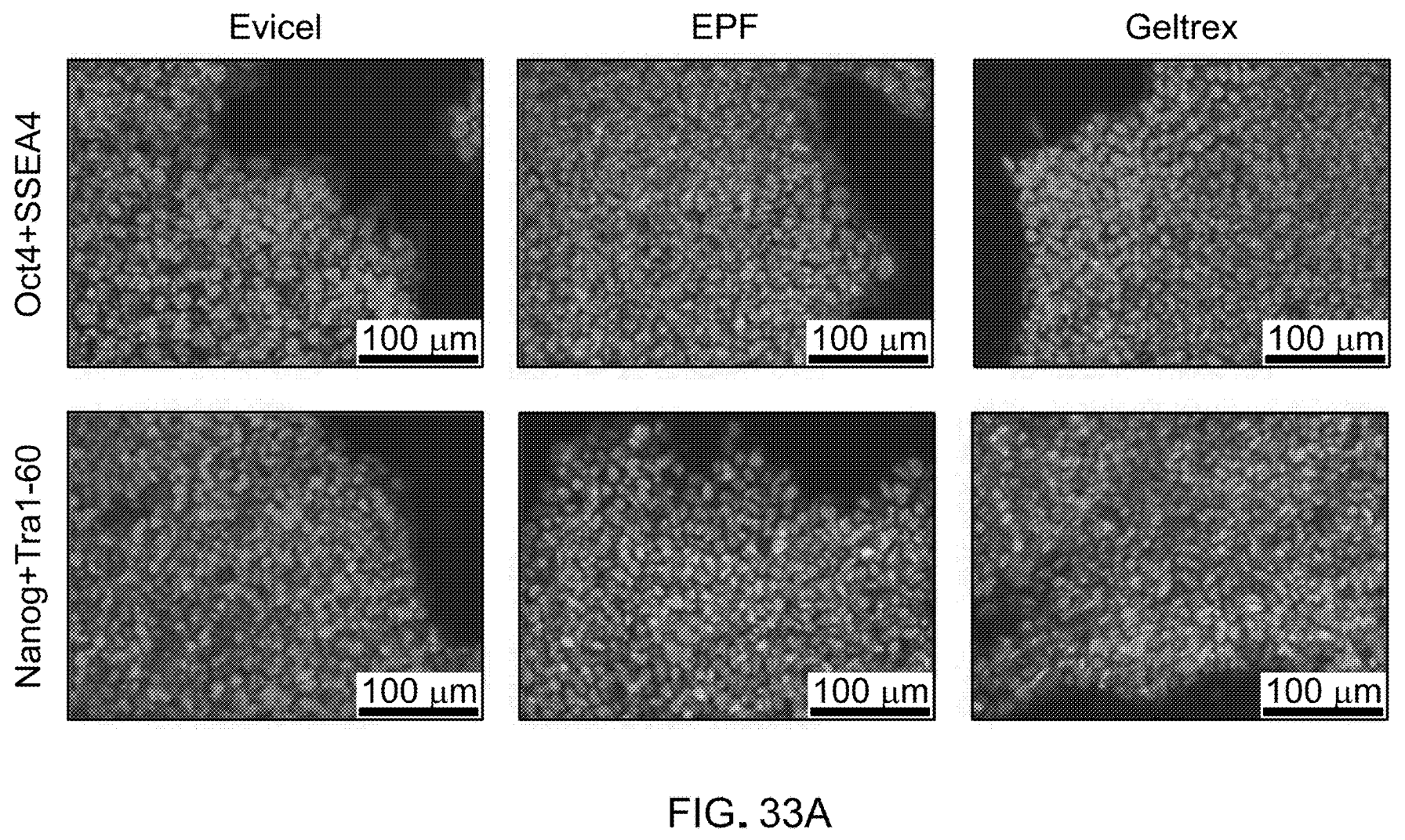
Figure 33B:
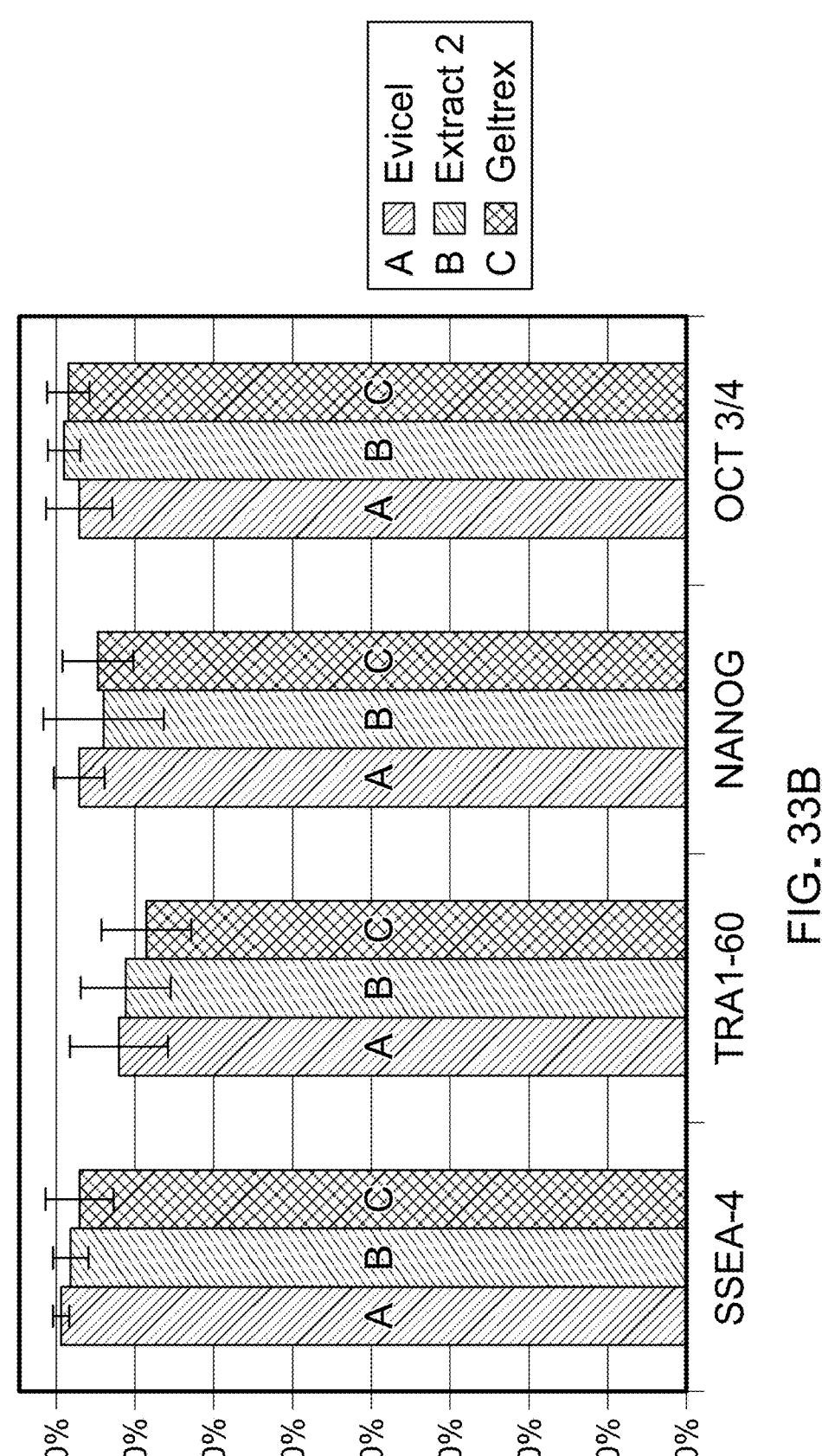

Using fibrinogen as a coating material for iPSC colonies was confirmed to maintain pluripotency markers. Immunofluorescent staining of iPSC colonies on EVI, EPF1, and Geltrex™ (GT) exhibited positive staining for Oct4, SSea4, Nanog and Tra1-60 throughout individual colonies (FIG. 33A). FACs analysis was used on minimum of 1,000 cells to quantify individual cell expression of pluripotency markers (FIG. 33B). A marker was considered positive only if double positive with all other markers. Oct4 expression was positive in 97.4±4.1% on EVI, 98.9±1.8% on EPF1, and 98.4±2.4% on GT. SSea4 expression was positive in 99.3±1.2% on EVI, 98.4±2.3% on EPF1, and 97.1±4.3% on GT. NANOG expression was positive in 97.5±3.3% on EVI, 94.1±7.6% on EPF1, and 94.9±4.5% on GT. TRA1 60 expression was positive in 92.2±6.1% on EVI, 91.4±5.5% on EPF1, and 88.6±5.5% on GT.

Differentiation of iPSCs on Fibrinogen

Figure 40:
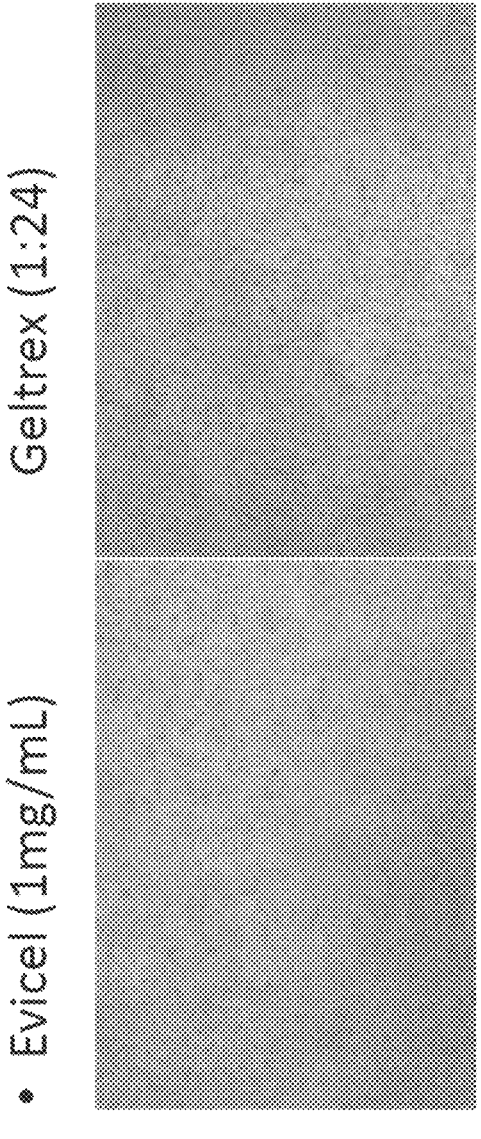
FIG. 40 contains photographs of iPSC cells being cultured on fibrinogen coated plate in mTESR™ media without supplement after being cultured for 3 days. iPSC colonies were plated at high density (1:3 dilution from a confluent plate) onto a 12 well plate coated with 1 mg/mL fibrinogen or Geltrex™ as a positive control. The fibrinogen (Evicel®) used here was obtained by cryoprecipitation. The iPSC appear as confluent monolayer.

Prior to differentiation, the ability to generate iPSC monolayers on fibrinogen coated plates was determined. FIG. 40 shows that iPSCs were able to form confluent monolayers when cultured on fibrinogen, compared to a Geltrex™ positive control.

iPSCs cultured on fibrinogen were differentiated to the three germ lines using a commercial kit (STEMdiff™ Trilineage Differentiation Kit, StemCell Technologies). After induction in endoderm, mesoderm, and ectoderm differentiation media, iPSCs were fixed and stained for respective markers. iPSCs cultured on EPF showed expression on FoxA2 and Sox17 after endoderm induction, CD31 and NCAM after mesoderm induction, and Nestin and Pax6 after ectoderm induction. iPSCs cultured on Geltrex™ were used as a positive control and were positive for all markers.

Different iPSC Clone

Figure 34:
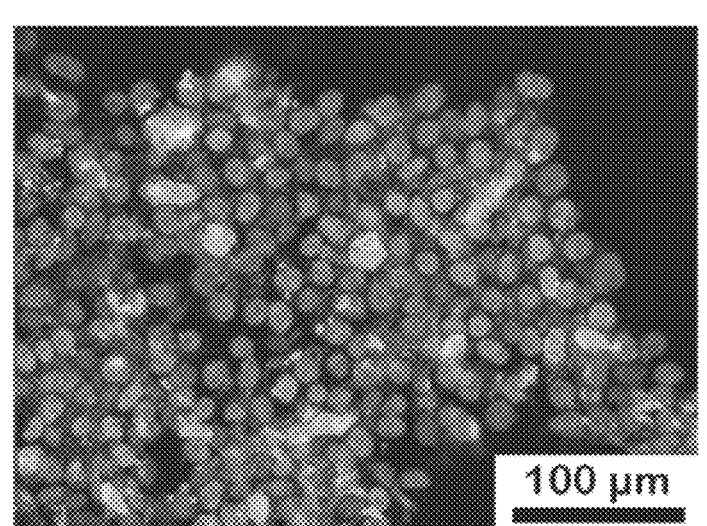
FIG. 34 contains photographs of pluripotency markers using a different iPSC line, WiCell® clone 4, grown on fibrinogen coated plates. Immunofluorescence was performed for pluripotency factors Oct4, Ssea4, Nanog, and Tra1-60 in iPSCs cultured on EPF.
Figure 34:
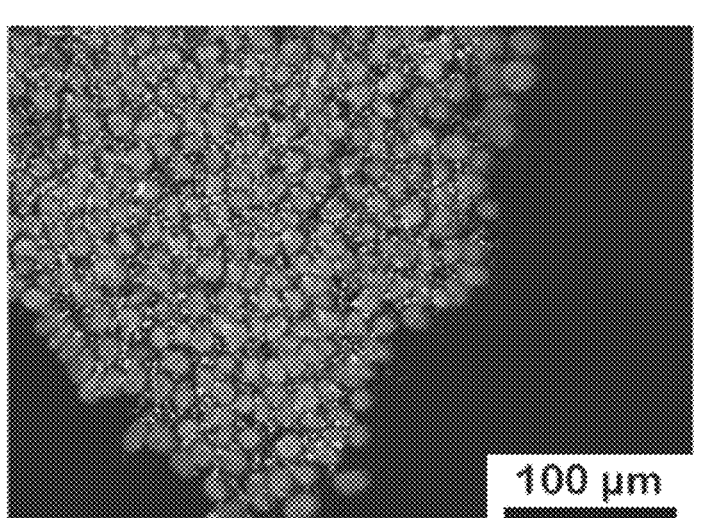
Figure 35:
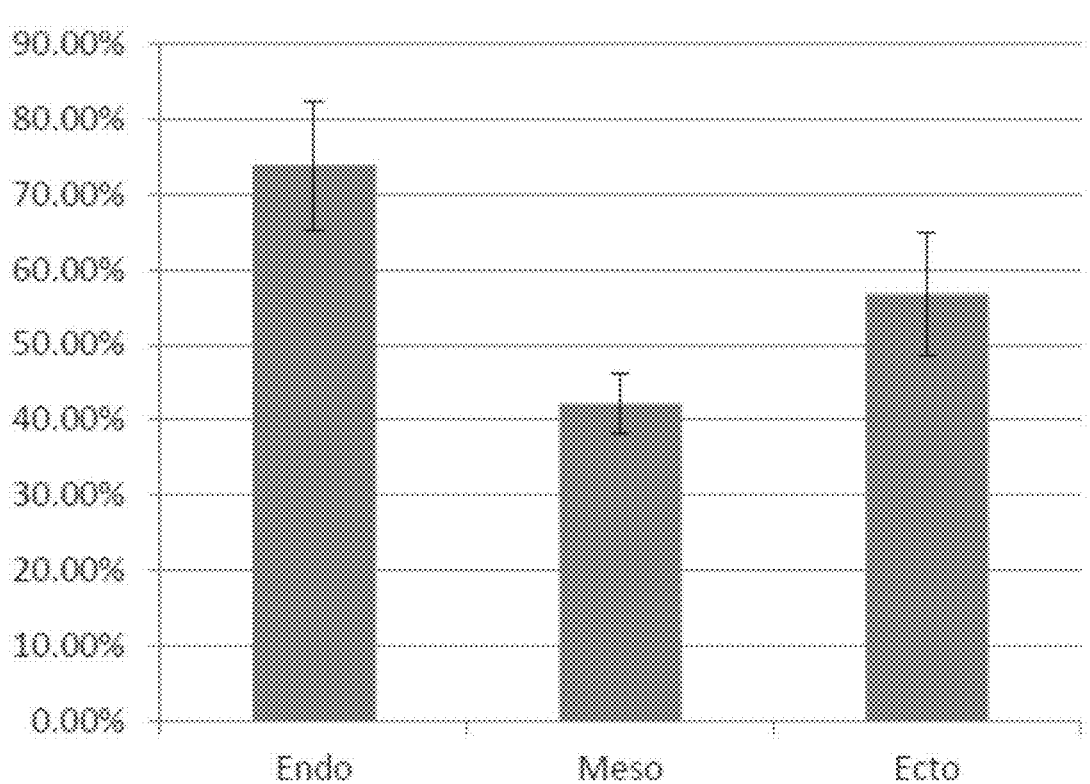
FIG. 35 contains a graph of tri-lineage differentiation analysis of iPSCs (WiCell® clone 4) cultured on fibrinogen. Endoderm differentiation was successful in 73.91±8.58% of iPSCS on fibrinogen coated plates. Mesoderm differentiation was successful in 42.17±3.91% of iPSCS on fibrinogen coated plates. Ectoderm differentiation was successful in 56.69±8.15% of iPSCs on fibrinogen coated plates.

To validate that the ability to culture iPSCs on fibrinogen was not inherent to the cell line, a commercially available iPSC cell line (WISCi004-A-1) described elsewhere (Srikanth et al., *Cell Rep.*, 12:1414-1429 (2015); and Zeng et al., *PloS One,* 5:e11853 (2010)) was used. WISCi004-A-1 successfully maintained pluripotency when cultured on fibrinogen coated plates. Immunofluorescence revealed positive staining of Oct4, SSea4, Nanog, and Tra1-60 (FIG. 34). Further, the iPSCs were differentiated to the three germline lineages. With the WISCi004-A-1 line cultured on fibrinogen, endoderm differentiation was achieved in 73.9±8.6% of iPSCs, mesoderm was achieved in 42.2±3.9% of iPSCs, and ectoderm was achieved in 56.7±8.2% of iPSCs (FIG. 35).

Example 5—iPSC-Endothelial Cells Differentiation and Culture on Fibrinogen-Coated Plates iPSC-EC Differentiation The CLR-0001-BIOTR iPSC line was used between passages 10 and 15. A 6 well plate was coated with 1 mg/mL fibrinogen reagent, using 2 mL/well and incubating at 37° C. for 2 hours prior to use. iPSC-EC differentiation was performed as described elsewhere (Orlova et al., *Nat. Protoc.,* 9:1514-1531 (2014)). Briefly, iPSC colonies were broken into 0.5-1 mm diameter pieces, and 5-8 colonies were plated per cell. iPSC were cultured with mTeSR™1 medium for 2 days, and then replaced with Mesoderm induction medium (BPEL (Orlova et al., *Nat. Protoc.,* 9:1514-1531 (2014)) base supplemented with 25 ng/mL Activin A (RND Systems), 30 ng/mL BMP4 (Miltenyi Biotec), 50 ng/mL VEGF (RND Systems), and 1.5 μM CHIR (RND Systems)). After 2 days, the media was replaced with vascular specific medium (BPEL base supplemented with 50 ng/mL VEGF and 10 μM SB431542 (RND Systems)). The vascular specific medium was replenished after 4 days, and again after an additional 2 days.

After EC islands appeared, the iPSC-EC were purified using magnetic beads. CD31-labeled beads (Thermo Fisher) were suspended in 0.1% BSA in DMEM, using 21 μL of beads per well. The cells were washed with PBS before incubating the beads with the cells for 30 minutes at room temperature with slight agitation. The beads were then washed, and the cells were lifted with TrypLE™ (Thermo Fisher), incubating for 5 minutes at room temperature. The reaction was stopped with FACSB-10 solution (10% FBS in FACS buffer). The cell solution was strained using a 100 μm cell strainer. The cells were placed in a magnetized column, and washed 2× with FACSB-10 and 2× 0.1% BSA in DMEM. The remaining cells were resuspended after removing from the magnetic column in Endothelial Growth Media (EGM2)(Lonza) and plated onto T75 flasks coated with 100 μg/mL fibrinogen.

iPSC-EC Culture and Passage iPSC-ECs were passaged and grown up to passage 4. After aspirating media, iPSC-EC were washed in PBS and dissociated using TrypLE™ for 5 minutes at room temperature. Cells were resuspended in EGM2 media and centrifuged at 300 g for 10 minutes. Cells were replated at $1\times10^4$ cells/cm$^2$ onto T25 flasks coated with 100 μg/mL fibrinogen or 4-chamber culture slides (BD) coated with 100 μg/mL fibrinogen. Media was changed every 2 days, and cells were grown up to day 6 prior to re-passaging.

iPSC-EC Staining

Fixed iPSC-ECs were stained for endothelial markers. iPSC-EC cultured on 4-well culture slides coated with 100 μg/mL fibrinogen were fixed with ice cold methanol for 5 minutes. The methanol was washed out 3× with PBS. Fixed cells were blocked for 45 minutes at room temperature using blocking solution (6% normal goat serum, 0.3% Triton™ X-100 (Sigma-Aldrich®) in PBS). Cells were incubated with one of the following primary antibodies overnight at 4° C.: (A) 10 μg/mL Anti-CD31 (BBA7, RND Systems) or (B) 10 μg/mL FITC-labeled UEA-Lectin (Vector Labs). Wells were washed 3× with PBS. Then for the CD31 staining only, 10 μg/mL of FITC-anti-Mouse secondary antibody in 0.3% TX-PBS was incubated with the cells for 1 hour at room temperature. Wells were again washed, and the slide was fluromounted and coversliped. The slide was imaged using a fluorescent microscope (Nikon).

Figure 36:
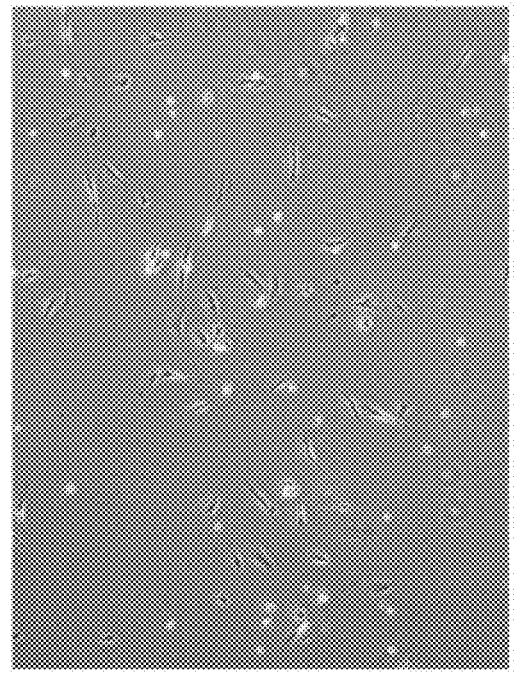
FIG. 36 contains photographs of pre-differentiated iPSC-ECs cultured after being cultured in Endothelial Growth Media (EGM-2) for 1 day. The iPSC-ECs were differentiated on Matrigel®, then $2.5\times10^5$ iPSC-ECs were plated onto a T25 flask coated with 100 µg/mL fibrinogen. The iPSC-EC appear in their characteristic spindle shape with round nuclei.
Figure 36:
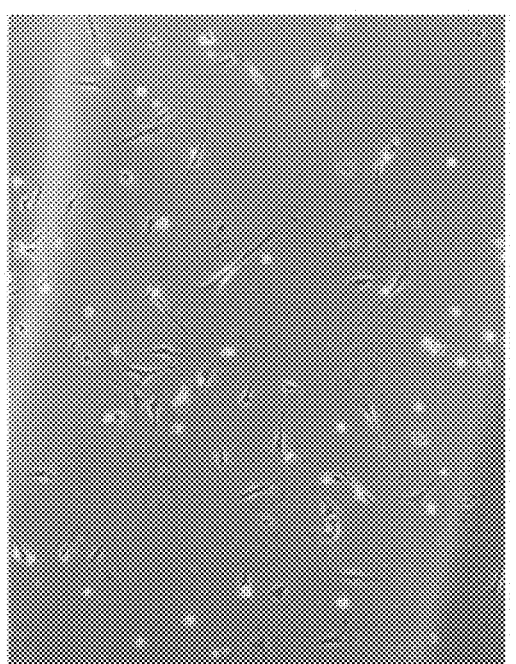

Results iPSC-EC Culture iPSC-ECs were previously differentiated as described elsewhere (Orlova et al., *Nat. Protoc.*, 9:1514-1531 (2014)). This protocol used Matrigel® coated 6 well plates to initiate differentiation of iPSCs to ECs. After successful purification and culture on Matrigel®, iPSC-EC were passaged using TrypLE™ onto fibrinogen coated plates. iPSC-EC attached successfully to the fibrinogen coated plates, and appeared in the typical spindle-shaped phenotype (FIG. 36).

Figure 37:
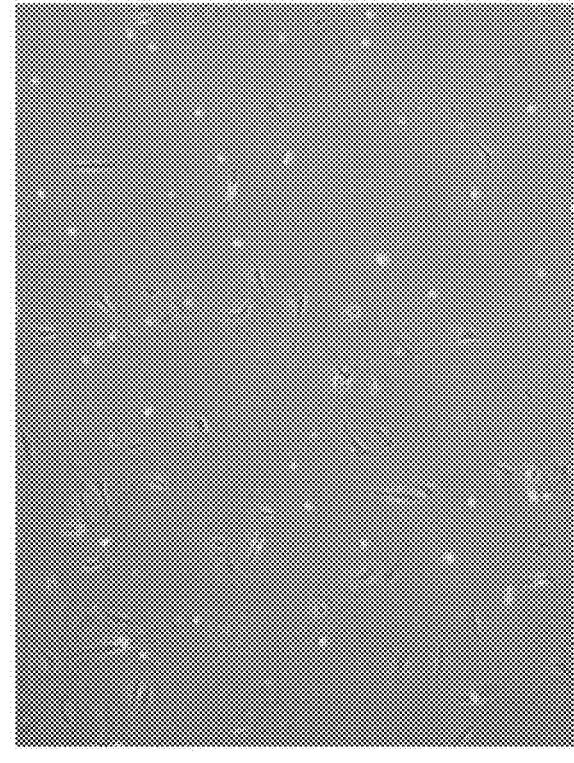
FIG. 37 contains photographs of iPSC-ECs that were differentiated directly on fibrinogen coated plates after being cultured in EGM-2 for 1 day. $2.5\times10^5$ iPSC-ECs were plated onto a T25 flask coated with 100 µg/mL fibrinogen. The iPSC-EC appear in their characteristic spindle shape with round nuclei.
Figure 37:
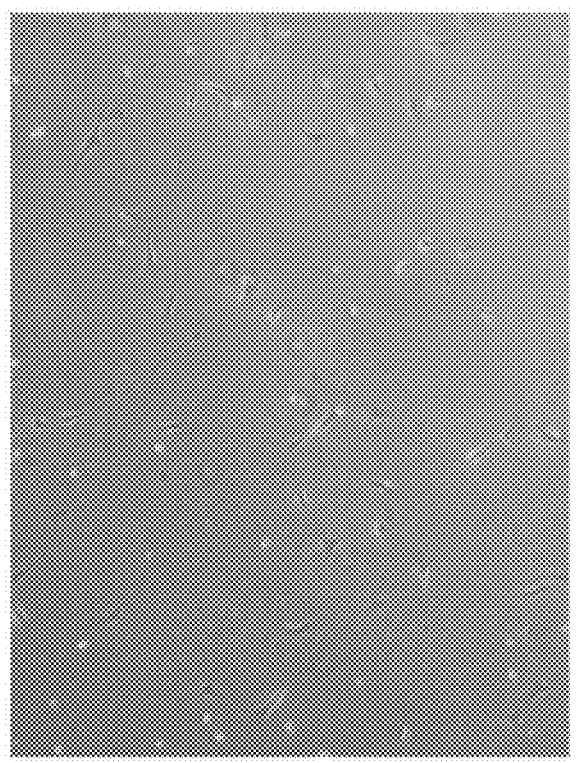
Figure 38:
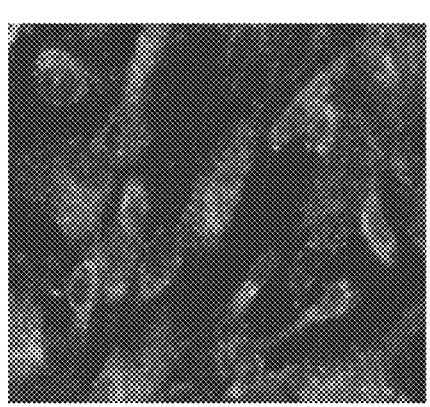
FIG. 38 contains photographs of iPSC-ECs differentiated on fibrinogen coated plates. Immunofluorescent staining was performed for endothelial markers including CD31 and UEA-Lectin. CD31 staining appears on the cell surface and within the cytoplasm, around the nuclei. UEA-Lectin staining appears uniformly across the surface of the cells.
Figure 38:
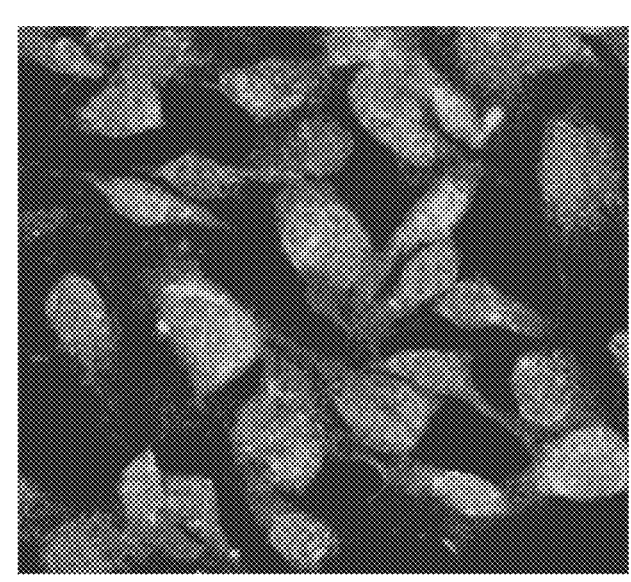

To test if fibrinogen coated plates could be used to differentiate iPSCs, the previously mentioned protocol was modified to use fibrinogen-coated 6 well plates for initial iPSC attachment. After differentiation, iPSC-EC were purified and replated onto a t75 coated with fibrinogen. iPSC-ECs appeared in the characteristic spindle shape with rounded nuclei (FIG. 37). Immunofluorescent staining of iPSC-EC revealed positive staining for CD31 and UEA-Lectin (FIG. 38).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for making, from stem cells, a flat retinal pigment epithelium monolayer within a container, wherein said method comprises culturing stem cells in a container having a surface coated with soluble and clottable fibrinogen and comprising a medium capable of differentiating said stem cells into retinal pigment epithelium cells capable of forming said flat retinal pigment epithelium monolayer, wherein said surface was coated with about 3 μg/mL to about 1000 μg/mL of said soluble and clottable fibrinogen, wherein said stem cells are in contact with said soluble and clottable fibrinogen, wherein said stem cells differentiate into said retinal pigment epithelium cells in said container, and wherein said retinal pigment epithelium cells form said flat retinal pigment epithelium monolayer in said container.

2. The method of claim 1, wherein said surface comprises polystyrene, polycarbonate, mixed cellulose, polytetrafluoroethylene (PTFE), polydimethylsiloxane (PDMS), polyethylene terephthalate (PET), glass, a poly-L-lysine coating, or a combination thereof.

3. The method of claim 1, wherein said fibrinogen is human fibrinogen.

4. The method of claim 1, wherein said surface was coated by exposing said surface to a solution comprising said fibrinogen for about 1 to about 48 hours.

5. The method of claim 1, wherein said method comprises culturing said cells for from about 7 days to about 90 days to form said retinal pigment epithelium monolayer.

6. The method of claim 1, wherein said method is xeno-free.

* * * * *